(12) United States Patent
Laursen et al.

(10) Patent No.: US 10,364,249 B2
(45) Date of Patent: Jul. 30, 2019

(54) AZATRIANGULENIUM SALTS AS PET-QUENCHED FLUORESCENT PROBES

(71) Applicant: KØBENHAVNS UNIVERSITET, Copenhagen K (DK)

(72) Inventors: Bo V. Laursen, Roskilde (DK); Martin Rosenberg, Copenhagen K (DK); Thomas Just Sorensen, Copenhagen S (DK)

(73) Assignee: Kobenhavns Universitet, Copenhagen K (DK)

( * ) Notice: Subject to any disclaimer, the term of this patent is extended or adjusted under 35 U.S.C. 154(b) by 166 days.

(21) Appl. No.: 15/028,558

(22) PCT Filed: Oct. 24, 2014

(86) PCT No.: PCT/DK2014/050350
§ 371 (c)(1),
(2) Date: Apr. 11, 2016

(87) PCT Pub. No.: WO2015/058777
PCT Pub. Date: Apr. 30, 2015

(65) Prior Publication Data
US 2016/0251369 A1    Sep. 1, 2016

(30) Foreign Application Priority Data
Oct. 24, 2013  (DK) .................................. 2013 70616

(51) Int. Cl.
*C07D 491/00*    (2006.01)
*C07D 491/16*    (2006.01)
(Continued)

(52) U.S. Cl.
CPC ......... *C07D 491/16* (2013.01); *C07D 471/14* (2013.01); *C07D 471/16* (2013.01);
(Continued)

(58) Field of Classification Search
CPC .................................................... C07D 491/16
(Continued)

(56) References Cited

PUBLICATIONS

Mobian et al. J. Am. Chem. Soc. 2008, 130, 6507-6514 (Year: 2008).*
Maliwal BP, Fudala R, Raut S, Kokate R, Sørensen TJ, et al. (2013) Long-Lived Bright Red Emitting Azaoxa-Triangulenium Fluorophores. PLoS ONE 8(5): e63043. doi:10.1371/journal.pone.0063043 (Year: 2013).*
B.W. Laursen: "Triangulenium Qalts"; Wenmark. Forsknings Center Risoe. Risoe-r. Risoe dtu. Nationallaboratoriet for Baeredygti gt energi. Dk. Jun. 15, 2001 (Jun. 15, 2001). pp. 1-168.
(Continued)

*Primary Examiner* — Christine T Mui
*Assistant Examiner* — Emily R. Berkeley
(74) *Attorney, Agent, or Firm* — Harness, Dickey & Pierce, P.L.C.

(57) ABSTRACT

The present invention relates to a new class of substituted aza-triangulenium fluorescent dyes having a hydroxy group attached to an aryl as quenching group. The new substituted aza-triangulenium fluorescent dyes may be attached to a linker, conjugated to carrier molecule such as e.g. a protein, a nucleic acid, a lipid, or a saccharide, or deposited or immobilized on solid support materials. The substituted aza-triangulenium fluorescent dyes are useful for various purposes, including use in sensors for monitoring or determining the concentration of analytes, such as $H^+(pH)$, $Na^+$, $K^+$, $Ca^{2+}$, $O_2$, $CO_2$, $H_2O_2$, ionic strength, redox potentials, metal ions, and metabolites.

14 Claims, 11 Drawing Sheets

(51) Int. Cl.
- *C07F 7/18* (2006.01)
- *C07D 471/14* (2006.01)
- *C07D 491/14* (2006.01)
- *C07D 471/16* (2006.01)
- *C09B 69/00* (2006.01)
- *G01N 21/64* (2006.01)
- *C09B 15/00* (2006.01)
- *C09K 11/06* (2006.01)

(52) U.S. Cl.
CPC .......... *C07D 491/14* (2013.01); *C07F 7/1804* (2013.01); *C09B 15/00* (2013.01); *C09B 69/00* (2013.01); *C09B 69/008* (2013.01); *C09K 11/06* (2013.01); *G01N 21/6428* (2013.01); *G01N 2021/6439* (2013.01)

(58) Field of Classification Search
USPC .......................................................... 436/172
See application file for complete search history.

(56) References Cited

PUBLICATIONS

T.J. Soerensen et al: "Azadioxatriangulenium: a long fluorescence lifetime fluorophore for large biomolecule binding assay". Methods and applications in fluorescence. vol. 1. No. 2. Apr. 3, 2013 (Apr. 3, 2013). pp. 1-6.

P. Hammershoj et al: "Base-Assisted One-pot Synthesis of N,N',N"-triaryltriazatriangulenium dyes: enhanced fluorescence efficiency by steric constraints". The Journal of Organic Chemistry. vol. 77. May 22, 2012 (May 22, 2012). pp. 5606-5612.

Dileesh S. "Photoinduced Electron Transfer in Azatriangulenium Salts". Journal of Photochemistry and Photobiology. A: Chemistry. vol. 162. No. 1. 2004. pp. 115-120.

International Search Report regarding Application No. PCT/DK2014/050350, dated Jan. 13, 2015.

Written Opinion regarding Application No. PCT/DK2014/050350, dated Jan. 13, 2015.

\* cited by examiner

Figure 1a1
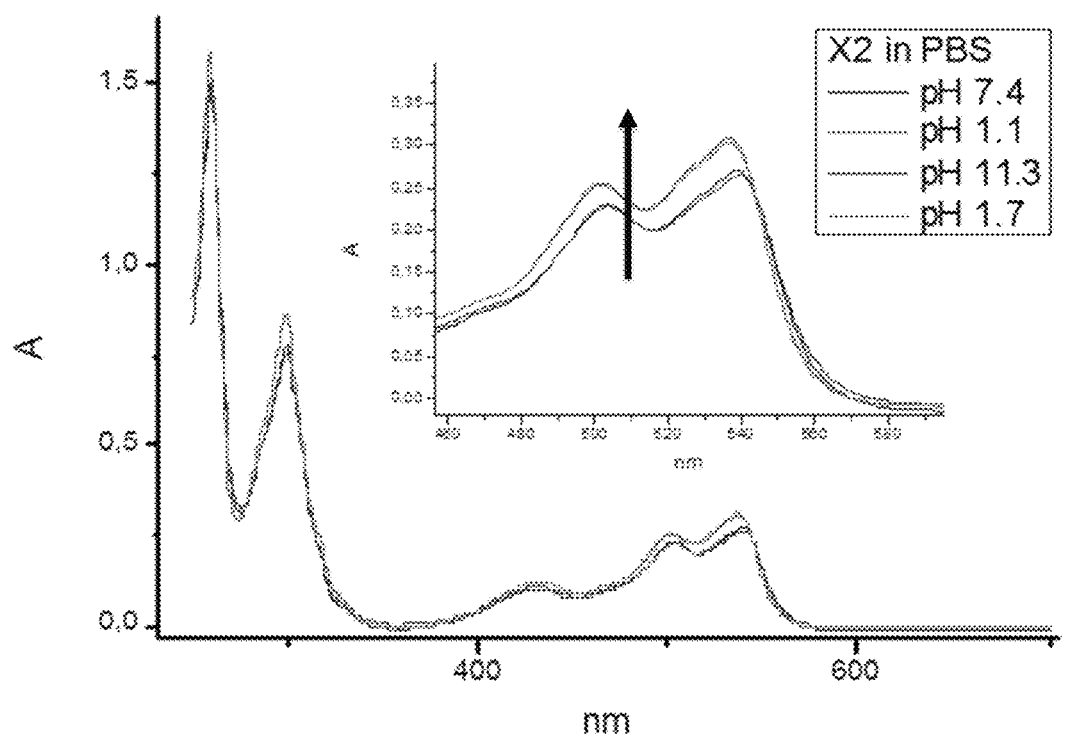

Figure 1a2
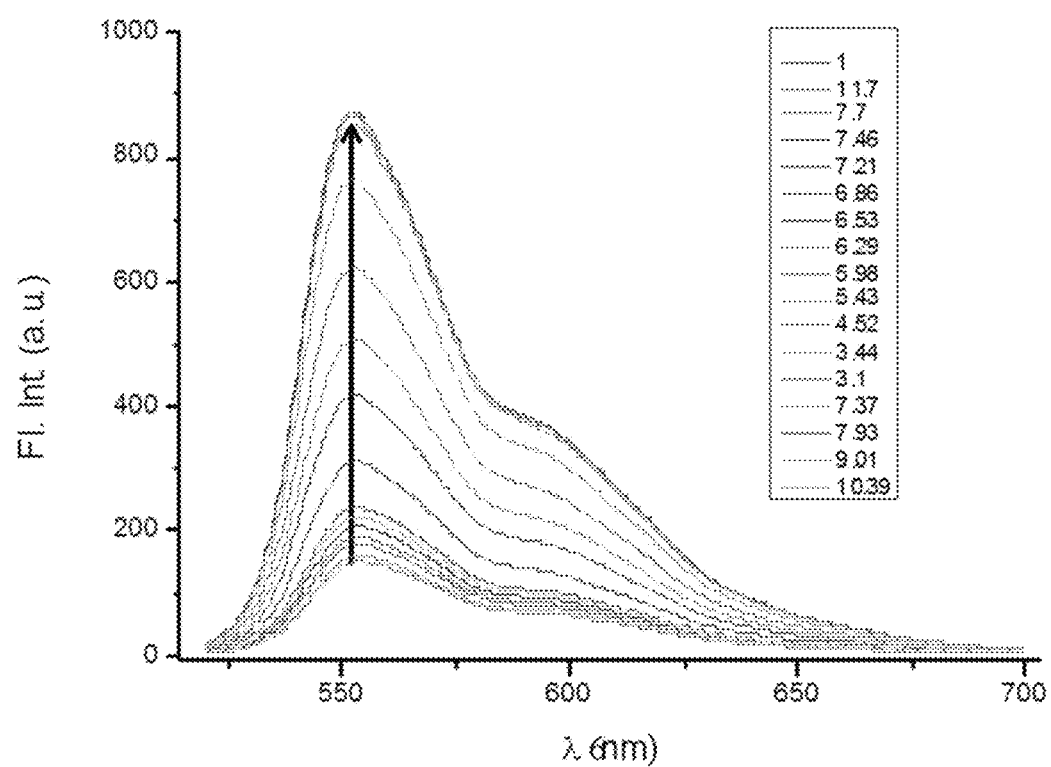

Figure 1b1
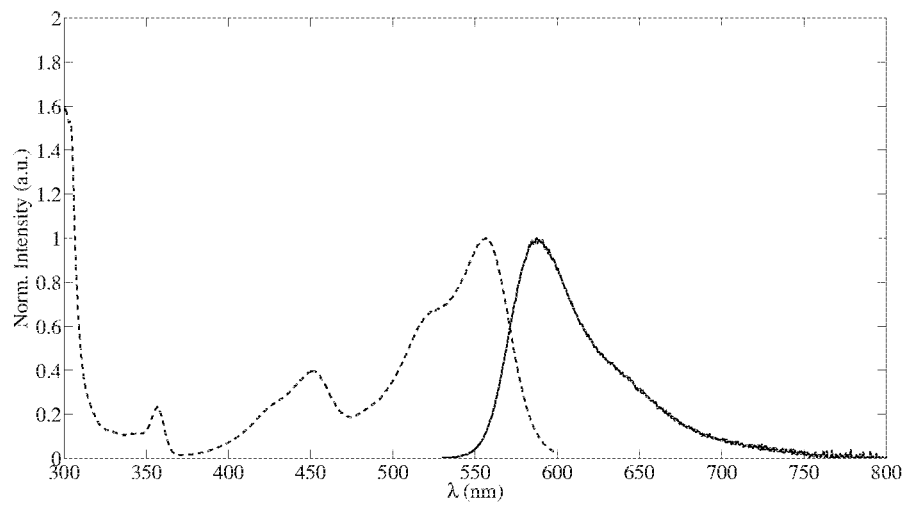
Figure 1b2.
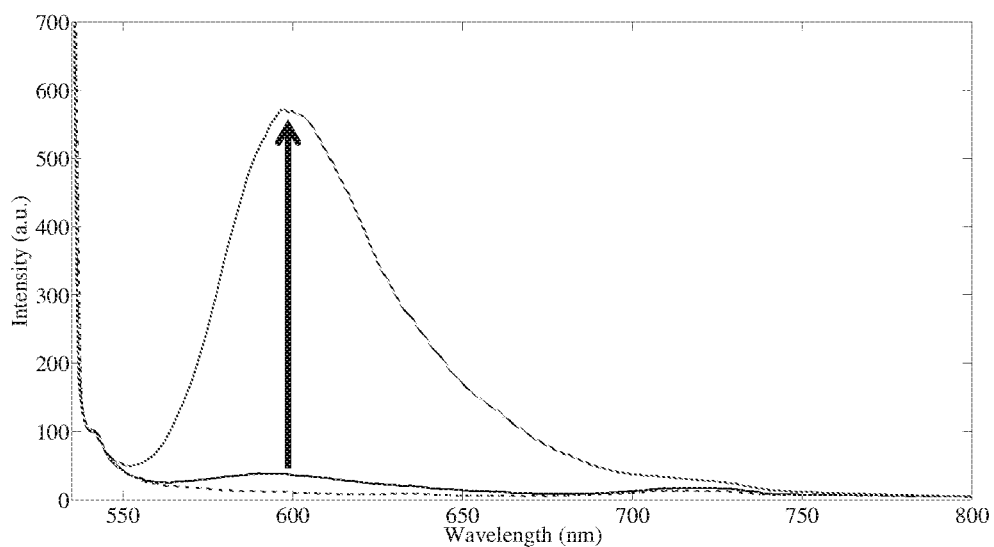

Figure 2a1.
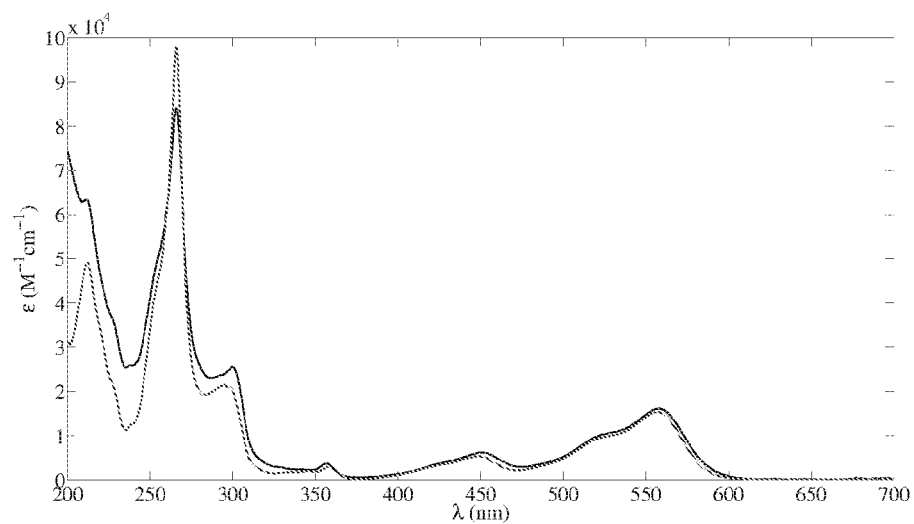
Figure 2a2.
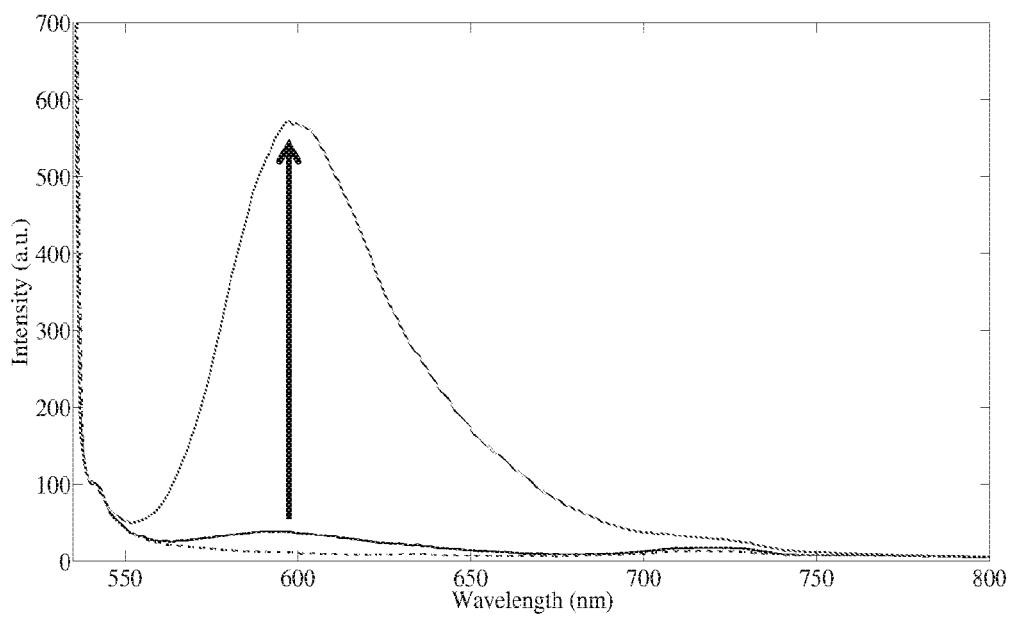

AZATRIANGULENIUM SALTS AS PET-QUENCHED FLUORESCENT PROBES

CROSS-REFERENCE TO RELATED APPLICATIONS

This application is a U.S. National Phase Application under 35 U.S.C. 371 of International Application No. PCT/DK2014/050350, filed Oct. 24, 2014, and published in English as WO 2015/058777 A1 on Apr. 30, 2015. This application is based on and claims priority to Danish Patent Application No. PA 2013 70616, filed Oct. 24, 2013. The entire disclosures of the above applications are incorporated herein by reference.

INTRODUCTION

The present invention relates to a new class of substituted aza-triangulenium fluorescent dyes having a hydroxy group attached to an aryl as quenching group. The new substituted aza-triangulenium fluorescent dyes may be attached to a linker, conjugated to carrier molecule such as e.g. a protein, a nucleic acid, a lipid, or a saccharide, or deposited or immobilised on solid support materials. The substituted aza-triangulenium fluorescent dyes are useful for various purposes, including use in sensors for monitoring or determining the concentration of analytes, such as $H^+$(pH), $Na^+$, $K^+$, $Ca^{2+}$, $O_2$, $CO_2$, $H_2O_2$, metal ions, ionic strength, redox potentials, and metabolites.

BACKGROUND OF THE INVENTION

Fluorescence offers an ideal solution for detection and sensing applications, as readout signals of probes or sensors containing fluorescent molecules are done by light.[1-4] The probe or sensor may be read by using a microscopy, a spectrometer, the naked eye, CCD detectors, and cameras either directly or through fiber optics. Responsive sensor molecules are interesting in their own merit, and in particularly as they are the cornerstone in responsive imaging and sensing technology.

Two different types of responsive fluorescent molecules relevant for the present invention can be found in the literature: fluorophores where the binding/release of an analyte changes the intrinsic properties of the fluorophores e.g. fluorescein[10, 11] and HPTS[12], and fluorophores where binding of an analyte to an appended binding motive turns on/off the fluorescence of the fluorophores.[13-15] The latter can be realized appending a photoinduced electron transfer (PET) quenching[16] motif to a good fluorophore[9, 17].

When a PET responsive fluorescent molecule absorbs a photon, an excited electronic state is created and an electron transfer prevents the excited molecule from emitting a photon. Thus, the fluorescence of the dye is quenched. Binding of an analyte to the acceptor/donor PET group changes its nature blocks the possibility of PET-quenching of the fluorophore. As a result, the fluorescent reporter moiety responds e.g. to a change in analyte concentration of the surrounding medium. Because binding of the analyte to the acceptor/donor group cancels the PET-quenching process, the fluorescence properties of PET-based sensors change as the concentration of the analyte changes.

pH is still the most crucial parameter in both biological and medicinal research and in the biotech industry. Cells are grown in media containing pH-indicators, and in every part of a biotechnological production line, pH is monitored directly. Fluoroscein is today, despite poor photostability, one of the most used pH-responsive fluorescence dyes, either as a cheap native, carboxy- or amino derivative, or as the expensive extended SNARF-type dyes.

Triangulenium compounds have for long been target molecules for research, as characterisation of some triangulenium compounds shows that these compounds may have some interesting optical properties. Triangulenium compounds may be described as comprising tris(2,6-dimethoxyphenyl)-methylium, $DMP_3C^+$, as backbone. Two methoxy groups may be fused together or replaced by e.g. a nitrogen atom to form a 6-membered ring structure comprising the two carbon atoms to which the methoxy groups are attached. The other remaining methoxy groups may optionally also be fused together or replaced by another atom, e.g. a carbon, oxygen, sulphur, or nitrogen atom. Thus, one, two or three 6-membered ring structures may be formed. Depending on the number of ring structures and the choice of the replacing atoms, different triangulenium compounds may be formed, amongst other TMA, ADOTA, DAOTA, and TATA WO2005012436 discloses fluorescent dyes compounds belonging to the ADOTA subgroup. These compounds are suitable for use in visualisation of chemical compounds in e.g. chromatographic separation. The disclosed compounds contain at least two secondary or tertiary amine groups, which each are attached to a phenyl group present in the ADOTA subgroup. Further, the disclosed compounds also contain a functional group, which according to WO2005012436, allows the fluorescent dye to be attached.

Hamacek et at, Dalto Trans, 2012, 41, 6777-6782, discloses substituted compounds of the ADOTA, DAOTA, TATA subgroups. It is suggested to use these compounds for complexing with metallic cations. The luminescence and phosphorescence characteristics of the bonded metallic cation, $Eu^{3+}$, are discussed.

Laursen, B. et at, Chem. Eur. J. 2001, No. 8, 1773-1783, discloses substituted compounds of the ADOTA, DAOTA, TATA subgroups. The absorption spectra of these compounds in their neutral and protonated form are discussed.

Hammerhoej et at, J. Org. Chem. 2012, 77, 5606-5612, discloses substituted aza-triangulenium fluorescent properties. The absorption and emission spectra of these compounds are discussed.

Research for developing new aza-triangulenium fluorescent dyes having improved photophysical properties is continuously ongoing. Accordingly, it would therefore be advantageously to find new fluorescent dyes having altered or improved photophysical properties, such as improved sensitivity and higher stability. Such compounds would be useful in sensors for monitoring or determining analytes. Therefore, the aim of the present invention is to provide improved fluorescent dyes having improved sensitivity, broad versatility as to range of analytes, large dynamic range, and/or photostability during use.

SUMMARY OF THE INVENTION

With this background, it is an object of the present invention in a first embodiment to provide a fluorescent dye compound of Formula (I)

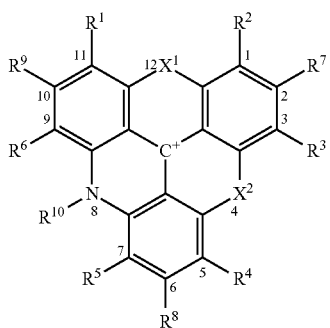

(I)

wherein

X¹ denotes NR¹¹, O, S, or C(R¹¹)₂, or denotes two individual substituted or unsubstituted C₁-C₂₄-alkoxy groups, which each are linked to the two adjacent carbon atoms, X² denotes NR¹², O, S, or C(R¹²)₂, or denotes two individual substituted or unsubstituted C₁-C₂₄-alkoxy groups, which each are linked to the two adjacent carbon atoms, R¹, R², R³, R⁴, R⁵, R⁶, R⁷, R⁸, R⁹, R¹⁰, R¹¹ and R¹² are independently selected from the group comprising hydrogen, cyano, halogen, hydroxy, nitro, acyl, acylamino, acyloxy, C₁-C₂₄-alkyl, C₁-C₂₄-alkenyl, C₁-C₂₄-alkynyl, aryl, C₁-C₂₄-alkoxy, C₁-C₂₄-alkylsulfonyl, methylsulfonyl, triflouromethyl, amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, sulfonyl, sulfonyloxy, thioacyl, thiol, thiocarbonyl, C₁-C₂₄-alkylthio, heteroaryl, cycloalkyl, phenyl, hydroxyphenyl, aminophenyl, amino-C₁-C₂₄-alkyl, or heterocyclyl, such as a 5- or 6-membered heterocyclyl containing at least one nitrogen or sulphur atom, or two of R¹, R², R³, R⁴, R⁵, R⁶, R⁷, R⁸, R⁹, R¹⁰, R¹¹ and R¹² may together form a ringsystem; R¹, R², R³, R⁴, R⁵, R⁶, R⁷, R⁸, R⁹, R¹⁰, R¹¹ and R¹² optionally being substituted once, twice, or three times with R¹³ group(s), or a -L-Si(OR₁₄)₃ group, R¹³ is independently selected form the group comprising hydrogen, cyano, halogen, hydroxy, nitro, acyl, acylamino, acyloxy, C₁-C₂₄-alkyl, C₁-C₂₄-alkenyl, C₁-C₂₄-alkynyl, aryl, C₁-C₂₄-alkoxy, C₁-C₂₄-alkylsulfonyl, methylsulfonyl, triflouromethyl, amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, sulfonyl, sulfonyloxy, thioacyl, thiol, thiocarbonyl, C₁-C₂₄-alkylthio, heteroaryl, or a cycloalkyl, or two R¹³ substituents may together form a ring system, R¹⁴ is independently selected from the group comprising hydrogen, or straight or branched C₁-C₆ alkyl, alkenyl, or alkynyl, and one or more of the subgroups R¹, R², R³, R⁴, R⁵, R⁶, R⁷, R⁸, R⁹, R¹⁰, R¹¹ or R¹² is/are a quenching group independently selected from the group comprising phenyl substituted with one to five groups R¹³, wherein at least one R¹³ group is hydroxy, or a group selected from indole, benzoefuran, naphthalene, or 5- or 6-membered heterocyclyl or C₁-C₆ alkylene heterocyclyl containing at least one of N, NH, O, or S, said group optionally being substituted one, two, or three times with R¹³ group(s), wherein at least one R¹³ group is hydroxy.

It has surprisingly been found that compounds of Formula (I) comprising dyes having a hydroxy group attached to an aryl as quenching group have PET responsive properties. In a certain embodiment of the invention, the compounds of Formula (I) are sensitive towards the concentration of analytes, such as H⁺(pH), Na⁺, K⁺, Ca²⁺, O₂, CO₂, H₂O₂, metal ions, metabolites, and other suitable analytes. In a particular embodiment, quenching of the dyes having a hydroxy group attached to an aryl as quenching group may be obtained at low or high pH, such as pH lower than 5.5 or pH higher than 9.5. The quenching characteristic may be modified by attachment of substituents being either electron negative, such as —NO₂, or electron positive, such as —CF₃, to the aryl group.

Alkoxyphenols, e.g. such as methoxyphenol, can not inherently function as a quenching group. The hydroxy moiety of phenol may preferable be protected by an alkyl, such as methyl, when preparing compounds of Formula (I). Thus, component comprising alkoxyphenols may be regarded as intermediates, when preparing Compounds of Formula (I), and are also part of the invention.

The compounds of the above general formula may be subdivided in several subtypes. Thus, in a first subtype the backbone of the compounds of Formula (I) according to the present invention contains in the X¹ and X² positions four methoxy groups forming the ring structure, TMA⁺, cf. Table 1. Depending on the specific choice of X¹ and X², different aza-triangulenium compounds may be obtained. Thus, for example, X¹ may denote a second nitrogen atom, whereas X² may denote two methoxy groups. Hence, several different subtypes of aza-triangulenium compounds exist, cf. Table 1.

TABLE 1

List of different examples of aza-triangulenium subgroups/systems.

| Aza-triangulenium compounds, subtypes | | Subtype examples: |
|---|---|---|
| X¹ | X² | |
| Two methoxy groups | Two methoxy groups | TMA⁺ |
| NR¹¹ | Two methoxy groups | DMQA⁺ |

TABLE 1-continued

List of different examples of aza-triangulenium subgroups/systems.

| Aza-triangulenium compounds, subtypes | | |
|---|---|---|
| $X^1$ | $X^2$ | Subtype examples: |
| $NR^{11}$ | O | 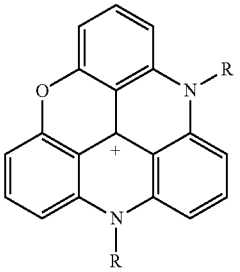 DAOTA$^+$ diazaoxa-triangulenium |
| O | O | 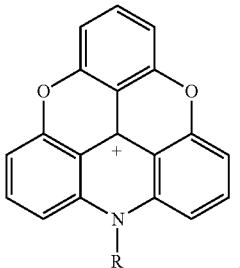 ADOTA$^+$ azadioxa-triangulenium, |
| $NR^{11}$ | $NR^{12}$ | 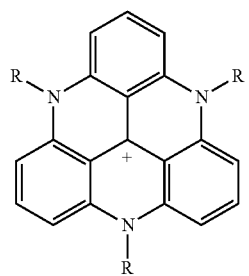 TATA$^+$ triaza-triangulenium |
| $NR^{11}$ | $C(R^{12})_2$ | 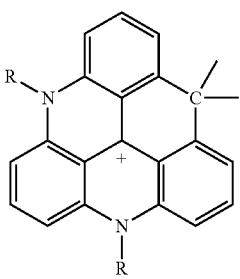 |
| O | $C(R^{12})_2$ | 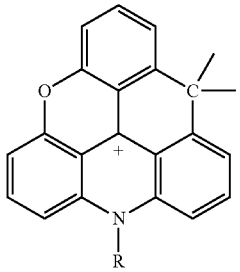 |
| $NR^{11}$ | S | 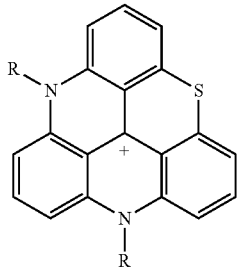 |
| O | S | 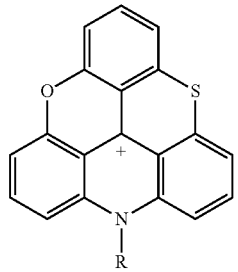 |

In an embodiment of the present invention, compounds of Formula (I) at least one of the following subgroups, $R^{10}$, $R^{11}$ and $R^{12}$ is a quenching group independently selected from the group comprising phenol, benzoefuran, indole, pyrrolidine, pyrrole, thiolane, thiophene, imidazolidine, pyrazolidine, imidazole, pyrazole, oxazolidine, isoxazolidine, oxazole, isoxazole, thiazolidine, isothiazolidine, thiazole, isothiazole, dithiolane, triazoles, furazan, oxadiazole, thiadiazole, dithiazole, tetrazole, piperidine, pyridine, thiane, thiopyran, piperazine, diazines, oxazine, thiazine, dithiane, dithiine, triazine, or tetrazine; $R^{10}$, $R^{11}$ and $R^{12}$ optionally being substituted one, two, or three times with $R^{13}$ group(s), are comprised by the present invention. In particular, one or more of the carbon atoms of a phenyl group may be substituted one, two or three times with $R^{13}$ group(s).

In another embodiment, compounds of Formula (I) wherein $R^{10}$, $R^{11}$ and $R^{12}$ is a quenching group independently selected from the group comprising 2-phenol, 3-phenol, and 4-phenol, hydroxy-indole, hydroxy-pyrrolidine, hydroxy-pyrrole, hydroxy-thiophene said group optionally being substituted one, two, or three times with $R^{13}$ group(s), are also comprised by the present invention. In particular, one or more of the carbon atoms of the phenyl group may be substituted one, two or three times with $R^{13}$ group(s).

In a more specific embodiment, compounds of Formula (I) such as 9-(2,6-dimethoxyphenyl)-1,8-dimethoxy-10-(2-methoxyphenyl)-acridinium, 1b,
9-(2,6-dimethoxyphenyl)-10-(3-hydroxyphenyl)-1,8-dimethoxy-acridinium, 1c,
9-(2,6-dimethoxyphenyl)-10-(4-hydroxyphenyl)-1,8-dimethoxy-acridinium, 1d,
10-(4-aminophenyl)-9-(2,6-dimethoxyphenyl)-1,8-dimethoxy-9,10-acridinium, 1e,
9-(2,6-dimethoxyphenyl)-10-(5-fluoro-2-methoxyphenyl)-1,8-dimethoxy-acridinium, 1f,
9-(2,6-dimethoxyphenyl)-10-(2-hydroxy-5-(methylsulfonyl)phenyl)-1,8-dimethoxy-acridinium, 1g,
9-(2,6-dimethoxyphenyl)-1,8-dimethoxy-10-(2-methoxy-5-(trifluoromethyl)phenyl)-acridinium, 1h,
5-(dodecyl)-9-(3-hydroxyphenyl)-1,13-dimethoxy-quin[2,3,4-kl]acridinium, 2c),
5-(dodecyl)-9-(5-fluor-2-hydroxyphenyl)-1,13-dimethoxy-quin[2,3,4-kl]acridinium, 2f,
5-(dodecyl)-9-(5-methylsulfonyl-2-hydroxyphenyl)-1,13-dimethoxy-quin[2,3,4-kl]acridinium, 2g,
5-(dodecyl)-9-(5-trifluormethyl-2-hydroxyphenyl)-1,13-dimethoxy-quin[2,3,4-kl]acridinium, 2h,
4-(3-morpholinopropyl)-4-aza-8,12-dioxa-4,8,12,12c-tetrahydro-dibenzo[cd,mn]-pyrenylium, 3a,
12-(2-hydroxyphenyl)-4-aza-8,12-dioxa-4,8,12,12c-tetrahydro-dibenzo[cd,mn]-pyrenylium, 3b,
12-(3-hydroxyphenyl)-4-aza-8,12-dioxa-4,8,12,12c-tetrahydro-dibenzo[cd,mn]-pyrenylium, 3c,
12-(4-)-4-aza-8,12-dioxa-4,8,12,12c-tetrahydro-dibeny[cd,mn]-pyrenylium, 3d,
12-(4-aminophenyl)-4-aza-8,12-dioxa-4,8,12,12c-tetrahydro-dibenzo[cd,mn]-pyrenylium, 3e,
4-dodecyl-8-(2-hydroxyphenyl)-4,8-diaza-12-oxa-4,8,12,12c-tetrahydro-dibenzo[cd,mn]-pyrenylium, 4b,
4-(4-aminophenyl)-8-(3-hydroxypropyl)-4,8-diaza-12-oxa-4,8,12,12c-tetrahydro-dibenzo[cd,mn]-pyrenylium, 4e,
4-dodecyl-8-(5-fluoro-2-hydroxyphenyl)-4,8-diaza-12-oxa-4,8,12,12c-tetrahydro-dibenzo[cd,mn]-pyrenylium, 4f,
4-dodecyl-8-(2-hydroxy-5-(methylsulfonyl)phenyl)-4,8-diaza-12-oxa-4,8,12,12c-tetrahydro-dibenzo[cd,mn]-pyrenylium, 4g,
4-dodecyl-8-(2-hydroxy-5-trifluoromethyl-phenyl)-4,8-diaza-12-oxa-4,8,12,12c-tetrahydro-dibenzo[cd,mn]-pyrenylium, 4h,
4-propyl-8-(2-hydroxyphenyl)-4,8-diaza-12-oxa-4,8,12,12c-tetrahydro-dibenzo[cd,mn]-pyrenylium 4i,
4-propyl-8-(3-hydroxyphenyl)-4,8-diaza-12-oxa-4,8,12,12c-tetrahydro-dibenzo[cd,mn]-pyrenylium 4j,
4-propyl-8-(4-hydroxyphenyl)-4,8-diaza-12-oxa-4,8,12,12c-tetrahydro-dibenzo[cd,mn]-pyrenylium 4k,
4-propyl-8-(5-fluoro-2-hydroxyphenyl)-4,8-diaza-12-oxa-4,8,12,12c-tetrahydro-dibenzo[cd,mn]-pyrenylium 4l,
4-propyl-8-(5-trifluormethyl-2-hydroxyphenyl)-4,8-diaza-12-oxa-4,8,12,12c-tetrahydro-dibenzo[cd,mn]-pyrenylium 4m,
4-propyl-8-(2-hydroxy-5-(methylsulfonyl)phenyl)-4,8-diaza-12-oxa-4,8,12,12c-tetrahydro-dibenzo[cd,mn]-pyrenylium, 4n,
8-(hydroxy-pyridin)-4,8-diaza-12-oxa-4,8,12,12c-tetrahydro-dibenzo[cd,mn]-pyrenylium, 4o,
8-(hydroxy-1-methyl-1H-pyrrol)-4,8-diaza-12-oxa-4,8,12,12c-tetrahydro-dibenzo[cd,mn]-pyrenylium, 4p,
8-(hydroxy-thiophen)-4,8-diaza-12-oxa-4,8,12,12c-tetrahydro-dibenzo[cd,mn]-pyrenylium, 4q,
8-(hydroxy-1-methyl-1H-indol)-4,8-diaza-12-oxa-4,8,12,12c-tetrahydro-dibenzo[cd,mn]-pyrenylium, 4r,
8-(hydroxy-naphthalen)-4,8-diaza-12-oxa-4,8,12,12c-tetrahydro-dibenzo[cd,mn]-pyrenylium, 4s, 4t,
8-(hydroxybenzofuranyl)-4,8-diaza-12-oxa-4,8,12,12c-tetrahydro-dibenzo[cd,mn]-pyrenylium, 4u,
4-(2-hydroxy-5-methylsulfonyl-phenyl)-8,12-diphenyl-4,8,12-triaza-4,8,12,12c-tetrahydro-dibenzo[cd,mn]-pyrenylium, 5,
4-(2-hydroxy-5-methylsulfonyl-phenyl)-8,12-diphenyl-4,8,12-triaza-4,8,12,12c-tetrahydro-dibenzo[cd,mn]-pyrenylium, 5
9-(2,6-dimethoxyphenyl)-1,8-dimethoxy-10-(2-methoxyphenyl)-9,10-dihydroacridinium hexafluorophosphate, MR-68-Acr,
4-(2-hydroxyphenyl)-4-aza-8,12-dioxatriangulenium hexafluorophophate, MR-68.1-ADOTA,
4-(2-hydroxyphenyl)-8-methyl-4,8-diaza-12-oxatriangulenium hexafluorophosphate, MR-68-DAOTA,
9-(2,6-dimethoxyphenyl)-1,8-dimethoxy-10-(3-methoxyphenyl)-9,10-dihydroacridinium hexafluorophosphate, MR-73_Acr,
4-(3-hydroxyphenyl)-4-aza-8,12-dioxatriangulenium hexafluorophophate, MR-73-ADOTA,
4-(3-hydroxyphenyl)-8-methyl-8-aza-8,12-dioxatriangulenium hexafluorophosphate, MR-73.1-DAOTA,
9-(2,6-dimethoxyphenyl)-1,8-dimethoxy-10-(4-methoxyphenyl)-9,10-dihydroacridinium hexafluorophosphate, MR-93_Acr,
4-(4-hydroxyphenyl)-4-aza-8,11-dioxatriangulenium hexafluorophosphate, MR-93_ADOTA,
4-(4-hydroxyphenyl)-4,8-diaza-11-oxatriangulenium hexafluorophosphate, MR-93_DAOTA,
9-(2,6-dimethoxyphenyl)-1,8-dimethoxy-10-(2-methoxy-5-(trifluoromethyl)phenyl)-9,10-dihydroacridinium hexafluorophosphate, MR-66_Acr,
4-(2-hydroxy-5-(trifluoromethyl)phenyl)-3-aza-8,11-dioxatriangulenium hexafluorophosphate, MR-66.1_ADOTA,
4-(2-hydroxy-5-(trifluoromethyl)phenyl)-8-methyl-8-aza-11-oxatriangulenium hexafluorophosphate, MR-66_DAOTA,
9-(2,6-dimethoxyphenyl)-1,8-dimethoxy-10-(3-methoxy-5-(trifluoromethyl)phenyl)-9,10-dihydroacridinium hexafluorophosphate, MR-67.1_Acr,
4-(3-hydroxy-5-(trifluoromethyl)phenyl)-4-aza-8,11-dioxatriangulenium hexafluorophosphate, MR-67.1_ADOTA,
4-(3-hydroxy-5-(trifluoromethyl)phenyl)-4-methyl-4,11-diaza-8-oxatriangulenium hexafluorophosphate, MR-67.1_DAOTA,
9-(2,6-dimethoxyphenyl)-1,8-dimethoxy-10-(2-methoxy-5-nitrophenyl)-9,10-dihydroacridinium hexafluorophosphate, MR-69.1,
3-(2-hydroxy-5-nitrophenyl)-7,10-dioxa-3-azatriangulenium hexafluorophosphate, MR-69.1_ADOTA,
4-(2-hydroxy-5-nitrophenyl)-8-methyl-8-aza-11-oxatriangulenium hexafluorophosphate, MR-69_DAOTA,
8-(3-(N-methylamino)propyl-4,8-diazatriangulenium-4-(4-(trifluoromethyl)phenolate), MR-66_DAOTANH.1,
4-(2-hydroxy-5-(methylsulfonyl)phenyl)-4-aza-8,12-dioxatriangulenium hexafluorophosphate, MR-49.6_ADOTA, and
8-(3-(N-methylamino)propyl-4,8-diazatriangulenium-4-(4-(methylsulfonyl)phenolate), MR-49.6_DAOTANH, are specifically comprised by the present invention.

Optionally, compounds of Formula (I) may be present together with a suitable counter ion, the counter ion may preferably be selected from the group comprising $Cl^-$, $Br^-$, $BF_4^-$, $B(C_6H_6)_4^-$, $PF_6^-$, $HSO_4^-$, $SO_4^{2-}$, TRISPHAT, $CF_3SO_3^-$, and $CH_3SO_3^-$, preferably $Br^-$, $BF_4^-$, $B(C_6H_6)_4^-$, PF$_6^-$, TRISPHAT, CF$_3$SO$_3^-$, and CH$_3$SO$_3^-$, or even more preferably BF$_4^-$, PF$_6^-$, I$^-$, AsF$_6^-$, SbF$_6^-$, ClO$_4^-$, NO$_3^-$, or TRISPHAT. However, other counter ions may according to the present invention also be suitable.

It has been found that by modification of one or more of the groups, $R^1$, $R^2$, $R^3$, $R^4$, $R^5$, $R^6$, $R^7$, $R^8$, $R^9$, NR$^{10}$, $X^1$, or $X^2$, of compound of Formula (I), it is possible to quench photo emission of these compounds compared to their native triangulenium compound. The quenching is taking place by intramolecular photoinduced electron transfer (PET). The PET quenching action of the appendend groups may depend on the presence of analytes interaction with the group. Thus, new responsive compounds of Formula (I) may be obtained.

Compounds of Formula (I) have been found to be photostable as well as chemical stable during use. Compounds of Formula (I) are especially useful when monitoring or determining the concentration of an analyte, e.g. H$^+$ (pH), also at harsh conditions, and show high and long-term stability, when the sample conditions are changed.

In another exemplary embodiment of the invention, compounds of Formula (I) are chemically reactive, and are substituted by at least one reactive group. The reactive group functions as the site of attachment for another moiety, such as a linker, L, a carrier molecule or a solid support, wherein the reactive group chemically reacts with an appropriate reactive or functional group on the linker, carrier molecule or solid support.

In an exemplary embodiment, compounds of Formula (I) further comprise a reactive group, which is selected from an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a photoactivatable group, a reactive platinum complex, a silyl halide, a sulfonyl halide, and a thiol. In a particular embodiment the reactive group is selected from the group consisting of carboxylic acid, succinimidyl ester of a carboxylic acid, hydrazide, amine and a maleimide.

The reactive group may be attached to any appropriate site on compounds of Formula (I).

In this way, compounds of Formula (I) having a reactive group can be attached to a wide variety of linkers, carrier molecules or solid supports that contain or are modified to contain functional groups with suitable reactivity, resulting in chemical attachment of the compounds of Formula (I).

The choice of the reactive group used to attach the compounds of Formula (I) to the linker, conjugated carrier molecule or solid support typically depends on the reactive or functional group on the substance to be conjugated and the type or length of the linkage desired. The types of functional groups typically present on the organic or inorganic substances (biomolecule or non-biomolecule) include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. A single type of reactive site may be available on the substance (typical for polysaccharides or silica), or a variety of sites may occur (e.g., amines, thiols, alcohols, phenols), as is typical for proteins.

Comprised in the present invention is in yet an embodiment, compound of Formula (II)

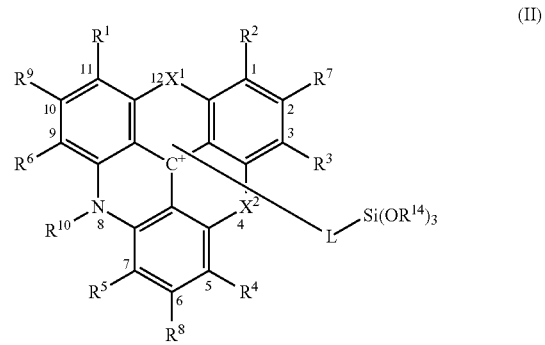

wherein $X^1$ denotes NR$^{11}$, O, S, or C(R$^{11}$)$_2$, or denotes two individual substituted or unsubstituted C$_1$-C$_{24}$-alkoxy groups, which each are linked to the two adjacent carbon atoms, $X^2$ denotes NR$^{12}$, O, S, or C(R$^{12}$)$_2$, or denotes two individual substituted or unsubstituted C$_1$-C$_{24}$-alkoxy groups, which each are linked to the two adjacent carbon atoms, at least one of the subgroups $R^1$, $R^2$, $R^3$, $R^4$, $R^5$, $R^6$, $R^7$, $R^8$, $R^9$, $R^{10}$, $R^{11}$ or $R^{12}$ is attached to a linker L, or $R^{10}$, $R^{11}$ or $R^{12}$ is a linker L, $R^1$, $R^2$, $R^3$, $R^4$, $R^5$, $R^6$, $R^7$, $R^8$, $R^9$, $R^{10}$, $R^{11}$ and $R^{12}$ are independently selected from the group comprising hydrogen, cyano, halogen, hydroxy, nitro, acyl, acylamino, acyloxy, C$_1$-C$_{24}$-alkenyl, C$_1$-C$_{24}$-alkynyl, aryl, C$_1$-C$_{24}$-alkoxy, C$_1$-C$_{24}$-alkylsulfonyl, methylsulfonyl, triflouromethyl, amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, sulfonyl, sulfonyloxy, thioacyl, thiol, thiocarbonyl, C$_1$-C$_{24}$-alkylthio, heteroaryl, cycloalkyl, phenyl, hydroxyphenyl, aminophenyl, amino-C$_1$-C$_{24}$-alkyl, or heterocyclyl, such as a 5- or 6-membered heterocyclyl containing at least one nitrogen or sulphur atom; $R^1$, $R^2$, $R^3$, $R^4$, $R^5$, $R^6$, $R^7$, $R^8$, $R^9$, $R^{10}$, $R^{11}$ and $R^{12}$ optionally being substituted once, twice, or three times with $R^{13}$ group(s), $R^{13}$ is independently selected form the group comprising hydrogen, cyano, halogen, hydroxy, nitro, acyl, acylamino, acyloxy, C$_1$-C$_{24}$-alkyl, C$_1$-C$_{24}$-alkenyl, C$_1$-C$_{24}$-alkynyl, aryl, C$_1$-C$_{24}$-alkoxy, C$_1$-C$_{24}$-alkylsulfonyl, methylsulfonyl, triflouromethyl, amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, sulfonyl, sulfonyloxy, thioacyl, thiol, thiocarbonyl, C$_1$-C$_{24}$-alkylthio, heteroaryl, or a cycloalkyl, $R^{14}$ is independently selected from the group comprising hydrogen, or straight or branched C$_1$-C$_6$-alkyl, alkenyl, or alkynyl, and optionally together with a suitable counter ion, and one or more of the subgroups $R^1$, $R^2$, $R^3$, $R^4$, $R^5$, $R^6$, $R^7$, $R^8$, $R^9$, $R^{10}$, $R^{11}$ or $R^{12}$ is/are a quenching group independently selected from the group comprising phenyl, substituted with one to three groups of $R^{13}$, wherein at least one $R^{13}$ group is hydroxy or a group selected from indole, benzoefuran, naphthalene, or 5- or 6-membered heterocyclyl or C$_1$-C$_6$ alkylene heterocyclyl containing at least one of N, NH, O, or S, said group optionally being substituted one, two, or three times with $R^{13}$ group(s), wherein at least one $R^{13}$ group is hydroxy, and optionally together with a suitable counter ion.

The linker L may be composed of a number of different atoms to attach the silane group —Si(OR$^{14}$)$_3$ to the dye part of the molecule. In particular the linker may be a substituted or unsubstituted $C_1$-$C_{24}$ alkylene, alkenylene, alkynylene group optionally interrupted in the carbon chain with one or more heteroatoms selected from O, S, and NH. In the event the linker is substituted it may be substituted with $R^{13}$ as defined elsewhere herein. In a certain embodiment of the invention the linker is of the general formula:

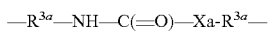

in which $R^{3a}$ and Xa is defined below.

The linker L of the compound with the formula (II) is attached to a silane group Si(OR$^{14}$)$_3$, which may form polymers with itself or with other silanes, notably alkoxysilanes. Examples of suitable alkoxysilanes include

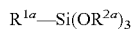          (III)

and

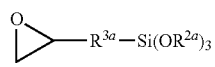          (IV)

wherein $R^{1a}$ represents a straight or branched $C_1$-$C_6$ alkyl or $C_2$-$C_6$ alkenyl, a $C_3$-$C_6$ cycloalkyl, a $C_1$-$C_6$ aminoalkyl, a $C_1$-$C_6$ hydroxyalkyl, a $C_1$-$C_6$ cyanoalkyl, a phenyl, a group of the formula -Ya-(Xa-Ya)$_n$H, wherein Ya independently is selected from straight or branched $C_1$-$C_6$ alkylene, Xa is a hetero atom or group selected among O, S, NH, and n is an integer of 1-5, or $R^{1a}$ represents a $C_1$-$C_6$ alkyl substituted with a group Za, wherein Za independently is selected form the group comprising hydrogen, cyano, halogen, hydroxy, nitro, acyl, acylamino, acyloxy, $C_1$-$C_{24}$-alkyl, $C_1$-$C_{24}$-haloalkyl, $C_1$-$C_{24}$-alkenyl, $C_1$-$C_{24}$-alkynyl, aryl, $C_1$-$C_{24}$-alkoxy, $C_1$-$C_{24}$-alkylsulfonyl, amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, sulfonyl, sulfonyloxy, thioacyl, thiol, thiocarbonyl, $C_1$-$C_{24}$-alkylthio, heteroaryl, or a cycloalkyl;

$R^{2a}$ independently represents a straight or branched $C_1$-$C_6$ alkyl; and $R^{3a}$ represents a linker chosen from a group of the formula

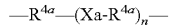

wherein $R^{4a}$ independently is selected from straight or branched $C_1$-$C_6$ alkylene, $C_1$-$C_{24}$-haloalkylene, Xa is a hetero atom or group selected among O, S, NH, and n is an integer of 0-12.

In a certain embodiment, the linker may be attached to the substrate by a lipophilic group such as an alkyl group. The alkyl group may comprise 1 to 24 carbon atoms, preferably 6-18 carbon atoms, more preferably 9-15 carbon atoms. The alkyl group may be branched or unbranched, and optionally be substituted.

In another embodiment, the linker is covalent bound to the silane-group, the linker preferably being a primary alkyleneamine.

Thus, in a certain embodiment, a sol-gel based matrix is prepared from the compounds of Formula (II), (III), and (IV). In a first step a first sol-gel component may be prepared by polymerisation of the compound according to formula (III) in the presence of a an acid catalyst. In a second step a second sol-gel component may be prepared by polymerisation of the compound according to formula (IV) in the presence of a Lewis acid catalyst. The compound according to formula (II) may in the first or/and the second step be admixed to obtain a polymer with added fluorescent dye. The addition of the compound according to formula (II) may be made prior to the polymerisation or during the polymerisation. In a third step the first sol-gel component and the second sol-gel component are mixed for the preparation of a sol-gel based matrix.

In yet a further embodiment, compounds of Formula (II) wherein at least one of the following subgroups, $R^{10}$, $R^{11}$ and $R^{12}$, is a quenching group independently selected from the group comprising phenol, benzoefuran, indole, pyrrolidine, pyrrole, thiolane, thiophene, imidazolidine, pyrazolidine, imidazole, pyrazole, oxazolidine, isoxazolidine, oxazole, isoxazole, thiazolidine, isothiazolidine, thiazole, isothiazole, dithiolane, triazoles, furazan, oxadiazole, thiadiazole, dithiazole, tetrazole, piperidine, pyridine, thiane, thiopyran, piperazine, diazines, oxazine, thiomorpholine, thiazine, dithiane, dithiine, triazine, or tetrazine may optionally be substituted one, two, three times with $R^{13}$ group(s), are comprised by the present invention. In particular, one or more of the hydrogen atoms attach to the phenyl group may be substituted one, two or three times with a $R^{13}$ groupIn another embodiment, compounds of Formula (II) wherein $R^{10}$, $R^{11}$ and $R^{12}$ is a quenching group independently selected from the group comprising 2-phenol, 3-phenol, 4-phenol, hydroxy-indole, hydroxy-pyrrolidine, hydroxy-pyrrole, hydroxy-thiophene, wherein one or more of the hydrogen atoms attached to the aryl group may optionally be substituted one, two, three times with $R^{13}$ group(s), are also comprised by the present invention. In particular, one or more of the hydrogen atoms attached to the phenyl group may be substituted one, two or three times with $R^{13}$ group(s).

In yet a further embodiment, N-(2-hydroxy-5-(trifluoromethyl)phenyl)-N'-(6-aza-4-oxa-5-oxo-9-trimethoxysilyl-nonan)-diazaoxatriangulenium hexafluorophosphat, 6, and N-(methyl)-N'-(6-aza-4-oxa-5-oxo-9-trimethoxysilyl-nonan)-1,13-dimethoxyquinacridinium tetrafluoroborate, 7, 8-(1-methyl-1-propyl-3-(3-(triethoxysilyl)propyl)urea)-4,8-diazatriangulenium-4-(4-(trifluoromethyl)phenolate) I1C, and 8-(1-methyl-1-propyl-3-(3-(triethoxysilyl)propyl)urea)-4,8-diazatriangulenium-4-(4-(methylsulfonyl)phenolate) I2C are specifically comprised by the present invention.

In another embodiment, compounds of Formula (I) or compounds of Formula (II) may be conjugated to a carrier molecule, the carrier molecule preferably being selected from the group comprising an amino acid, a peptide, a protein, a polysaccharide, a nucleoside, a nucleotide, an oligonucleotide, a nucleic acid polymer, a drug, a hormone, a lipid, a lipid assembly, a synthetic polymer, a polymeric microparticle, a biological cell, or a virus. Other carrier molecules may also be suitable.

By conjugating compounds of Formula (I) or compounds of Formula (II) to a carrier molecule, it may be possible to monitoring or determining the concentrations of an analyte having a specific activity to the conjugated compound. The conjugated compound may also due to the conjugation be stabilised against harsh conditions.

In another embodiment, compounds of Formula (I) or compounds of Formula (II) may be attached to a solid support, the solid support is preferably selected from the group comprising a microfluidic chip, a silicon chip, a microscope slide, a microplate well, cuvette, silica gels, polymeric membranes, particles, derivatized plastic films, glass beads, cotton, plastic beads, alumina gels, polysaccharides, polyvinylchloride, polypropylene, polyethylene, nylon, latex bead, magnetic bead, paramagnetic bead, or superparamagnetic bead, sepharose, poly(acrylate), polystyrene, poly(acrylamide), polyol, agarose, agar, cellulose, dextran, starch, FICOLL, heparin, glycogen, amylopectin, mannan, inulin, nitrocellulose, starch, or a sol-gel based matrix. Other carrier molecules or solid supports may also be suitable.

This is advantageous as compounds of Formula (I) or compounds of Formula (II) may be further stabilised towards changing process conditions, or the like. Thus, compounds of Formula (I) or compounds of Formula (II) may e.g. exhibit long-term stability and readability.

Further, compounds of Formula (I) or compounds of Formula (II) of the present invention are suitable for use in a method for monitoring or determining the concentration of an analyte, the method comprising:

(a) contacting a sample with a compound of Formula (I) or a compound of Formula (II), to form a contacted sample;

(b) illuminating the contacted sample to form an illuminated sample; and (c) detecting the fluorescent emissions from the illuminated sample, wherein the fluorescent emissions are used to monitor or determine the concentration of the analyte.

According to the present invention, the compounds of Formula (I) may be modified and optimised such that these compounds can sense the presence of different analytes, and the amount or concentration thereof.

Thus, in one embodiment of the present invent, the analyte to be determined or monitored is selected from the group comprising $H^+$(pH), $Na^+$, $K^+$, $Ca^{2+}$, $O_2$, $CO_2$, $H_2O_2$, metal ions, metabolites, and other suitable analytes, preferably $H^+$(pH), $O_2$, and $CO_2$.

Each of the described embodiments of the present invention is to be construed as disclosing the present invention either individually or in combination with the other embodiments.

BRIEF DESCRIPTION OF THE DRAWINGS

FIG. 1a1 shows the absorption spectra of 3a in a PBS solution at low pH and high pH. The arrow indicates the change from pH~1 to pH~11.

FIG. 1a2 shows the absorption spectra (dashed line) and emission spectra in the on- and off-state (full line) of 3a in a PBS solution. The arrow indicates the change from pH~1 to pH~11.

FIG. 1b1 shows the absorption spectra (dashed line) and emission spectra (full line) of 4g in a MeCN solution.

FIG. 1b2 shows the absorption spectra (dashed line) and emission spectra (full line) in the on- and off-state 4g in a MeCN solution. The arrow indicates the change from pH~1 to pH~11.

FIG. 2a1 shows the absorption spectra (dashed line) of 4g and the emission spectra of 4g of a sol-gel matrix.

FIG. 2a2 shows the emission spectra (full line) in the on- and off-state of 4g sensor molecules in the on- and off-state in sol-gel matrices. The dashed line shows the matrix background emission. The arrow indicates the change from pH~11 to pH~1.

DETAILED DESCRIPTION OF THE INVENTION

Figure 1C:
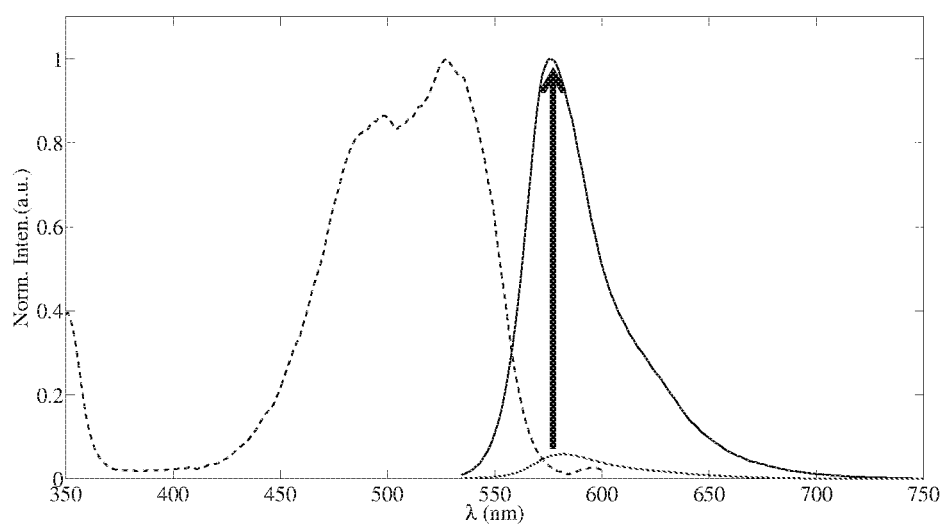
FIG. 1c shows the absorption spectra (dashed line) and emission spectra (full line) in the on- and off-state of 5 in a MeCN solution. The arrow indicates the change from pH~1 to pH~11.

In the following, the present invention is described in more detail. All individual features and details can be individually applied to each embodiment and aspect of the compounds of Formula (I), its methods and its use.

Preparation of Compounds of Formula (I)

The synthesis of the new fluorescent dyes of compounds of Formula (I) is based on an approach adapted from the published procedures,[10A,11A] the basic synthetic route is outlined in Reaction scheme 1.

Reaction Scheme 1. Basic synthetic route to responsive fluorescent aza-triangulenium dyes.

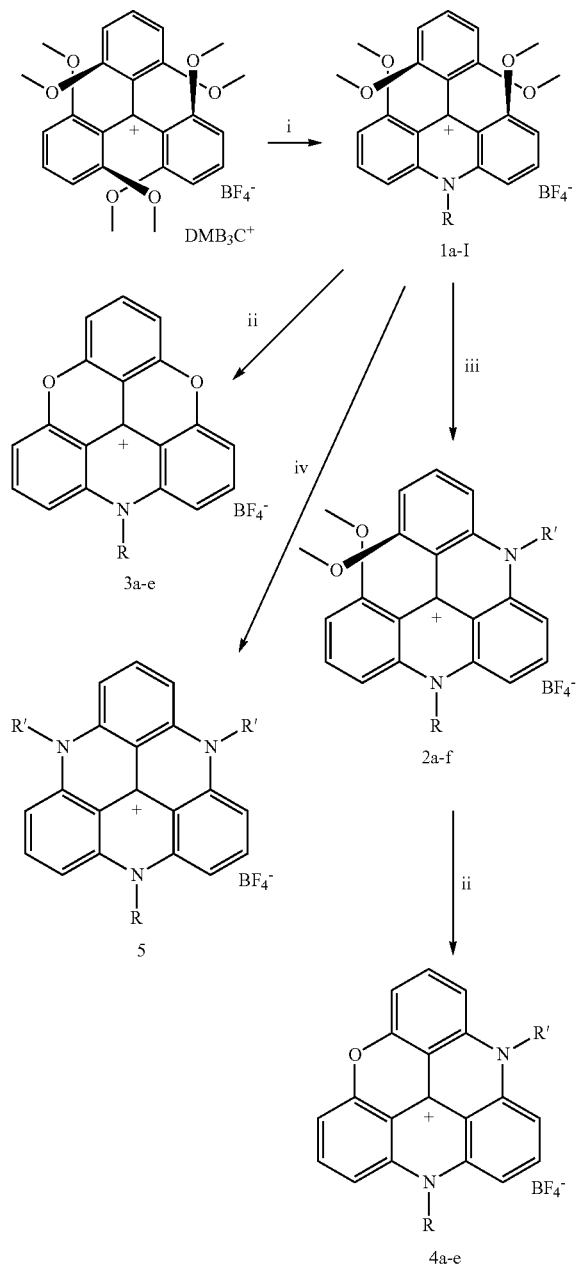

i) alkylamine, arylamine.
ii) molten pyridinium chloride, 180-220° C., 15-45 minutes.
iii) amine, NMP, 140° C., 45-180 minutes.
iv) alkylamine, arylamine.

The triphenylmethylium starting material $DMB_3C^+$ is reacted with a primary amine in a nucleophilic aromatic substitution $S_NAr$ reaction, replacing two methoxy groups and forming and aza-bridge between two of the three phenyl groups in the starting material. The resulting compounds 1a-5 are all 9-substituted, 10-phenyl tetramethoxy-acridinium ions ($TMAcr^+$).

Thermolytic ether cleavage using pyridinium chloride results in formation of two oxa-bridges and complete planarization of the structure, forming azadioxatriangulenium ($ADOTA^+$) salts 3 from the respective tetramethoxy-acridinium compounds 1. The tetramethoxy-acridinium ions 1 may undergo a second $S_NAr$ under slightly harsher reaction conditions (See scheme 1) forming a second aza-bridge making dimethoxyquinacridinium ($DMQA^+$) salts 2. These can be treated with molten pyridinium chloride, forming an oxa-bridge and making the diazaoxatriangulenium ($DAOTA^+$) salts 4. Finally the tetramethoxy-acridinium ions may be reacted with primary amines under harsh reaction conditions, where two $S_NAr$ reactions take place forming the triaza-triangulenium ($TATA^+$) salts 5.

Based on the above general approach, different compounds of Formula (I) having substitutions at $NR^{10}$, $X^1$, and $X^2$ as outlined in Reaction scheme 2 and 3 were designed and prepared.

Reaction scheme 2: Design of responsive fluorescent azaoxa-triangulenium dyes.

1st generation

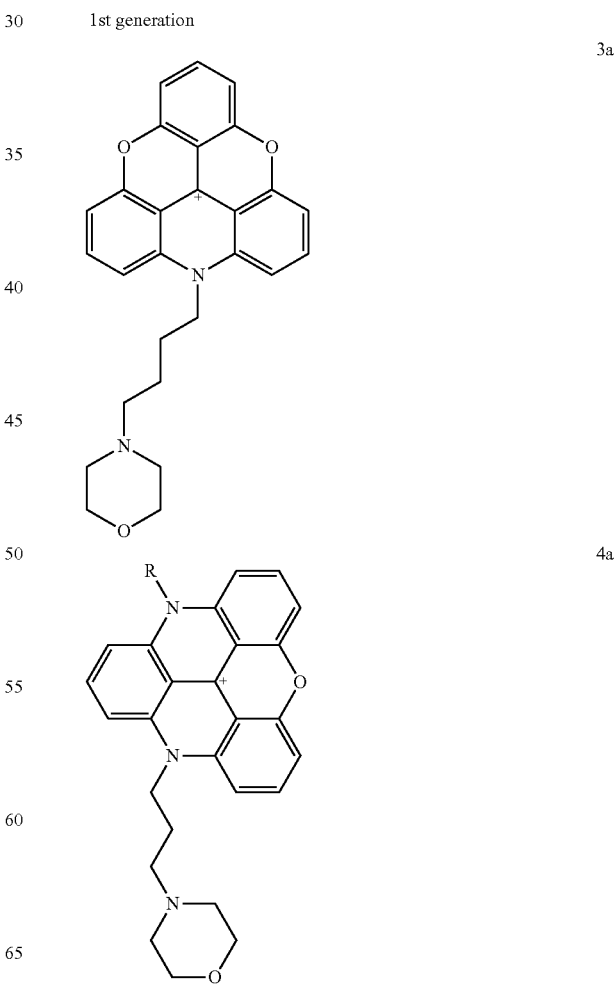

2nd generation
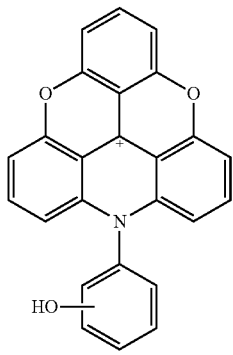
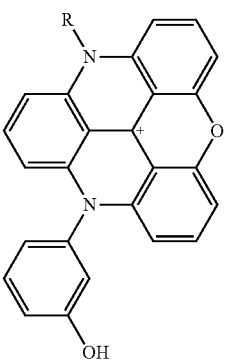
3rd generation
4c
3b-d
3e
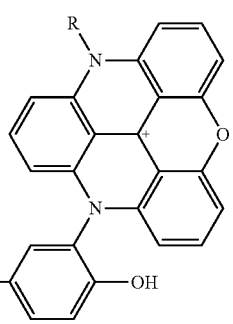
4f
4e
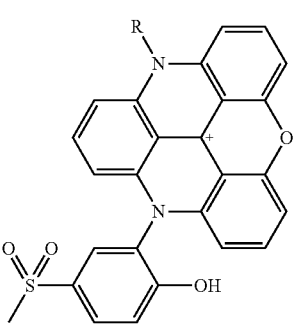
4g
Reaction Scheme 3 shows the synthetic pathway to pH responsive azadioxatriangulenium ADOTA$^+$ and diazaoxatriangulenium DAOTA$^+$ dyes comprising ortho-, meta- and para-phenol substituted ADOTA$^+$ and DAOTA$^+$ derivatives.

Reaction scheme 3. Synthetic pathway to responsive ADOTA and DAOTA comprising substituted phenol derivatives.
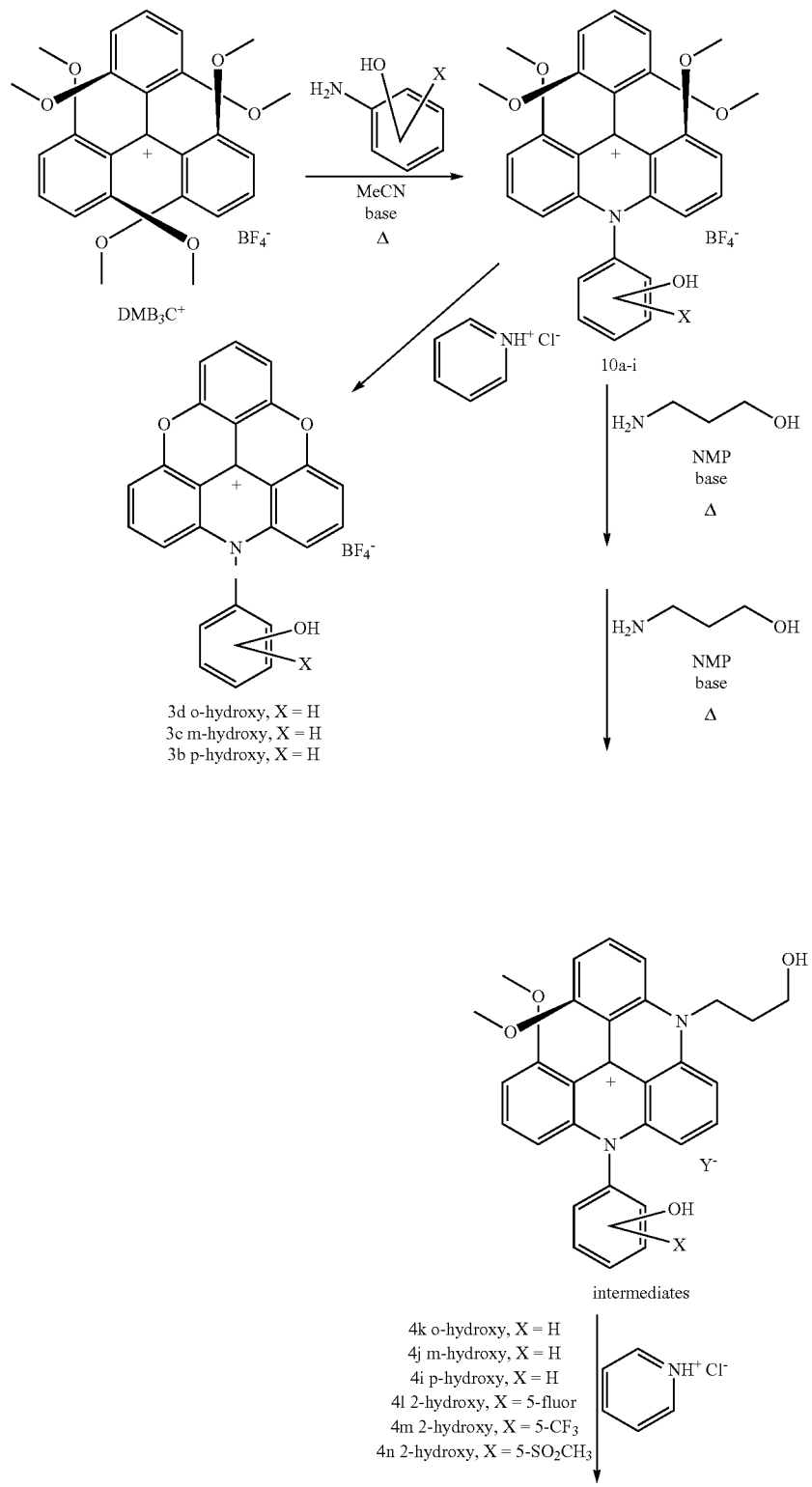

-continued

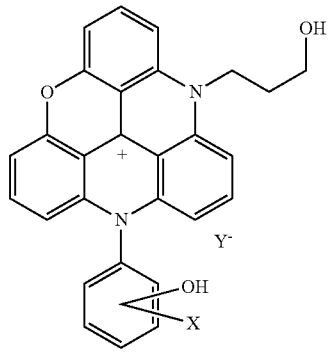

Definitions

Unless defined otherwise, all technical and scientific terms used herein have the same meaning as commonly understood by one of ordinary skill in the art to which this invention is related. The following terms are defined for purposes of the invention as described herein.

"Alkyl" refers to monovalent saturated aliphatic hydrocarbyl groups.

The term "$C_1$-$C_{24}$-alkyl", unless otherwise indicated, denotes an alkyl group with 1 to 24 carbon atoms. The term "Alkyl" when used herein refers to a $C_1$-$C_{24}$-alkyl.

In one particular embodiment suitable alkyl groups include straight or branched $C_1$-$C_6$-alkyl, which, unless otherwise indicated, denotes an alkyl group with 1 to 6 carbon atoms. Such suitable $C_1$-$C_6$-alkyl groups include, for example, methyl, ethyl, propyl, e.g. n-propyl and isopropyl, butyl, e.g. n-butyl, iso-butyl, sec-butyl and tert-butyl, pentyl, e.g. n-pentyl, and hexyl (e.g. n-hexyl). for example, methyl, ethyl, propyl, e.g. n-propyl and isopropyl, butyl, e.g. n-butyl, iso-butyl, sec-butyl and tert-butyl, pentyl, e.g. n-pentyl, and hexyl (e.g. n-hexyl).

In one particular embodiment suitable alkyl groups include linear $C_1$-$C_{24}$-alkyl, which, unless otherwise indicated, refers to straight alkyl chains of 1, 2, 3, 4, 5, 6, 7, 8, 9, 10, 11, 12, 13, 14, 15, 16, 17, 18, 19, 20, 21, 22, 23, or 24 carbon atoms.

"Alkenyl" refers to aliphatic hydrocarbyl groups having at least one double bond.

The term "$C_2$-$C_{24}$-alkenyl", unless otherwise indicated, may be interpreted similarly to the term "alkyl". Preferably, the alkenyl is a $C_2$-$C_6$ alkenyl with 2 to 6 carbon atoms. Suitable alkenyl groups include, for example, ethenyl, propenyl, 1-butenyl, and 2-butenyl.

"Alkynyl" refers to aliphatic hydrocarbyl groups having at least one double bond.

The term "$C_2$-$C_{24}$-alkynyl", unless otherwise indicated, may be interpreted similarly to the term "alkyl". Alkenyl groups contain at least 1 triple bond. Preferably, the alkynyl is a $C_2$-$C_6$ alkynyl with 2 to 6 carbon atoms.

The term "halogen", unless otherwise indicated, denotes fluorine (F), chlorine (Cl), bromine (Br) and iodine (I), preferably F, Cl or Br. In a certain embodiment of the invention, the compounds of Formula (I) and compounds of Formula (I) may be substituted with one, two, three, four, five, six or even more halogens, preferable Cl or Br, more preferable Cl.

"$C_1$-$C_{24}$-alkoxy" refers to the group —O—$C_1$-$C_{24}$-alkyl wherein $C_1$-$C_{24}$-lkyl is defined herein. Alkoxy includes, by way of example, methoxy, ethoxy, n-propoxy, isopropoxy, n-butoxy, f-butoxy, sec-butoxy, and n-pentoxy.

"Acyl" refers to the groups H—C(O)—, alkyl-C(O)—, alkenyl-C(O)—, alkynyl-C(O)—, cycloalkyl-C(O)—, cycloalkenyl-C(O)—, aryl-C(O)—, heteroaryl-C(O)—, and heterocyclic-C(O)—, wherein alkyl, alkenyl, alkynyl, cycloalkyl, cycloalkenyl, aryl, heteroaryl, and heterocyclic are as defined herein. Acyl includes the "acetyl" group $CH_3C(O)$—.

"Acylamino" refers to the groups —NRC(O)alkyl, —NRC(O)cycloalkyl, —NRC(O)cycloalkenyl, —NRC(O)alkenyl, —NRC(O)alkynyl, —NRC(O)aryl, —NRC(O)heteroaryl, and —NRC(O)heterocyclic, wherein R is hydrogen or alkyl and wherein alkyl, alkenyl, alkynyl, cycloalkyl, cycloalkenyl, aryl, heteroaryl, and heterocyclic are as defined herein.

"Acyloxy" refers to the groups alkyl-C(O)O—, alkenyl-C(O)O—, alkynyl-C(O)O—, aryl-C(O)O—, cycloalkyl-C(O)O—, cycloalkenyl-C(O)O—, heteroaryl-C(O)O—, and heterocyclic-C(O)O—, wherein alkyl, alkenyl, alkynyl, cycloalkyl, cycloalkenyl, aryl, heteroaryl, and heterocyclic are as defined herein.

"Aminocarbonyl" refers to the group —C(O)NR$^{13}$R$^{13}$, where R$^{13}$ is as defined herein, optionally the two R$^{13}$ groups may be joined together with the nitrogen bound thereto to form a heterocyclic group.

"Aminothiocarbonyl" refers to the group —C(S)NR$^{13}$R$^{13}$, where R$^{13}$ is as defined herein, optionally the two R$^{13}$ groups may be joined together with the nitrogen bound thereto to form a heterocyclic group.

"Aminocarbonylamino" refers to the group —NRC(O)NR$^{13}$R$^{13}$, where R$^{13}$ is as defined herein, optionally the two R$^{13}$ groups may be joined together with the nitrogen bound thereto to form a heterocyclic group.

"Aminothiocarbonylamino" refers to the group —NR$^{13}$C(S) NR$^{13}$R$^{13}$, where R$^{13}$ is as defined herein, optionally the two R$^{13}$ groups may be joined together with the nitrogen bound thereto to form a heterocyclic group.

"Aminocarbonyloxy" refers to the group —O—C(O)NR$^{13}$R$^{13}$, where R$^{13}$ is as defined herein, optionally the two R$^{13}$ groups may be joined together with the nitrogen bound thereto to form a heterocyclic group.

"Aminosulfonyl" refers to the group —SO$_2$NR$^{13}$R$^{13}$, where R$^{13}$ is as defined herein, optionally the two R$^{13}$ groups may be joined together with the nitrogen bound thereto to form a heterocyclic group.

"Aminosulfonyloxy" refers to the group —O—SO$_2$NR$^{13}$R$^{13}$, where R$^{13}$ is as defined herein, optionally the two R$^{13}$ groups may be joined together with the nitrogen bound thereto to form a heterocyclic group.

"Aminosulfonylamino" refers to the group —NR—SO$_2$NR$^{13}$R$^{13}$, where R$^{13}$ is as defined herein, optionally the two R$^{13}$ groups may be joined together with the nitrogen bound thereto to form a heterocyclic group.

"Amidino" refers to the group —C(=NR$^{13}$)R$^{13}$R$^{13}$ where R$^{13}$ is as defined herein, optionally two R$^{13}$ groups may be joined together with the nitrogen bound thereto to form a heterocyclic group "Aryl" refers to a monovalent aromatic carbocyclic group of from 5 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Carboxyl" or "carboxy" refers to —COOH.

"Carboxyl ester" or "carboxy ester" refers to the groups —C(O)O— alkyl, —C(O)O-alkenyl, —C(O)O-alkynyl, —C(O)O-aryl, —C(O)O-cycloalkyl, —C(O)O-cycloalkenyl, —C(O)O-heteroaryl, and —C(O)O-heterocyclic, wherein alkyl, alkenyl, alkynyl, cycloalkyl, cycloalkenyl, aryl, heteroaryl, and heterocyclic are as defined herein.

"(Carboxyl ester)amino" refers to the group —NR—C(O)O-alkyl, —NR—C(O)O-alkenyl, —NR—C(O)O-alkynyl, —NR—C(O)O-aryl, —NR—C(O)O-cycloalkyl, —NR—C(O)O-cycloalkenyl, —NR—C(O)O-heteroaryl, and —NR—C(O)O-heterocyclic, wherein alkyl, alkenyl, alkynyl, cycloalkyl, cycloalkenyl, aryl, heteroaryl, and heterocyclic are as defined herein.

"(Carboxyl ester)oxy" refers to the group —O—C(O)O-alkyl, s-O—C(O)O-alkenyl, —O—C(O)O-alkynyl, —O—C(O)O-aryl, —O—C(O)O-cycloalkyl, —O—C(O)O-cycloalkenyl, —O—C(O)O-heteroaryl, and O—C(O)O-heterocyclic, wherein alkyl, alkenyl, alkynyl, cycloalkyl, cycloalkenyl, aryl, heteroaryl, and heterocyclic are as defined herein.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C<ring unsaturation and preferably from 1 to 2 sites of >C=C<ring unsaturation.

"Heteroaryl" refers to an aromatic group of from 5 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Preferred heteroaryls include pyridinyl, pyrrolyl, indolyl, thiophenyl, and furanyl.

"Heterocycle" or "heterocyclic" or "heterocycloalkyl" or "heterocyclyl" refers to a saturated or unsaturated group having a single ring or multiple condensed rings, including fused bridged systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetra hyd roisoquinoline, 4,5,6,7-tetra hyd robenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"5- or 6-membered heterocyclyl containing at least one nitrogen or sulphur atom" include, but are not limited to, benzoefuran, indole, pyrrolidine, pyrrole, thiolane, thiophene, imidazolidine, pyrazolidine, imidazole, pyrazole, oxazolidine, isoxazolidine, oxazole, isoxazole, thiazolidine, isothiazolidine, thiazole, isothiazole, dithiolane, triazoles, furazan, oxadiazole, thiadiazole, dithiazole, tetrazole, piperidine, pyridine, thiane, thiopyran, piperazine, diazines, morpholine, oxazine, thiomorpholine, thiazine, dithiane, dithiine, triazine, or tetrazine.

"Sulfonyl" refers to the divalent group —S(O)$_2$—.

"Alkylsulfonyl" refers to the group —S(O)$_2$-alkyl wherein alkyl is as defined herein. Preferably, the alkyl group is a small group having less than 6 carbon atoms, more preferable the alkyl group is methyl or ethyl.

"Sulfonyloxy" refers to the group —OSO$_2$-alkyl, —OSO$_2$-alkenyl —OSO$_2$— cycloalkyl, —OSO$_2$-cycloalkenyl, —OSO$_2$-aryl, —OSO$_2$-heteroaryl, and —OSO$_2$-heterocyclic, wherein alkyl, alkenyl, alkynyl, cycloalkyl, cycloalkenyl, aryl, heteroaryl, and heterocyclic are as defined herein.

"Thioacyl" refers to the groups H—C(S)—, alkyl-C(S)—, alkenyl-C(S)—, alkynyl-C(S)—, cycloalkyl-C(S)—, cycloalkenyl-C(S)—, aryl-C(S)—, heteroaryl-C(S)—, and heterocyclic-C(S)—, wherein alkyl, alkenyl, alkynyl, cycloalkyl, cycloalkenyl, aryl, heteroaryl, and heterocyclic are as defined herein.

"Thiol" refers to the group —SH.

"Thiocarbonyl" refers to the divalent group —C(S)— which is equivalent to —C(=S)—.

"Alkylthio" refers to the group —S-alkyl wherein alkyl is as defined herein.

It is understood that the above definitions are not intended to include impermissible substitution patterns (e.g., methyl substituted with 5 fluoro groups). Such impermissible substitution patterns are well known to the skilled person.

The term "carrier molecule" as used herein refers to a biological or a non-biological component that is or becomes attached to a compound of Formula (I) of the present invention. In a preferred embodiment of the present invention, such components include, but are not limited to, an amino acid, a peptide, a protein, a polysaccharide, a nucleoside, a nucleotide, an oligonucleotide, a nucleic acid, a drug, a hormone, a lipid, a lipid assembly, a synthetic polymer, a polymeric microparticle, a biological cell, a virus and combinations thereof.

Compounds of Formula (I) or compounds of Formula (II) may be conjugated to a carrier molecule or attached to a solid support by well established methods known to the skilled person.

Conjugates of carrier molecules, e.g., drugs, peptides, toxins, nucleotides, phospholipids, proteins and other organic molecules including the compounds of Formula (I) or compounds of Formula (II) of the present invention, are generally prepared by means well recognized in the art (Haugland, MOLECULAR PROBES HANDBOOK, supra, (2002)). Preferably, conjugation forming a covalent bond consists of simply mixing the reactive compounds of the present invention in a suitable solvent in which both the reactive compound and the substance to be conjugated are soluble. The reaction preferably proceeds spontaneously without added reagents at room temperature or below. For those reactive compounds that are photoactivated, conjugation is facilitated by illumination of the reaction mixture to activate the reactive compound. Chemical modification of water-insoluble substances, so that a desired compound-conjugate may be prepared, is preferably performed in an aprotic solvent such as dimethylformamide, dimethylsulfoxide, acetone, ethyl acetate, toluene, or chloroform. Similar modification of water-soluble materials is readily accomplished through the use of the instant reactive compounds to make them more readily soluble in organic solvents.

The term "solid support" as used herein refers to a matrix or medium that is substantially insoluble in liquid phases and capable of binding a molecule or particle of interest. Solid supports of the current invention include semi-solid supports and are not limited to a specific type of support.

Useful solid supports include solid and semisolid matrixes, such as sol-gels, aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like.

Compounds of Formula (I) or compounds of Formula (II) may be attached to a solid support material by well-established methods known to the skilled person.

In one particular embodiment, compounds of Formula (I) may be attached to a sol-gel based matrix.

Assays using fluorescent compounds of Formula (I) or compounds of Formula (II) involve contacting a sample with a compound of Formula (I) or compounds of Formula (II) and measuring the fluorescence. The presence of an analyte that interacts with the compound of Formula (I) may alter the fluorescence of the compound of Formula (I) in many different ways. Essentially any change in fluorescence caused by the analyte may be used to determine the presence of the analyte and, optionally the concentration of the analyte, in the sample.

The change may take one or more of several forms, including a change in the intensity of the fluorescence and/or quantum yield and/or in fluorescent lifetime. These changes may be either in the positive or negative direction and may be of a range of magnitudes, which preferably will be detectable as described below.

A change in quantum yield and/or fluorescent lifetime caused by an analyte may be used as the basis for detecting the presence of an analyte in a sample and may optionally be used to determine the concentration of the analyte. A range of changes are possible in the subject invention.

The presence of an analyte in a sample is detected by contacting the sample with a compound of Formula (I) or compounds of Formula (II) that is sensitive to the presence of the analyte. The fluorescence of the solution is then determined using a suitable device, preferably a spectrofluorometer. Optionally, the fluorescence of the solution may be compared against a set of standard solutions containing known quantities of the analyte or reference dyes. Comparison to standards may be used to calculate the concentration of the analyte, i.e. the analyte. The analyte may be essentially any substance described above. The concentration of the analyte may change over time and the fluorescent signal may serve to monitor those changes. For example, the particular form of the analyte that interacts with compound of Formula (I) or compounds of Formula (II) may be produced or consumed by a reaction occurring in the solution, in which case the fluorescence signal may be used to monitor reaction kinetics.

Examples

Quenching of Compounds of Formula (I), in Solution

Absorption and emission spectrum of the prepared trianguelnium compounds of Formula (I) were measured and their photophysical properties are compiled in table 2.

TABLE 2

Photophysical properties of the pH-responsive fluorescent azaoxa-trianguelnium dyes.

| Compound | pK$_a$ | $\lambda_{max}$ | $\lambda_{em}$ | $\phi_{fl}$ | $\phi_{fl}$ | I$_{on}$/I$_o$ |
|---|---|---|---|---|---|---|
| ADOTA$^+$ subgroup | | | | | | |
| 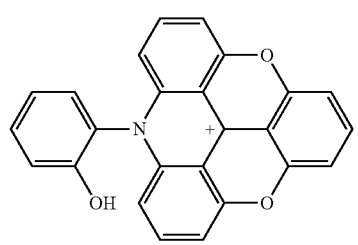<br>3b | 6.9 | 541 | 558 | 8% | >0.5% | ~50 |

TABLE 2-continued

Photophysical properties of the pH-responsive fluorescent azaoxa-trianguelnium dyes.

| Compound | pK$_a$ | λ$_{max}$ | λ$_{em}$ | φ$_{fl}$ | φ$_{fl}$ | I$_{on}$/I$_o$ |
|---|---|---|---|---|---|---|
| 3c | 7.3 | 540 | 558 | 8% | >0.5% | ~50 |
| 3d | 8.3 | 540 | 563 | 2% | >0.5% | ~50 |

DAOTA$^+$ subgroup

| Compound | pK$_a$ | λ$_{max}$ | λ$_{em}$ | φ$_{fl}$ | φ$_{fl}$ | I$_{on}$/I$_o$ |
|---|---|---|---|---|---|---|
| 4b | 9-10 | 560 | 590 | — | — | ~50 |
| 4f |  | 557 | 590 | — | — |  |
| 4g | 3.4 | 557 | 590 | 26% | 6% | ~100 |

TABLE 2-continued

Photophysical properties of the pH-responsive fluorescent azaoxa-trianguelnium dyes.

| Compound | pK$_a$ | λ$_{max}$ | λ$_{em}$ | φ$_{fl}$ | φ$_{fl}$ | I$_{on}$/I$_o$ |
|---|---|---|---|---|---|---|
| 4h | 6.5 | 557 | 590 | — | — | ~50 |

TATA$^+$ subgroup

| | | 540 | 580 | — | — | — |
|---|---|---|---|---|---|---|
| 5 | | | | | | | pK$_a$ is −log$_{10}$ of the acid dissociation constant, K$_a$, and is a quantitative measure of the strength of an acid in solution. λ$_{max}$ denotes the wavelength wherein maximum absorption is obtained. λ$_{em}$ denotes the wavelength wherein maximum emission is obtained. φ$_{fl-on}$ and φ$_{fl-off}$ are the fluorescence quantum yields, wherein the responsive fluorescent compounds are in their on-state (not quenched) and off-state (quenched), respectively. I$_{on}$/I$_{off}$ is the ratio between φ$_{fl-on}$ and φ$_{fl-off}$.

Table 2 shows that quenching can be found for all tested compounds of Formula (I), belonging to the ADOTA$^+$, DAOTA$^+$, and TATA$^+$ system. The response in fluorescence intensity/excited state lifetime is in all cases triggered by the protonation-deprotonation of the heteroatom of the electron donor. Thus, protonation inhibits electrontransfer.

It is found that compounds of Formula (I) substituted with amines, and in particular morpholine, may be used as a responsive PET-quenching molecule, as these compounds can quench the ADOTA$^+$ system. Further, it is found that compounds of Formula (I) substituted with aniline electron donors also may be used as a responsive PET-quenching molecule, e.g. in the DAOTA$^+$ system.

Thus, it has been shown that amine and aniline electron donors can quench the fluorescence of DMQA$^+$, ADOTA$^+$ and DAOTA$^+$ systems.

Furthermore, it is found that compounds of Formula (I) substituted with phenol as electron donors and/or derivatives thereof—as a responsive PET-quenching molecule—may be used, as these compounds can quench the fluorescence of the ADOTA$^+$, DAOTA$^+$ and TATA$^+$ systems effectively. The ADOTA$^+$ system comprising unsubstituted phenol may yield a system with a pK$_a$ of up to 8.3. Electron withdrawing substitutents may lower the pK$_a$ to 3.0.

3b, 3c, and 3d (ADOTA$^+$ system) were found not to suffer from on-state PET-quenching and yield excellent spectral and on/off ratio response. Thus, it is observed that use of a phenol (hydroxyl-phenyl) as PET-quencher for e.g. the ADOTA$^+$ systems may be a highly effective quencher.

The pK$_a$ of the disclosed phenol PET-quenchers are readily tunable. By substituting phenol in the DAOTA$^+$ system with appropriate substituents such as fluoro 4l, trifluoromethyl 4m, or methylsulfonyl 4n, the pK of the DAOTA$^+$ system may be changed. Thus, it is possible to synthesize pH-probes with pK$_a$ values spanning the whole pH-range.

The above data shows that modified electron donor systems, such as amines, anilines and phenolates, can quench systems of fluorescent dyes of conpounds of Formula (I) effectively. The pK$_a$ of the responsive fluorescent dyes of compound of Formula (I) may be tailored using different substitutents on the electron donor system. Thereby, it may be possible to span a wide pH-range.

Thus, PET-quenching of compounds of Formula (I) may be ideal for generating pH-responsive molecules. Further, addition of a second functionalized subgroup to compounds of Formula (I) may be ideal for anchoring the compound of Formula (I) to a linker (L), a conjugate or a solid support material, the linker L being e.g. attached to a silane group, such as Si(OR$^{14}$)$_3$.

The new fluorescent compounds of Formula (I) may be designed to be sensible towards other analytes. Thus, by modifying one or more of $R^1$, $R^2$, $R^3$, $R^4$, $R^5$, $R^6$, $R^7$, $R^8$, $R^9$, $R^{10}$, $R^{11}$ or $R^{12}$ subgroups, it will be possible to obtain fluorescent compounds of Formula (I), which are sentisive towards different analytes, such as, $H^+$(pH), $O_2$, $CO_2$, $H_2O_2$, $Na^+$, $K^+$, $Ca^{2+}$, metal ions, or metabolites.

Figure 2B:
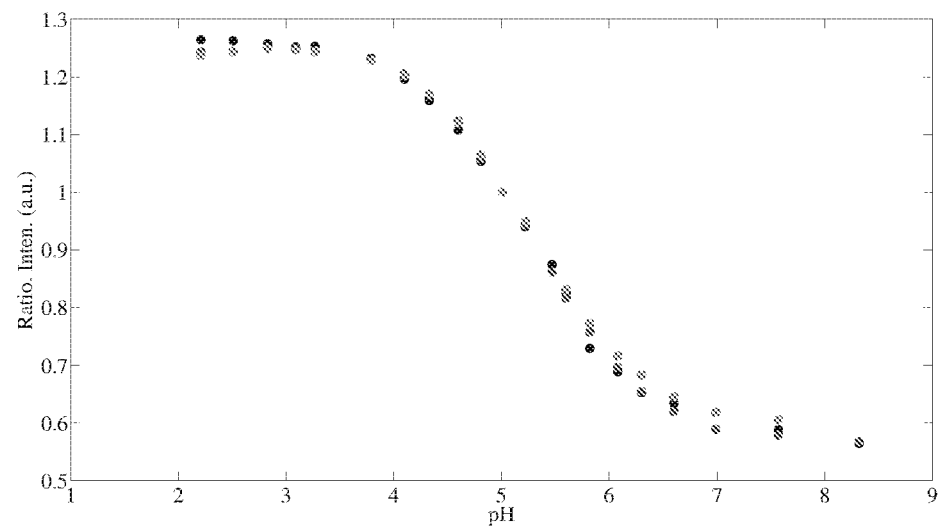
FIG. 2b shows the ratiometric readout (titration curve) of 4g in a SOL GEL matrix in PBS at different pH values for three spots.

FIG. 1a2 shows the emission spectra of 3a in a PBS solution at various pH-values. Thus, it is evident that pH can be determined reliably from 3 to 10, using the ratiometric principle. If the concentration is known, intensity based measurements can also be used to determine pH.

Photophysics in the Sol-Gel Matrix

When compounds of Formula (I) or compounds of Formula (II) are attached to e.g. a linker this may affect some of the properties of the responsive compounds of Formula (I) or compounds of Formula (II). Thus, e.g. the characteristics of the fluorescent dye of compounds of Fomula (I) or compounds of Formula (II) may change significantly, when going from freely diffusing fluorescent dyes in solution to fluorescent dyes attached to a linker, a carrier-molecule or a solid support, e.g. in a semi-permeable sol-gel matrix. Therefore, an experiment was designed to test the fluorescent characteristics for the compounds of formula (I) or (II) in a free and a bound state.

The linker, carrier molecule, or solid support may have another polarity than water, which then may change the $pK_a$ of the fluorescent systems. As the $pK_a$ can be tuned, testing of a few different derivatives may be used to describe the microenvironment, which the attached compounds of Formula (I) or compounds of Formula (II) experience. This allows for designing a sensor, which is responsive in a targeted pH-range.

A new series of pH-responsive fluorescent dyes, which can be used intensity-based or lifetime-based measurements, may then be prepared. The pH responsiveness can be ratiometric by inclusion of a reference dye or the use of lifetime-based detection.

Fabrication of a fluorescence-based sensor is not trivial. The active fluorescent dye component has to be photostable, it has to yield an easily detectable response, and must be immobilized in a porous matrix. The matrix has to be biocompatible, robust, and has to allow free and fast diffusion of analytes. The matrix has to be immobilized in a configuration allowing for easy read-out, whether it is at the end of a fiber optical wire or e.g. in the side of a single-use bioreactor.

Sensor Performance. Intensity Based Sensors

To make fluorescent-based sensors, an unresponsive such as $DMQA^+$ fluorescent dye used as reference signal may be attached in a sensor spot, along with a responsive triangelenium system.

Figure 3A:
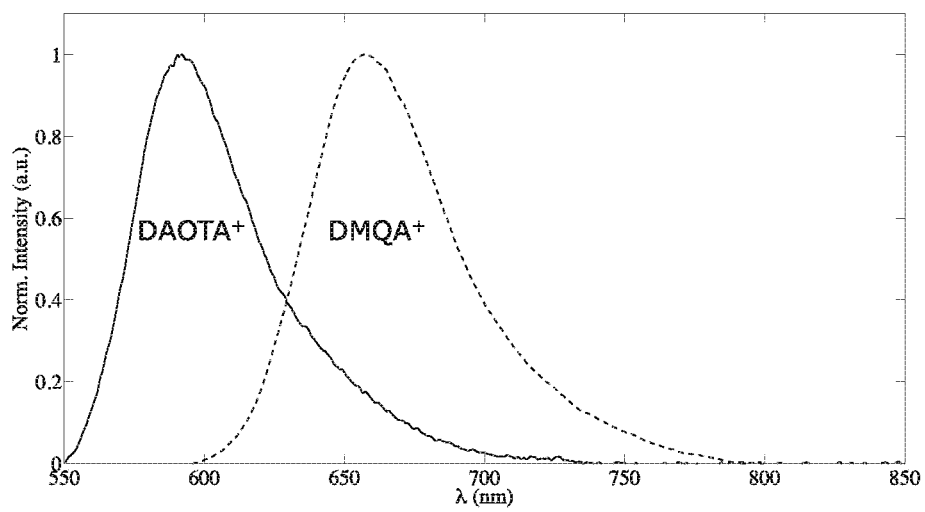
FIG. 3a shows the spectra of $DMQA^+$ (right, dotted) and $DAOTA^+4$ g (right, full) in ORMOSIL matrix material.
Figure 3B:
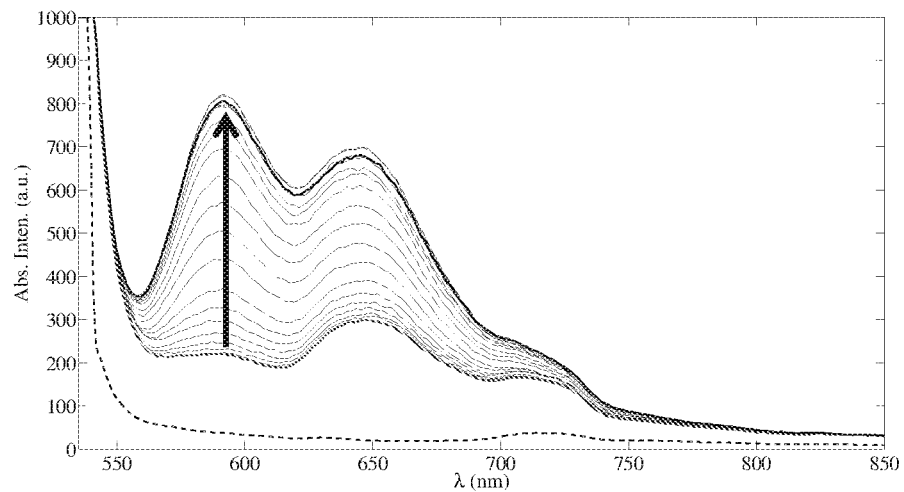
FIG. 3b shows the emission spectra/response of a sensor in ORMOSIL matrix material made from $DMQA^+$ and $DAOTA^+4g$ as a function of changing pH. The arrow indicates the pH change from ~11 to ~1. The dashed line shows the matrix background emission.

FIG. 3a and FIG. 3b show the response of a sensor comprising $DMQA^+$ as reference signal 4g as a responsive $DAOTA^+$ system in an ORMOSIL matrix material. It can be seen that the two signals clearly change intensity in a different manner as the pH is changed. This allows for a ratiometric determination of the pH by comparing an observed signal to a standard curve.

In order to validate the sensor performance, different stability tests were performed. One critical parameter for an optical sensor is known to be the read-out stability. Another critical parameter for optical sensors is the chemical stability.

Figure 4:
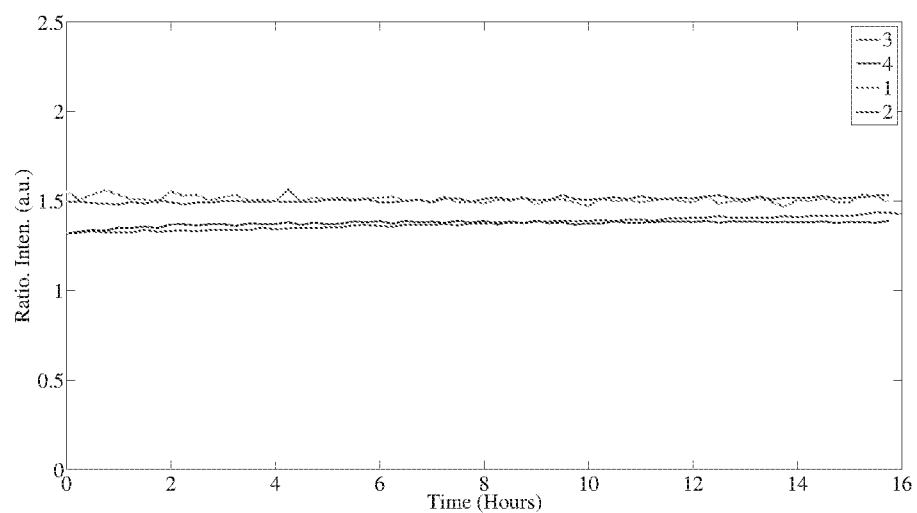
FIG. 4 shows the ratiometric readout signal of a sensor made from $DMQA^+$ and 4g over time, at high pH and at low pH.

FIG. 4 shows that the ratiometric readout signal from an optical sensor comprising $DMQA^+$ and 4g in an ORMOSIL matrix material is stable for at least 16 hours.

Figure 5:
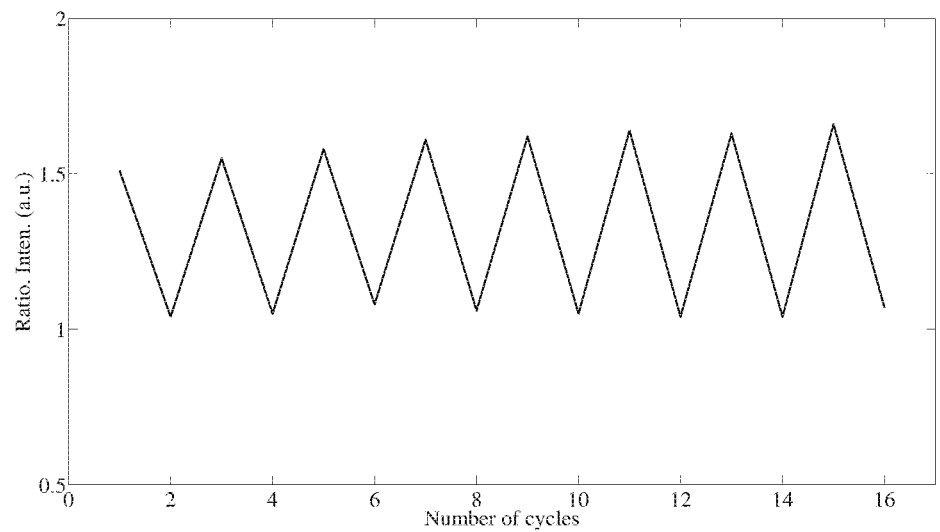
FIG. 5 shows the ratiometric readout signal of a sensor made from $DMQA^+$ and 4g in a PBS solution at changing pH conditions, pH=3 to 9.
Figure 6:
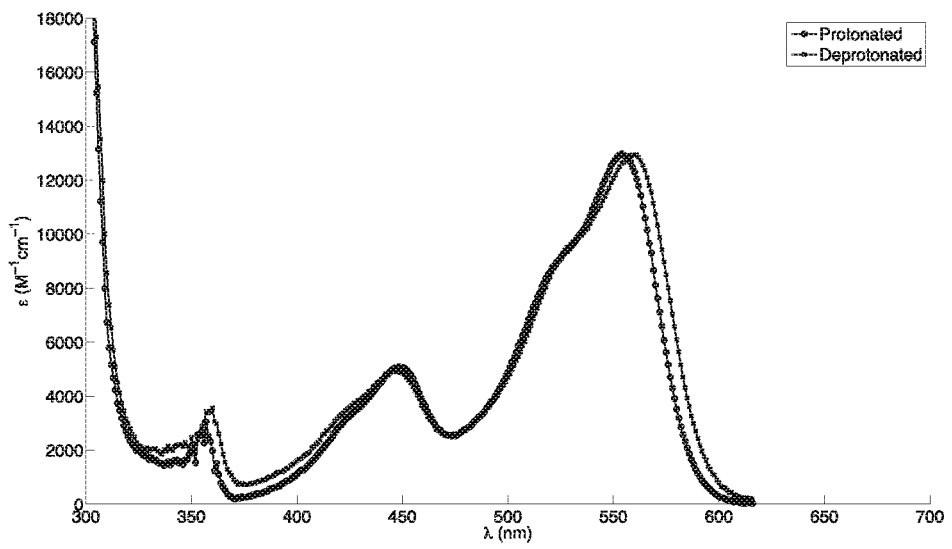
FIG. 6. Absorption spectra of MR-68_DAOTA measured in 6% DMSO in PBS buffer solution. Circles (o) represent the absorption spectrum of the protonated form (measured at acidic conditions) and crosses (x) represent the absorption spectrum of the deprotonated form (measured at basic conditions).
Figure 7:
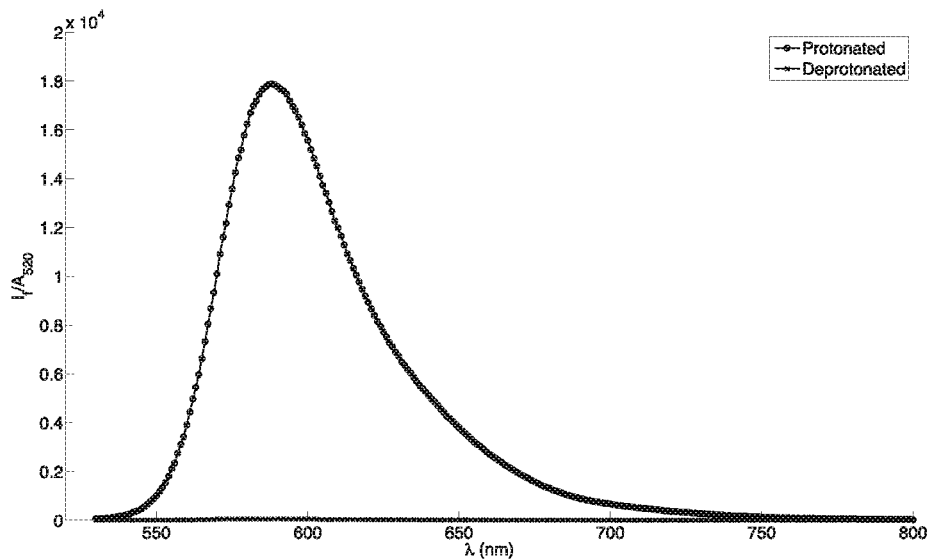
FIG. 7. Emission spectra of MR-68_DAOTA measured in 6% DMSO in PBS buffer solution. Circles (o) represent the absorption spectrum of the protonated form (measured at acidic conditions) and crosses (x) represent the absorption spectrum of the deprotonated form (measured at basic conditions).
Figure 8:
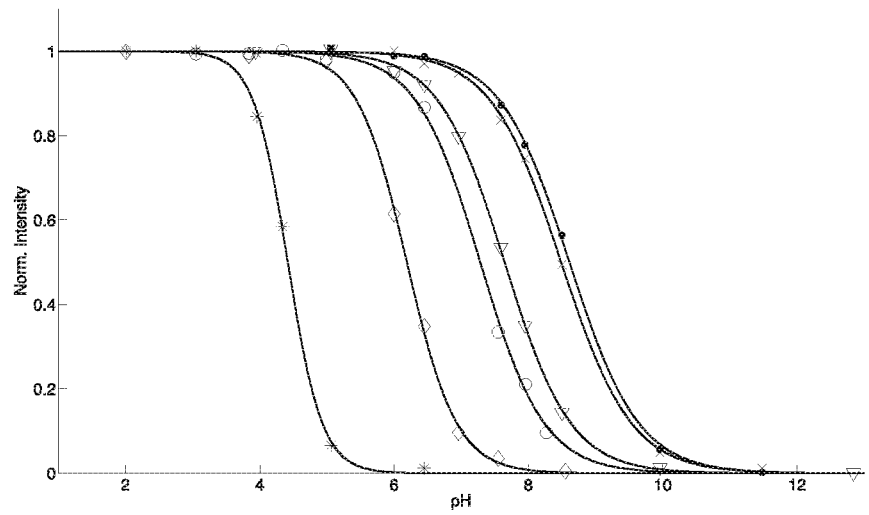
FIG. 8. Normalized fluorescence intensity at 588 nm at different pH values for MR-69_DAOTA (stars, $pK_a$=4.4), MR-66_DAOTA (diamonds, $pK_a$=6.2), MR-67.1_DAOTA (open circles, $pK_a$=7.3), MR-68_DAOTA (triangles, $pK_a$=7.6), MR-73.1_DAOTA (crosses, $pK_a$=8.5), and MR-93_DAOTA (dots, $pK_a$=8.6). The solid lines are sigmoidal fits to the experimental data.
Figure 9:
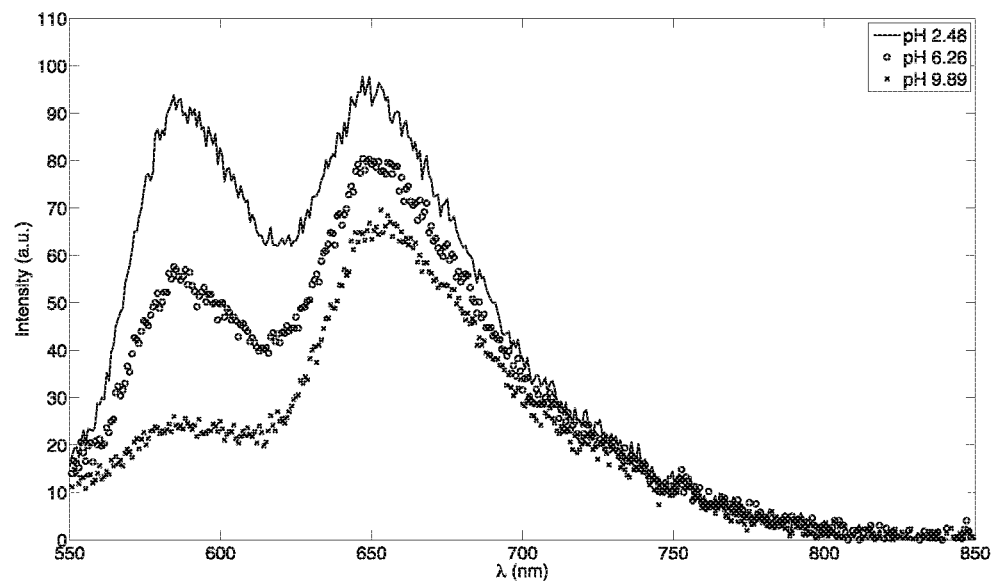
FIG. 9. Emission spectra of a pH sensor spot loaded with I1C (signal at ca. 590 nm) and R1C (signal at ca. 650 nm) covalently bound into the SOL-GEL-matrix recorded at different pH values (solid line: pH 2.48, circles: pH 6.26, crosses: 9.89).
Figure 10:
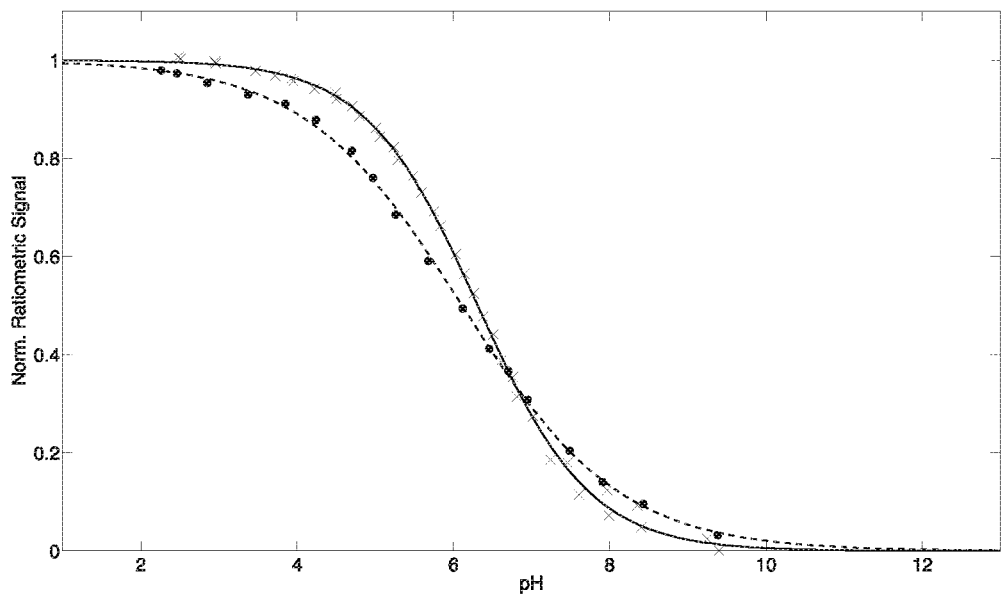
FIG. 10. Ratiometric emission signal extracted from the emission spectra from measured on a pH sensor spot loaded with I1C and R1C covalently bound into the SOL-GEL-matrix (crosses, $pK_a$=6.3) and I1L and R1L lipophilic bound into the SOL-GEL-matrix (dots, $pK_a$=6.1) measured at different pH values.
Figure 11:
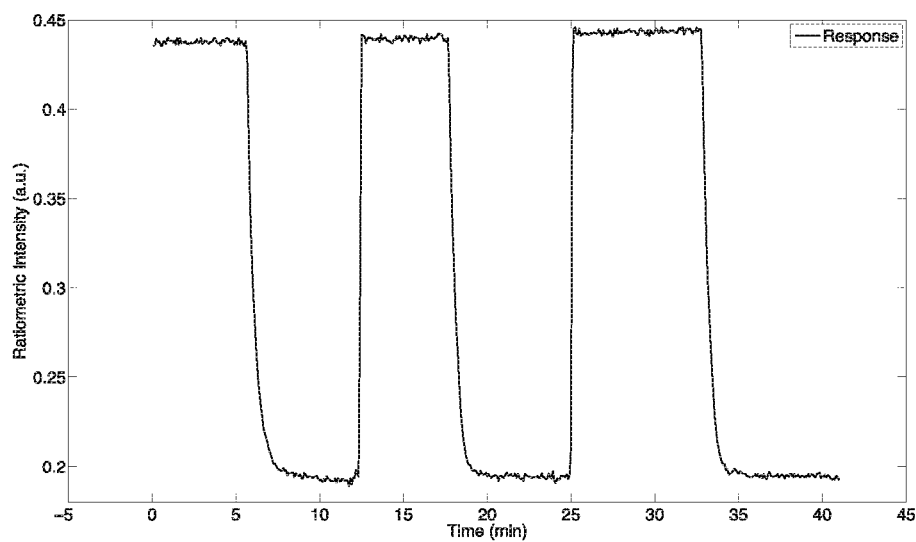
FIG. 11. Response time of the ratiometric emission signal between I1C and R1C, covalently bound into the SOL-GEL-matrix when pH is changed between from 2 (high values) to 12 (low values). Response time ($t_{90}$) is less than 30 s.
Figure 12:
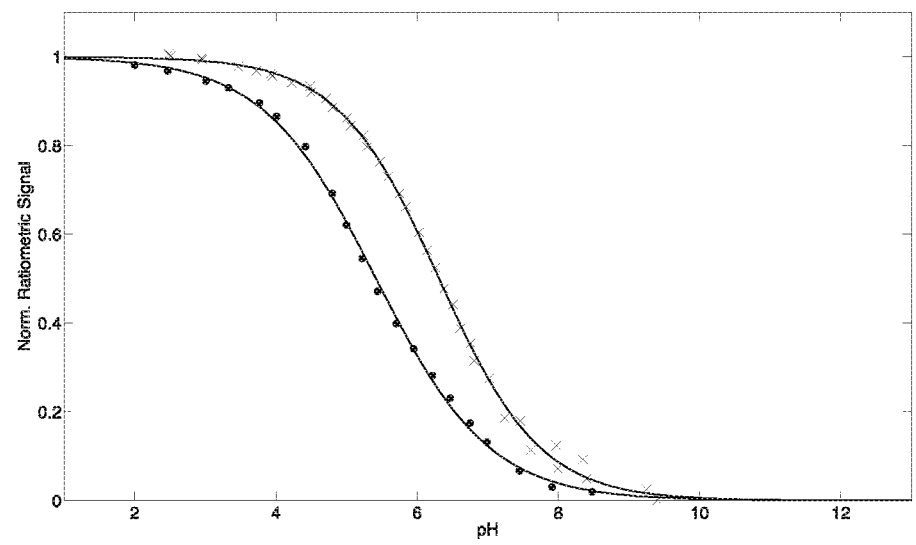
FIG. 12. Normalized ratiometric emission signal between I2C and R1C covalently bound into the SOL-GEL-matrix (dots, $pK_a$=5.4) bound into the SOL-GEL-matrix and I1C and R1C (crosses, $pK_a$=6.3) covalently bound into the SOL-GEL-matrix measured at different pH values. $pK_a$ value: 5.4.

FIG. 5 shows that the ratiometric readout signal from an optical sensor comprising $DMQA^+$ and 4g in an ORMOSIL matrix material maintains its responsiveness, when the sensor are subjected to constant illumination and low and high pH.

A comparison between solution and sol-gel spectra for compound of Formula (I), 4g, along titration curves for one of the responsive molecules shows that the spectral change is minimal while the response to changing pH is maintained upon attaching to the matrix material.

Thus, a very high photostability of compounds of Formula I and compounds of Formula (II) have been demonstrated.

Spectroscopy

All disclosed absorption and emission spectrum measurement shown herein are measured as follows:

Emission spectroscopy was performed in front-face set-up for sensor spot samples and in a conventional L-shape set-up for measuremetns in solution. A Perkin-Elmer LS50B and a Horiba Fluorolog 3 were used interchangeably. Intensity based sensor measurements were only performed on the LS50B platform. Fluorescence lifetime based sensor measurements were only performed on the Fluorolog 3. Absorption spectroscopy was performed on a Perkin Elmer Lambda1050, with integrating sphere (for sensor spots) and with a 3-detector module for solution samples.

Synthesis

All compounds required for the preparation of compounds of Formula (I) were of analytical or HPLC grade and used as received.

tris(2,6-dimethoxyphenyl)-methylium, $DMP_3C^+$

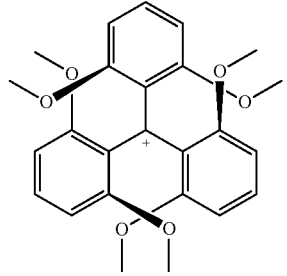

$DMP_3C$—$BF_4$ was synthesized according to well-known procedures, see e.g. Martin, J. C. Smith, R. G.[23], which hereby is incorporated as reference.

General Procedure for the Synthesis of 1 from Complex Primary Amines:

A primary amine (17.8 mmol) was dissolved/suspended in acetonitrile (50 ml) and then heated to reflux temperature. Then 2,6-lutidine (20 ml, 173 mmol) was added. A solution of $DMP_3C.BF_4$ (5.04 g, 9.88 mmol) was dissolved in acetonitrile (250 ml) and then added slowly dropwise (1 drop per 5-10 s) to the hot solution of the phenol compound. The addition was allowed to proceed overnight (16 h). The red reaction mixture was analyzed by MALDI-TOF (dithranol matrix) and this analysis indicated that no starting material was present. The reaction mixture was allowed to cool down, and then poured into an acidified $KPF_6$ solution (10 ml 2 M HCl in 1500 ml 0.2 M $KPF_6$) upon vigorous stirring. A red precipitate formed and the suspension was gently stirred for 15 min and then filtered. The filtrate was washed with HCl solution (2 M), then with water, and finally with heptane until the heptane phase was nearly colorless. The red sticky mass was dissolved in a minimum of $CH_2Cl_2$ through the filter. The product was precipitated with heptane and filtered off and washed with heptane (2×100 ml). The product was dissolved in a minor amount of acetonitrile and poured onto diethyl ether upon stirring. The red precipitate was allowed to form for 15 min, filtered off, and then washed with ether (2×100 ml). The red sticky product was collected and dissolved in CH$_2$Cl$_2$. The CH$_2$Cl$_2$ was removed by evaporation yielding 17 g of red-gray fine powder. The red powder was suspended in pure water and stirred overnight. The red powder was filtered off, washed with water, and sucked dry. The sticky red product was dissolved in acetonitrile through the funnel and then the solvent was removed by evaporation. The red powder was collected and dried on an oil pump for 1 day.

General Procedure for the Synthesis of 1 from Simple Primary Amines:

1 eq. DMP$_3$C—BF$_4$, 1.2 eq amine and 1.5 eq triethylamin is dissolved in 5 ml MeCN per gram of starting material. After 30 mins the reaction is investigated by MALDI-TOF. It will have run to completion. 600 ml of 0.2 M NaBF4 (aq) is added to the solution. After 12 hours the product is collected by filtration. The crude product is recrystallized from MeOH~10 ml per gram of starting material.

9-(2-methoxyphenyl)-1,8-dimethoxy-10-(2,6-dimethoxyphenyl)-acridium tetrafluorobarat 1b

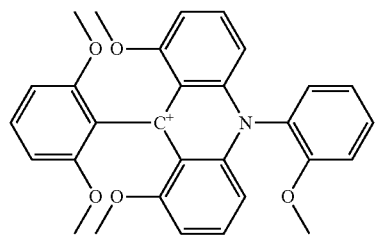

1b

The product was isolated by precipitation from dichloromethane with ether as a dark orange powder. Yield 1.38 g (48%). $^1$H NMR (500 MHz, DMSO-d$_6$) δ 8.11 (dd, J=9.0, 8.0 Hz, 2H), 7.90 (ddd, J=8.5, 7.5, 1.7 Hz, 1H), 7.81 (dd, J=7.8, 1.6 Hz, 1H), 7.63 (dd, J=8.5, 1.2 Hz, 1H), 7.54-7.43 (m, 2H), 7.27-7.20 (m, 2H), 6.93 (dd, J=9.1, 0.8 Hz, 2H), 6.87 (ddd, J=8.4, 6.8, 0.7 Hz, 2H), 3.71 (s, 3H), 3.62 (s, 3H), 3.59 (s, 3H), 3.57 (s, 6H). $^{13}$C NMR (125 MHz, DMSO) δ 159.88, 158.21, 155.52, 155.11, 153.54, 142.08, 140.37, 133.34, 129.62, 129.03, 125.99, 122.52, 119.04, 118.66, 114.20, 110.00, 107.07, 103.76, 57.25, 56.34, 55.98, 55.95. Elemental analysis, theoretical elemental composition: C, 63.29; H, 4.96; N, 2.46. Found: C, 62.84; H, 4.68; N, 2.60.

9-(3-methoxyphenyl)-1,8-dimethoxy-10-(2,6-dimethoxyphenyl)-acridium tetrafluorobarat 1c

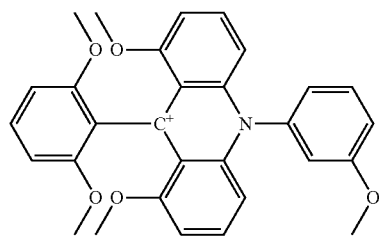

1c

The product was isolated by precipitation from dichloromethane with ether as a dark orange powder. Yield 1.13 g (39%). $^1$H NMR (500 MHz, DMSO-d$_6$) δ 8.09 (dd, J=9.1, 8.0 Hz, 2H), 7.80 (dd, J=8.5, 7.8 Hz, $^1$H), 7.53 (t, J=2.2 Hz, 1H), 7.47 (t, J=8.4 Hz, 1H), 7.43 (ddd, J=8.5, 2.5, 0.9 Hz, 2H), 7.37 (ddd, J=7.8, 2.0, 0.9 Hz, 1H), 7.21 (dd, J=8.2, 0.8 Hz, 2H), 6.94 (dd, J=9.1, 0.9 Hz, 2H), 6.85 (ddd, J=8.4, 2.9, 0.7 Hz, 2H), 3.85 (s, 3H), 3.59 (d, J=6.3 Hz, 6H), 3.55 (s, 6H). Elemental analysis, theoretical elemental composition: C, 63.29; H, 4.96; N, 2.46. Found: C, 63.84; H, 4.83; N, 2.46.

9-(4-methoxyphenyl)-10-(2,6-dimethoxyphenyl) acridinium tetrafluorobarat 1d

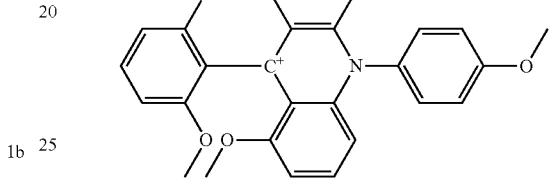

1d

The product was isolated after precipitation using passive diffusion in layered a acetonitrile, ether, heptane system. Yield 2.02 g (84%). $^1$H NMR (500 MHz, CD$_3$CN) δ 7.96 (t, J=8.5 Hz, 2H), 7.53-7.43 (m, 3H), 7.39-7.34 (m, 2H), 7.07 (d, J=7.9 Hz, 2H), 6.99 (d, J=9.0 Hz, 2H), 6.81 (d, J=8.3 Hz, 2H), 4.01-3.95 (m, 3H), 3.62-3.56 (m, 6H), 3.56-3.53 (m, 6H). $^{13}$C NMR (125 MHz, DMSO-d$_6$) δ 160.79, 159.75, 157.47, 155.40, 142.76, 139.64, 131.03, 129.54, 129.30, 119.09, 118.79, 116.30, 110.98, 106.78, 103.76, 57.23, 55.93, 55.83. Elemental analysis, theoretical elemental composition: C, 63.29; H, 4.96; N, 2.46. Found: C, 62.75; H, 4.94; N, 2.99.

9-(2,6-dimethoxyphenyl)-1,8-dimethoxy-10-(2,6-dimethoxyphenyl)-acridium hexafluorophosphate 1f

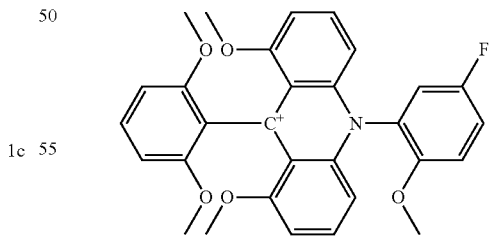

1f

Standard procedure followed. Heating of a solution 2-methoxy-5-fluoroaniline (500 mg, 3.5 mmol) in 20 ml acetonitrile and 2,6-lutidine (2 ml, 17 mmol) to reflux temperature. Slowly addition of a solution of DMP$_3$C$^+$BF$_4^-$ (1.55 g, 3 mmol) in 250 ml acetonitrile. Isolated as a dark powder. Yield: 900 mg (46%). MALDI-TOF (Dithranol matrix): m/z 500.

9-(2-hydroxy-5-(methylsulfonyl)phenyl)-1,8-dimethoxy-10-(2,6-dimethoxyphenyl)-acridium hexafluorophosphat 1g

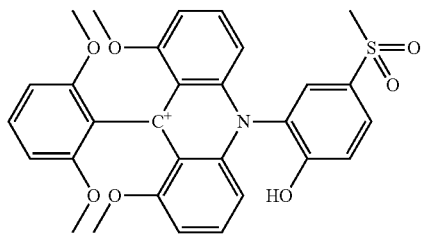

The red powder was collected and dried on an oil pump for 1 day. Yield: 5.44 g (80%). $^1$H NMR (500 MHz, CD$_3$CN): δ 8.22 (dd, J=2.2 Hz, J=9 Hz, 1H), 8.12 (d, J=2.2 Hz), 8.02 (d, J=8.1 Hz, 1H), 8.00 (d, J=8.1 Hz, 1H), 7.51 (d, J=8.8, 1H), 7.48 (t, J=8.4, 1H), 7.11 (d, J=8.0 Hz, 2H), 7.04 (dd, J=9 Hz, J=0.8 Hz, 2H) 6.82, (dd, J=7.5, J=1.0 Hz, 2H), 3.61 (s, 3H), 3.60 (s, 3H), 3.58 (s, 6H), 3.16 (s, 3H). MALDI-TOF (Dithranol matrix): m/z 546.

9-(2-methoxy-5-(trifluoromethyl)phenyl)-1,8-dimethoxy-10-(2,6-dimethoxyphenyl)-acridium hexafluorophosphate 1h

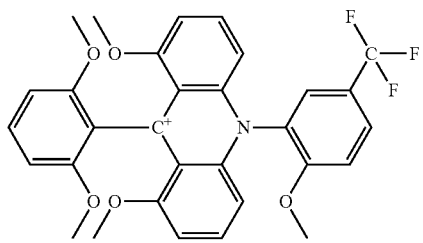

Standard procedure followed. Heating of a solution 2-methoxy-5-(trifluoromethyl)aniline (5 g, 26 mmol) in 50 ml acetonitrile and 2,6-lutidine (20 ml, 713 mmol) to reflux temperature. Slowly addition of a solution of DMP$_3$C$^+$BF$_4^-$ (10.2 g, 20.1 mmol) in 250 ml acetonitrile. Isolated as a purple powder. Yield: 8.2 g (59%). $^1$H NMR (500 MHz, DMSO-d$_6$) δ 8.46 (d, J=2.1 Hz, 1H), 8.29 (dd, J=9.1, 2.1 Hz, 1H), 8.14-8.07 (m, 2H), 7.81 (d, J=8.9 Hz, 1H), 7.48 (t, J=8.4 Hz, 1H), 7.22 (d, J=7.8 Hz, 2H), 6.92 (d, J=9.0 Hz, 2H), 6.86 (t, J=8.6 Hz, 2H), 3.80 (s, 3H), 3.61 (s, 3H), 3.58 (s, 3H), 3.56 (s, 6H). MALDI-TOF (Dithranol matrix): m/z 546.

General Procedure for the Synthesis of 2 with Long Alkyl Primary Amines:

DMP$_3$C$^+$BF$_4^-$ (4 mmol) was dissolved in NMP (150 ml) and then added dropwise to a portion molten long chain primary amine (30 mmol) at a temperature of 110-115° C. The addition was allowed to proceed by addition of 1-2 drops per second. When the addition was complete the reaction was allowed to react for 1 h (TLC analysis, toluene: ethanol, 70:30 v/v indicated that the starting material was consumed after 1 h). The green-blue reaction mixture was allowed to cool down to 30-40° C. to prevent the residual dodecylamine to precipitate, and this mixture was then washed heptane (3×200 ml). If a white solid forms it was filtered off. Then an HCl solution (6 M) was added slowly and an emulsion formed. The emulsion was extracted with CH$_2$Cl$_2$ and then the CH$_2$Cl$_2$ was removed by evaporation. The sticky solid was suspended in acetonitrile and cooled to 0-5° C. and then filtered while cold. The acetonitrile was removed by evaporation and then suspended again in acetonitrile. The latter procedure was repeated until successful filtration was not possible anymore. The green sticky material was then adsorbed on Celite (from CH$_2$Cl$_2$) and the green product was purified using dry vacuum column chromatography (toluene:ethanol, 1% gradient).

General Procedure for the Synthesis of 2 Simple Primary Amines:

A primary amine (20 eq, 40 mmol) was added to a solution 1 or 2 in NMP (2 mmol in 8 mL). The solution was warmed to 140° C. for 10-20 minutes (the degree of reaction is followed by MALDI-TOF mass spectrometry). After cooling to RT the reaction mixture was poured on to 0.2 M KPF$_4$(aq) (200 mL). The precipitate was collected, washed and dried. The crude can be recrystallized from methanol, reprercipitated from dichloromethane with ethylacetate or reprecipitated from acetonitrile with ether depending on how lipophilic the side chains are.

General Procedure to the Synthesis of 3:

Compound 3c (0.66 g, 1.37 mmol) was heated, under nitrogen, with pyridine hydrochloride (9.66 g) to 160° C. (oil bath). A small amount of pyridine (approx. 0.5 ml) was added to keep pyridinhydrochloriden in solution. The reaction time was approx. 5 hours (followed by MALDI-TOF-MS). At completion of the reaction, the reaction mixture was poured over with ice/water (30 mL). Dark red crystals were precipitated by addition of HBF 4 (aq.) (40%, 6 ml), wherefater the solution was filtered. The product was redissolved in acetonitrile (6 ml), and to reprecipitated (addition of ether, 30 mL). After filtration and drying, a yield of dark red crystals of 0.41 g (81%) were obtained.

N-(2-hydroxyphenyl)-azadioxatriangulenium tetrafluoroborat 3b

By dropwise addition of 48% HBF$_{4(aq)}$ to a methanol solution of the crude product red crystals could be collected. Precipitation from dichloromethane with ether afforded the product as red crystals in a yield of 0.15 g (48%). $^1$H NMR (500 MHz, DMSO-d$_6$) δ 10.78-10.67 (m, 1H), 8.31-8.25 (m, 3H), 7.73 (dd, J=8.3, 7.1 Hz, 4H), 7.68 (dt, J=8.7, 1.7 Hz, 1H), 7.52 (dd, J=7.8, 1.7 Hz, 1H), 7.42 (ddd, J=8.5, 3.2, 1.6 Hz, 1H), 7.27 (td, J=7.6, 1.3 Hz, 1H), 6.96 (d, J=8.7 Hz, 2H). $^{13}$C NMR (125 MHz, DMSO) δ 153.08, 152.51, 152.16, 141.51, 141.21, 141.00, 140.17, 132.62, 128.93, 122.72, 121.19, 118.30, 111.73, 110.72, 109.32, 108.31, 105.89. Elemental analysis, theoretical elemental composition: C, 64.83; H, 3.05; N, 3.02. Found: C, 64.95; H, 3.03; N, 3.52%.

N-(3-hydroxyphenyl)-azadioxatriangulenium tetrafluoroborat 3c

By dropwise addition of 48% HBF$_{4(aq)}$ to a methanol solution of the crude product red crystals could be collected. Precipitation from dichloromethane with ether afforded the product as red crystals in a yield of 0.31 g (95%). $^1$H NMR (500 MHz, DMSO-d$_6$) δ 10.56 (s, 1H), 8.24 (td, J=8.5, 5.3 Hz, 2H), 7.80 (dd, J=8.5, 7.8 Hz, 1H), 7.73-7.69 (m, 2H), 7.40 (ddd, J=8.5, 2.5, 0.9 Hz, 1H), 7.26 (t, J=2.3 Hz, 1H), 7.19 (ddd, J=7.8, 1.9, 0.9 Hz, 1H), 6.92 (d, J=8.7 Hz, 1H). $^{13}$C NMR (125 MHz, DMSO-d$_6$) δ 160.26, 152.29, 152.04, 144.28, 143.39, 141.32, 140.86, 137.30, 132.70, 126.58, 118.25, 117.62, 114.21, 111.86, 111.11, 109.26, 108.28, 105.64 Elemental analysis, theoretical elemental composition: C, 64.83; H, 3.05; N, 3.02. Found: C, 65.01; H, 3.30; N, 3.23%.

4-(3-hydroxyphenyl)-azadioxatriangulenium tetrafluoroborat 3d

Recrystallization from isopropanol afforded the product as a red powder in a yield of 0.203 g (41%). $^1$H NMR (500 MHz, DMSO-$d_6$) δ 10.44 (d, J=2.9 Hz, 1H), 8.26 (td, J=8.4, 1.5 Hz, 3H), 7.72 (d, J=8.3 Hz, 4H), 7.48-7.38 (m, 2H), 7.27-7.18 (m, 2H), 6.97 (d, J=8.8 Hz, 2H). $^{13}$C NMR (125 MHz, DMSO-$d_6$) δ 159.40, 152.30, 152.05, 142.02, 141.19, 140.74, 140.74, 140.18, 129.04, 127.36, 118.08, 111.84, 111.22, 110.93, 109.20, 108.33, 105.64.

N-(p-aminophenyl)-azadioxatriangulenium tetrafluoroborat 3e

The product was isolated as a red powder in a yield of 0.23 g (68%). $^1$H NMR (500 MHz, CD$_3$CN) δ 7.96 (dd, J=9.1, 8.0 Hz, 2H), 7.46 (t, J=8.4 Hz, 1H), 7.25-7.19 (m, 2H), 7.11 (dd, J=9.1, 0.8 Hz, 2H), 7.05 (d, J=7.7 Hz, 2H), 7.04-6.99 (m, 2H), 6.80 (d, J=8.4 Hz, 2H), 4.83 (s, 2H), 3.60 (s, 6H), 3.55 (s, 6H). $^{13}$C NMR (125 MHz, CD$_3$CN) δ 160.97, 159.04, 156.81, 151.52, 144.72, 140.06, 130.49, 129.28, 128.53, 120.67, 120.41, 116.36, 112.36, 107.34, 104.65, 57.72, 56.59.

General Procedure to the Synthesis of 4:

The green sticky product was heated with pyridinium hydrochloride (25 g, 216 mmol) to 200-220° C. The mixture was heated for 30-60 min (until MALDI-TOF analysis indicated that no m/z 667 was present or when TLC analysis, toluene:ethanol, 70:30 v/v, indicated that no green material was present). The hot purple solution was poured into 300 ml water upon stirring. The residual material was washed out of the flask with a small amount of acetone or acetonitrile. The volume was increased to 500 ml and the suspension was stirred vigorously for 10-15 min until room temperature was reached. The solution was filtered and washed with water. The purple solid was dissolved in CH$_2$Cl$_2$ through the funnel. The organic phase was washed twice with a 2M HCl solution (2×100 ml) and then organic phase was dried over Na$_2$SO$_4$. The purple product was adsorbed on Celite (from CH$_2$Cl$_2$) and purified by dry vacuum column chromatography (toluene:ethanol, 1% gradient). When the fractions containing the compound were isolated, the compound was dissolved in CH$_2$Cl$_2$ and washed with an 2M HCl solution (2×100 ml).

N-(2-hydroxyphenyl)-N'-dodecyl-diazaoxatriangulenium hexafluorophosphat 4b

General preparation and purification procedure as described followed. 1b (1 g, 1.8 mmol) and dodecylamine (10 g, 54 mmol) in 50 ml NMP subsequently the green sticky intermediate product was oxygen ring closed using pyridinium chloride (25 g, 216 mmol). Yield: mg (80 mg, 7%). $^1$H NMR (500 MHz, CD$_3$CN) δ 8.11 (t, J=8.3 Hz, 1H), 8.04 (t, J=8.5 Hz, 1H), 7.88 (t, J=8.3 Hz, 1H), 7.67-7.56 (m, 3H), 7.46 (d, J=8.6 Hz, 1H), 7.41-7.25 (m, 4H), 6.69 (dd, J=8.7, 0.7 Hz, 1H), 6.64 (d, J=8.5 Hz, 1H), 4.58-4.42 (m, 2H), 1.59 (tt, J=7.8, 6.3 Hz, 2H), 1.43 (quin, J=6.8 Hz, 2H) 1.39-1.21 (m, 16H), 0.87 (t, J=7.0 Hz, 3H). $^{13}$C NMR (126 MHz, CD$_3$CN) δ 153.95, 153.59, 153.48, 143.29, 142.01, 141.75, 141.61, 141.16, 140.42, 139.76, 139.36, 133.38, 130.42, 124.62, 123.48, 119.32, 112.48, 110.87, 110.39, 109.61, 109.47, 109.15, 108.47, 107.57, 107.21, 49.04, 32.61, 30.30, 30.21, 30.20, 30.03, 29.95, 27.20, 26.41, 23.36, 14.35. MALDI-TOF (Dithranol matrix): m/z 543.

Yield: 200 mg (6%—with respect to 2). $^1$H NMR (500 MHz, CD$_3$CN): δ 12.81 (s, 1H), 8.10 (m, 2H), 8.00 (t, J=8.5 Hz, 1H), 7.93 (d, J=0.2 Hz, 1H), 7.86 (t, J=8.3 Hz, 1H), 7.82 (t, J=8.5 Hz, 1H), 7.41 (d, J=8.9 Hz, 1H), 7.38 (d, J=8.7 Hz, 1H), 7.19 (d, J=8.1 Hz, 1H), 7.11 (d, J=8.1 Hz, 1H), 6.74 (d, J=8.6 Hz, 1H), 6.7 (d, J=8.4 Hz, 1H), 4.27 (m, 2H), 3.13 (s, 3H), 1.78 (quin, J=7.5 Hz, 2H), 1.52 (quin, J=7.1 Hz, 2H), 1.4-1.2 (m, 16H), 0.87 (t, J=7.1 Hz, 3H). $^{13}$C NMR (101 Hz, CD$_3$CN): δ 160.3, 153.4, 153.1, 142.9, 141.7, 141.3, 141.2, 140.7, 140.6, 139.7, 139.5, 133.6, 132.5, 130.5, 124.6, 120.6, 112.1, 111.1, 110.3, 109.7, 109.4, 108.6, 108.1, 107.9, 107.4, 48.9, 45.2, 32.6, 30.3, 30.24, 30.23, 30.0, 29.9, 27.1, 26.3, 23.4, 14.4. (1 signal is missing) MALDI-TOF (Dithranol matrix): m/z 622 (M$^+$). Anal. Found: C, 68.5; H, 6.13; N, 4.15. Calcd for C$_{38}$H$_{41}$N$_2$O$_4$Cl: C, 69.44; H, 6.29; N, 4.26.

N-(2-hydroxy-5-(trifluoromethyl)phenyl)-N-dodecyl-diazaoxatriangulenium hexafluorophosphat 4h General preparation and purification procedure as described was followed. 1h (3 g, 4.3 mmol) and dodecylamine (24 g, 129 mmol) in 100 ml NMP subsequently the green oily intermediate product was oxygen ring closed using pyridinium chloride (25 g, 216 mmol). Yield: (150 mg, 4%). $^1$H NMR (500 MHz, CD$_3$CN) δ 8.02 (dt, J=12.4, 8.5 Hz, 2H), 7.82 (q, J=8.1, 7.7 Hz, 2H), 7.73-7.49 (m, 3H), 7.42 (d, J=8.6 Hz, 1H), 7.34-7.17 (m, 2H), 6.67 (dd, J=20.5, 8.5 Hz, 2H), 4.44 (t, J=8.4 Hz, 2H), 1.93-1.85 (m, 2H), 1.60 (p, J=7.4 Hz, 2H), 1.49-1.24 (m, 16H), 0.96-0.87 (m, 3H). MALDI-TOF (Dithranol matrix): m/z 611 (M$^+$).

4i, 4j, and 4k

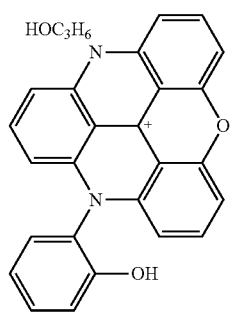

4i

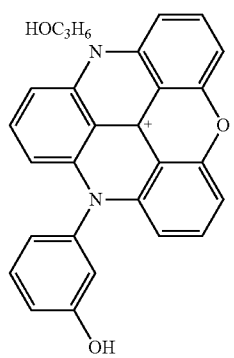

4j

-continued
4k
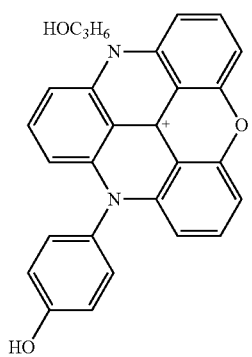
were synthesized in an analogue procedure corresponding to the procedures of 1b, 1c, 1d and 4b.
4l, 4m, and 4n
4l
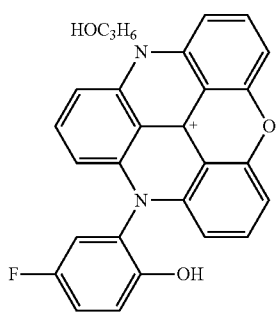
4m
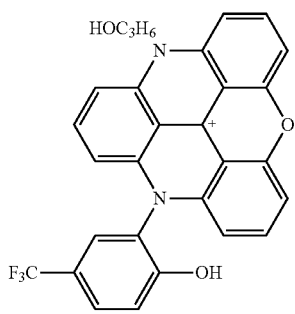
4n
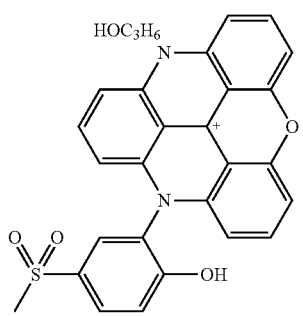
were synthesized in an analogue procedure described herein.
4o, 4p, 4q, 4r, 4s, 4t, and 4u
4o
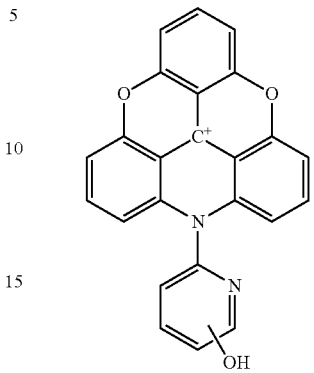
4q
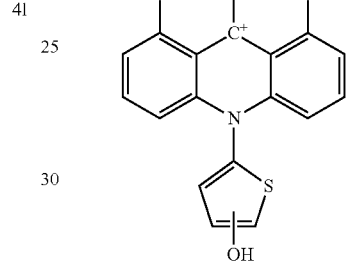
4p
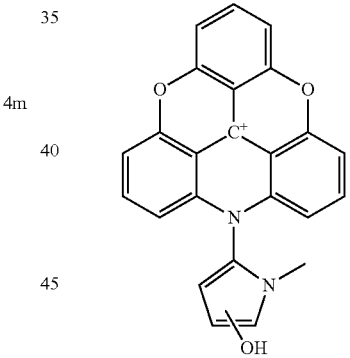
4r
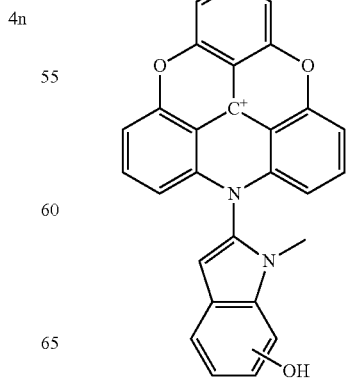

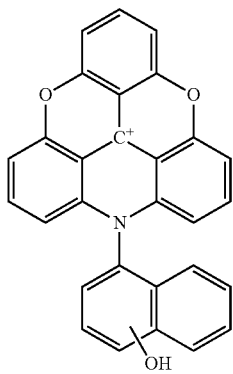

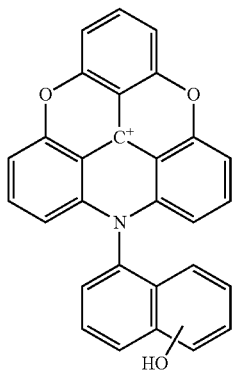

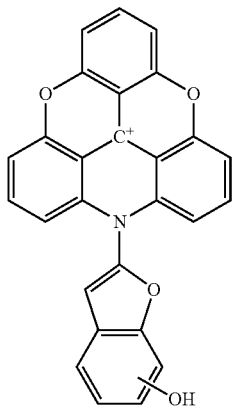

N,N'-diphenyl-N''-(2-hydroxy-4-methylsulfonyl-phenyl)-triazatriangulenium 5

1g (504 mg, 0.73 mmol) was dissolved in aniline (20 ml, 219 mmol) in a 500 ml round-bottomed flask with a large magnetic stirring bar. Then NaH (60% suspension in mineral oil, 200 mg, 5 mmol) was added to the solution and the mixture was heated to 200° C. The color of the reaction mixture changed from red to green-blue and then from green-blue to purple. When the reaction mixture became purple a TLC analysis was performed (ethanol:toluene, 20:80 v/v %), which indicated the presence of a minor amount of DMQA product and the reaction was proceeded for additionally 20 min. After 20 min the mixture was allowed to cool to room temperature and upon vigorous stirring water was added until slurry formed. The slurry was acidified using 2M HCl solution. A purple precipitate formed, which was filtered off and washed with water several times and sucked dry. The purple solid was then washed with diethyl ether, dissolved in $CH_2Cl_2$ through the filter, and the organic phase was dried over $Na_2SO_4$. The volume of the organic phase was reduced by evaporation and upon vigorous stirring diethyl ether was added to the solution until a purple precipitate formed. The product was filtered off and washed with diethyl ether. The purple solid was adsorbed on Celite 560 and purified by dry vacuum column chromatography (toluene-ethanol, 2% gradient). The dark colored product was dissolved in acetonitrile and made basic by addition of a few drops of triethylamine. Then diethyl ether was added until the product precipitated as the inner salt, which was collected as washed with diethyl ether several times. Yield: 25 mg (5%). $^1$H NMR (300 MHz, $CD_3CN$) δ 8.00 (d, J=8.8 Hz, 1H), 7.95 (d, J=2.2 Hz, 1H), 7.89-7.73 (m, 6H), 7.68-7.47 (m, 8H), 6.53 (d, J=8.5 Hz, 2H), 6.42-6.34 (m, 4H), 3.09 (d, J=0.8 Hz, 3H). MALDI-TOF (Dithranol matrix, addition of 48% $HBF_4$ in $H_2O$): m/z 604.

Preparation of Monomers for Sol-Gel Matrix

Compounds were used as received. Sol-gel monomers were purchased from Sigma-Aldrich. Sol-gel catalysts were purchased from Sigma-Aldrich and used as recieved. Solvents used were analytical or HPLC grade. An electronically controlled oven was used to cure the ORMOSIL thin-films. A dipper arm from KSV was used for dip coating of the sol-gel films on glass prior to curing. Deposition of SOL-GEL sensor materials using hemiwicking is disclosed in the paper about the Hemiwick platform[22].

N-(2-hydroxy-5-(trifluoromethyl)phenyl)-N'-(6-aza-4-oxa-5-oxo-9-trimethoxysilyl-nonan)-diazaoxatri-angulenium hexafluorophosphat 6

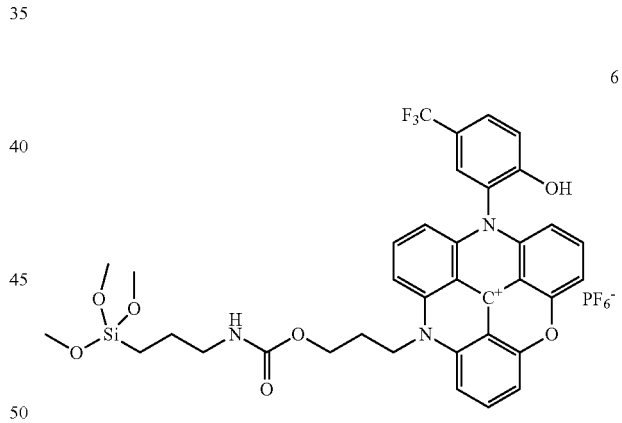

9-(2-methoxy-5-(trifluoromethyl)phenyl)-1,8-dimethoxy-10-(2,6-dimethoxyphenyl)-acridium hexafluorophosphate 1h (1.38 g, 1.98 mmol) was dissolved in NMP (20 ml) and 5 drops of 2,6-lutidine and the solution was heated to 100-110° C. Then 3-amino-1-propanol (1 ml, d=0.987 g/ml, 13.1 mmol) was added and the mixture was stirred at 100° C. for 1 h. and 20 min. The reaction was followed using TLC analysis ($CH_2Cl_2$). The reaction mixture was allowed to cool to room temperature and was then poured into $KPF_6$ solution (0.2 M, 100 ml). The suspension was filtered slowly and washed with water (2×100 ml). The green solid product was dissolved in a mixture of acetone and $CH_2Cl_2$ until the nearly no green material was present in the filter. The solvent was removed by evaporation and the resulting green crude product was dissolved in $CH_2Cl_2$ and dried over $Na_2SO_4$. The organic phase was mixed with 100 ml n-heptane and the $CH_2Cl_2$ was removed by evaporation and the heptane phase was sonicated and the fine green-brown product was filtered off. The latter precipitation procedure was performed one more time. The crude product was dissolved in a minor volume acetonitrile and diethyl ether (300 ml) was added. The suspension was stirred for two days (weekend). The suspension was filtered and the sticky prodcut was adsrobed on Celite 560 and purified by dry vacuum flash chromatography (diethyl ether —$CH_2Cl_2$— acetone). The green-blue product was collected and MALDI-TOF analysis indicated that the desired product was present (m/z 561). The product was dried in vacuum over night. This product (200 mg, 0.28 mmol) and lithium chloride (1 g, 24 mmol) was suspended in a mixture of 2,6-lutidine (10 ml) and NMP (20 ml) and. The mixture was heated to 130-140° C. for 2-3 h. The reaction was followed using MALDI-TOF analysis when the mixture had turned purple and when addition of acid to a sample from the mixture increased the fluorescence from the sample. The hot mixture was poured into water (100 ml), which was made basic using a $NH_3$ solution (2 M). The purple product was extracted with $CH_2Cl_2$. The $CH_2Cl_2$ was removed in vacuum and the remaining solution was mixed with 200 ml diethyl ether. The mixture was left over night to allow precipitate to form. The precipitate was collected and then dissolved in $CH_2Cl_2$ and washed with an acidified 0.2 M $KPF_6$ solution (3×50 ml). The organic phase was dried over $MgSO_4$ and the solvent was removed in vacuum. The product was collected and dried in vacuum over night. This product (30 mg, M=646.44 g/mol, 464 mmol) was dissolved in anhydrous acetonitrile (8 ml) and heated to 60-70° C. Then 3-(triethoxysilyl)propylsilane isocyanate (1 ml, d=0.999 g/ml, 4.04 mmol) was added and the solution was stirred for 2 h. The hot reaction mixture was mixed with 50 ml n-heptane and the mixture was cooled down upon shaking with the heptane phase. The acetonitrile phase was washed with n-heptane (3×50 ml) and the solvent was removed by evaporation. The residue was triturated with diethyl ether for 10-15 min and then filtered slowly. The red powder was washed with diethyl ether, collected and then dried in vacuum over night. Yield: 5 mg (12%).

$^1$H NMR (300 MHz, Methanol-$d_4$) δ 8.25-8.06 (m, 3H), 7.94 (t, J=8.4 Hz, 2H), 7.86-7.80 (m, 1H), 7.68 (d, J=8.7 Hz, 1H), 7.52-7.34 (m, 3H), 6.79-6.66 (m, 2H), 6.66-6.58 (m, 1H), 4.94 (s, 1H), 4.83-4.72 (m, 2H), 4.16-3.96 (m, 2H), 3.89-3.76 (m, 6H), 3.12-2.99 (m, 2H), 2.25-2.12 (m, 2H), 1.68 (t, J=8.5 Hz, 2H), 1.20 (t, J=1.7 Hz, 9H), 0.73-0.61 (m, 2H). MALDI-TOF (Dithranol matrix, M$^+$): m/z 748.

N-(methyl)-N'-(6-aza-4-oxa-5-oxo-9-trimethoxysi-lyl-nonan)-1,13-dimethoxyquinacridinium tetrafluoroborate 7

7

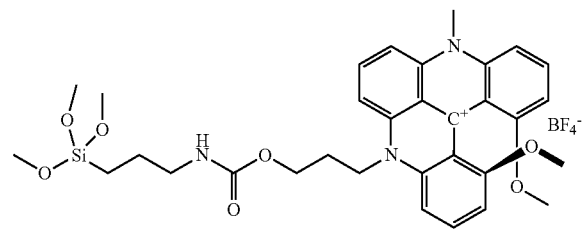

9-(methyl)-1,8-dimethoxy-10-(2,6-dimethoxyphenyl)-acridium (70 mg, 0.143 mmol) was dissolved in 8 ml anhydrous acetonitrile and then 3-(triethoxysilane)propyl isocyanate (cold, 100 ul, d=0.999 g/ml, 0.404 mmol) was added. The flask was fitted with a stopper and stirred at room temperature for 4 h. After 4 h MALDI-TOF analysis indicated that the reaction mixture only contained starting material. Then excess of isocyanate (1 ml) was added together with approx. 1 ml of triethylamine. The mixture was heated to 65° C. and stirred for 1.5 h. Then MALDI-TOF analysis indicated that the reaction mixture contained a compound with a mass of 649 m/z, which is the mass of the desired product, and no mass corresponding to that of the starting material was present. The reaction mixture was washed (still warm) with heptane (2×50 ml) and then dried over $MgSO_4$ for 10 min. The solvent was removed by evaporation at 50° C. in vacuum and the crude product was dissolved in a minimum of $CH_2Cl_2$ and then diethyl ether (200 ml) was added and a green precipitate was allowed to form. The dark product was collected and dried in vacuum over KOH over night. Yield: 80 mg (76%).

$^1$H NMR (500 MHz, DMSO-$d_6$) δ 8.26 (t, J=8.5 Hz, 1H), 8.04-7.87 (m, 2H), 7.73-7.56 (m, 4H), 7.34 (t, J=5.9 Hz, 1H), 7.04 (dd, J=8.1, 4.1 Hz, 2H), 4.86 (d, J=16.5 Hz, 1H), 4.62 (s, 1H), 4.35-4.21 (m, 2H), 4.17 (s, 3H), 3.79-3.69 (m, 12H), 3.01 (q, J=6.7 Hz, 2H), 2.26 (d, J=28.9 Hz, 2H), 1.50 (dq, J=12.8, 7.7 Hz, 2H), 1.13 (q, J=6.7 Hz, 9H), 0.60-0.53 (m, 2H). MALDI-TOF (Dithranol matrix): m/z 649.

Scheme 4 shows the structure of the pH responsive and the reference dyes disclosed herein.

Scheme 4. Molecular structures of the pH responsive and the reference dyes measured in the sol-gel material.

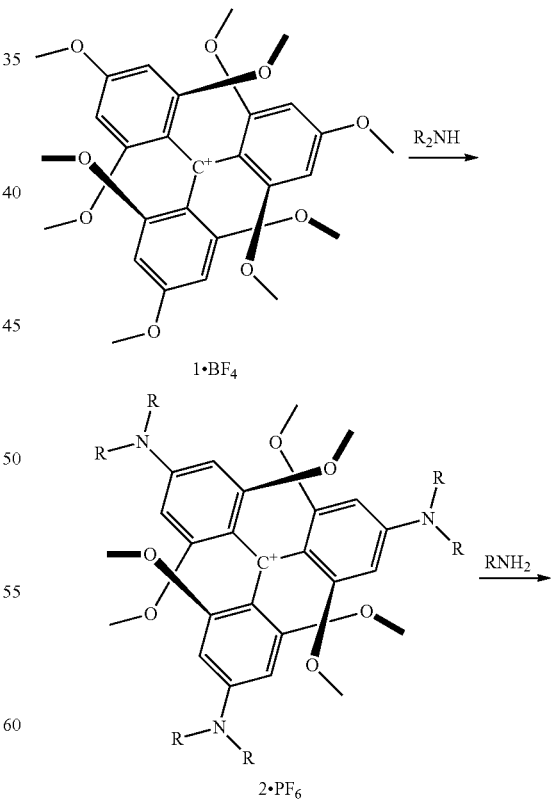

2a: R = $C_6H_{13}$
2b: R = $CH_3$
2c: R = $C_2H_5$

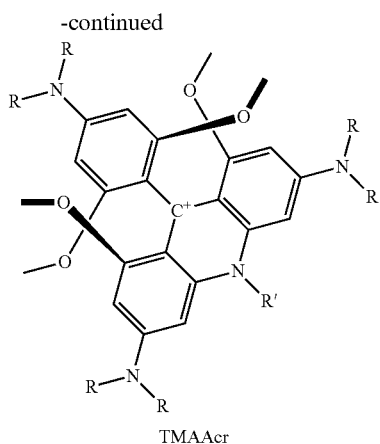

TMAAcr

-1: R = C₆H₁₃, R' = CH₃
-2: R = CH₃, R' = C₃H₆OH
-3: R = CH₃, R' = C₃H₆OCONHC₃H₆Si(OC₂H₅)₃
-4: R = C₂H₅, R' = C₁₂H₂₅
-5: R = C₂H₅, R' = C₁₂H₂₄NH₂
-6: R = C₂H₅, R' = C₁₂H₂₄NHCONHC₃H₆Si(OC₂H₅)₃

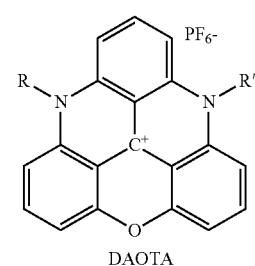

DMQA

-1: R = R' = C₈H₁₇
-2: R = CH₃, R' = C₃H₆OCONHC₃H₆Si(OC₂H₅)₃

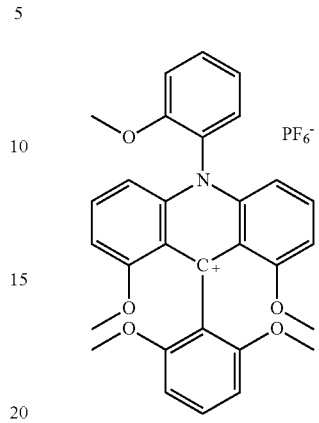

DAOTA

-1: R = C₇H₇SO₃, R' = C₃H₆OCONHC₃H₆Si(OC₂H₅)₃
-2: R = C₇H₇SO₃, R' = C₁₂H₂₅

9-(2,6-dimethoxyphenyl)-1,8-dimethoxy-10-(2-methoxyphenyl)-9,10-dihydroacridinium hexafluorophosphate (MR-68-Acr)

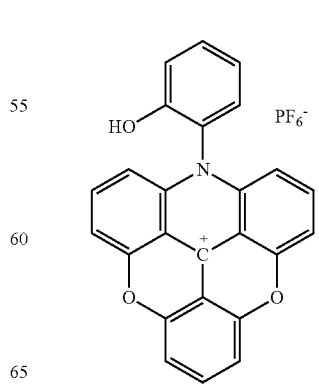

(DMP)₃C⁺BF₄⁻ (2.0 g, 3.9 mmol) was dissolved in CH₃CN (30 ml). This solution was added drop wise to a mixture of o-anisidine (0.57 ml 5.10 mmol) in 2,6-lutidine (3 ml, 27.4 mmol) heated to a temperature of 75° C. When the addition was complete the reaction was allowed to proceed over night. The reaction mixture was allowed to cool down and then poured into a KPF₆ solution (0.2 M, 300 ml) upon stirring. The precipitate was allowed to form and then filtered off and washed several times with water. The red solid material was dissolved in CH₂Cl₂ and the organic phase was dried over MgSO₄. The crude product was collected by evaporation of the solvent in vacuum. The product was dissolved in a minor volume CH₃CN and upon stirring diethyl ether was added until a precipitate formed. The precipitate was allowed to form for 2 h and then collected by filtration. The red solid was recrystallized from methanol yielding dark red crystals.

Yield: 1.19 g (48%). ¹H NMR (500 MHz, DMSO-d₆) δ 8.10 (2H), 7.89 (1H), 7.80 (1H), 7.62 (1H), 7.51-7.43 (2H), 7.22 (1H), 6.92 (2H), 6.85 (2H), 3.69 (3H), 3.61 (3H), 3.58 (3H), 3.56 (6H). ¹³C NMR (125 MHz, DMSO) δ 159.89, 158.21, 155.52, 155.11, 153.54, 142.08, 140.37, 133.34, 129.62, 129.03, 125.99, 122.52, 119.04, 118.66, 114.20, 110.00, 107.07, 103.76, 57.25, 56.34, 55.98, 55.95. (1 signal is missing.) MS: 468.20.

4-(2-hydroxyphenyl)-4-aza-8,12-dioxatriangulenium hexafluorophophate (MR-68.1-ADOTA)

Pyridinium hydrochloride (30 g, 260 mmol) was heated to 190-200° C. for 30 min. MR-68_Acr (1.8 g, 2.9 mmol) was added in one portion into the molten pyridinium hydrochloride. The reaction was allowed to proceed at 190-200° C. for 3 h. The heat was removed and the mixture was allowed to cool to ambient temperatures. The mixture was suspended in water and this suspension was poured into acidified $KPF_6$ solution upon stirring. The precipitate was filtered off. The red solid was suspended in acetonitrile and this suspension was heated to refluxing conditions, filtered, and the solvent was removed in vacuum. The material was purified by column chromatography ($CH_2Cl_2$:$CH_3OH$, 92:8). The orange powder was dissolved in a minor volume $CH_2Cl_2$, which was washed with an equal volume acidified $KPF_6$ solution, dried over $Na_2SO_4$, filtered, and the solvent was removed in vacuum. Yield: 290 mg (19%). $^1$H NMR (500 MHz, DMSO-$d_6$) δ 10.57 (1H), 8.34-8.19 (3H), 7.72 (2H), 7.71 (2H), 7.67 (1H), 7.51 (1H), 7.35 (1H), 7.26 (1H), 6.95 (2H). $^{13}$C NMR (125 MHz, DMSO-$d_6$) δ 153.07, 152.53, 152.18, 141.53, 141.23, 141.02, 140.21, 132.70, 129.00, 122.79, 121.28, 118.31, 111.76, 110.74, 109.35, 108.32, 105.90. MS: 376.09.

4-(2-hydroxyphenyl)-8-methyl-4,8-diaza-12-oxatriangulenium hexafluorophosphate (MR-68-DAOTA)

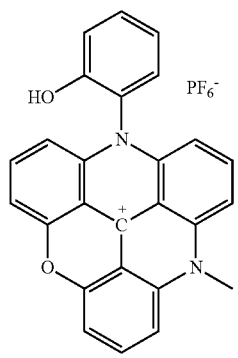

MR-68.1_ADOTA (230 mg, 0.441 mmol) and benzoic acid (1.5 g, 12 mmol) were suspended in a mixture of NMP (1.5 ml) and methylamine in abs. ethanol (1.5 ml, 33 wt %, 12 mmol). The flask was fitted with a condenser equipped with a balloon. The mixture was heated to 100° C. for 20 h. The mixture was allowed to cool to ambient temperatures and the mixture was then poured into a stirred acidified $KPF_6$ solution. The mixture was filtered and the precipitate was washed with diethyl ether. The purple material was collected and purified by dry vacuum column chromatography ($CH_2Cl_2$:$CH_3OH$, 0.5% gradient) The material was dissolved in a minor volume $CH_2Cl_2$, which was washed with acidified $KPF_6$ solution. The organic phase was dried over $Na_2SO_4$, filtered, and the solvent was removed in vacuum. The finely powdered purple material yielded 70 mg (30%). $^1$H NMR (500 MHz, DMSO-$d_6$) δ 10.40 (1H), 8.21-8.06 (2H), 7.98 (1H), 7.80 ($^1$H), 7.69-7.54 (2H), 7.48-7.37 (3H), 7.32 (1H), 7.24 (1H), 6.66 (1H), 6.60 (1H), 4.06 (3H). $^{13}$C NMR (126 MHz, DMSO-$d_6$) δ 153.30, 152.13, 151.90, 141.63, 140.98, 140.54, 140.33, 139.90, 139.48, 138.63, 138.43, 132.23, 129.35, 123.31, 121.38, 118.43, 110.85, 109.89, 109.83, 108.41, 108.31, 107.49, 107.08, 106.44, 106.37, 35.60.

9-(2,6-dimethoxyphenyl)-1,8-dimethoxy-10-(3-methoxyphenyl)-9,10-dihydroacridinium hexafluorophosphate (MR-73_Acr)

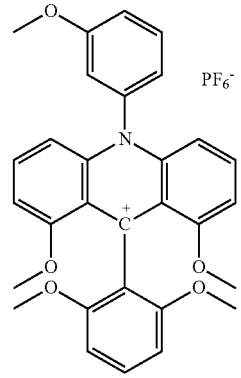

Prepared following procedure analogous to that described for MR-68_Acr. $(DMP)_3C^+BF_4^-$ (5.0 g), m-anisidine (1.57 g) in 2,6-lutidine (8 ml). Red crystals, yield: 3.45 g (56%). $^1$H NMR (500 MHz, DMSO-$d_6$) δ 8.09 (2H), 7.80 (1H), 7.53 (1H), 7.47 (1H), 7.43 (1H), 7.37 (1H), 7.21 (2H), 6.94 (2H), 6.85 (2H), 3.85 (3H), 3.60 (3H), 3.58 (3H), 3.55 (6H). $^{13}$C NMR (126 MHz, DMSO-$d_6$) δ 161.23, 159.74, 157.63, 155.44, 155.34, 142.11, 139.74, 139.47, 132.08, 129.55, 119.82, 119.02, 118.76, 117.34, 113.47, 110.95, 106.79, 103.78, 103.76, 57.24, 55.94, 55.93, 55.86. MS: 482.20.

4-(3-hydroxyphenyl)-4-aza-8,12-dioxatriangulenium hexafluorophophate (MR-73-ADOTA)

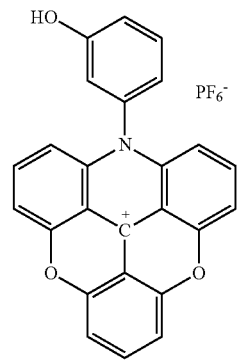

Prepared following procedure analogous to that described for MR-68_ADOTA. Pyridinium hydrochloride (23 g) and MR-73_Acr (1.3 g) reacted at 190-200° C. for 3 h. Purified by column chromatography ($CH_2Cl_2$:$CH_3OH$, 92:8) yielding a orange-red powder. Yield: 590 mg (55%). $^1$H NMR (500 MHz, DMSO-$d_6$) δ 10.41 (1H), 8.26 (3H), 7.79-7.63 (5H), 7.23 (1H), 7.05 (1H), 7.01-6.99 (1H), 6.97 (2H). $^{13}$C NMR (126 MHz, DMSO) δ 160.20, 152.31, 152.07, 141.36, 140.87, 140.28, 137.39, 132.78, 118.25, 117.71, 114.25, 111.89, 111.13, 109.28, 108.30, 105.64. (1 signal is missing). MS: 376.20.

4-(3-hydroxyphenyl)-8-methyl-8-aza-8,12-dioxatriangulenium hexafluorophosphate (MR-73.1-DAOTA)

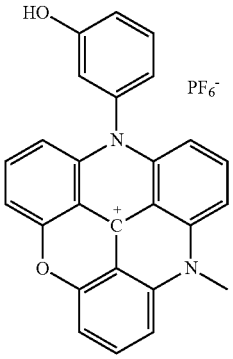

Prepared following procedure analogous to that described for MR-68_DAOTA. MR-73.1_ADOTA (400 mg) and benzoic acid (5.0 g), NMP (5 ml), and methylamine in abs. ethanol (5 ml, 33 wt %). Purified by column chromatography (CH$_2$Cl$_2$:CH$_3$OH, 94:6). Yield: 110 mg (27%). $^1$H NMR (500 MHz, DMSO-d$_6$) δ 10.32 (1H), 8.19 (1H), 8.14 (1H), 7.98 (1H), 7.83 (1H), 7.72-7.62 (2H), 7.48 (1H), 7.44 (1H), 7.19 (1H), 6.99 (1H), 6.93 (1H), 6.67 (1H), 6.61 (1H), 4.08 (3H). $^{13}$C NMR (126 MHz, DMSO) δ 160.40, 152.09, 151.79, 141.81, 140.88, 140.64, 140.31, 139.99, 139.32, 138.70, 138.26, 138.04, 132.92, 117.98, 117.79, 114.51, 110.83, 110.19, 110.00, 108.39, 108.34, 107.43, 107.08, 106.73, 106.35, 35.63. MS: 389.13.

9-(2,6-dimethoxyphenyl)-1,8-dimethoxy-10-(4-methoxyphenyl)-9,10-dihydroacridinium hexafluorophosphate (MR-93_Acr)

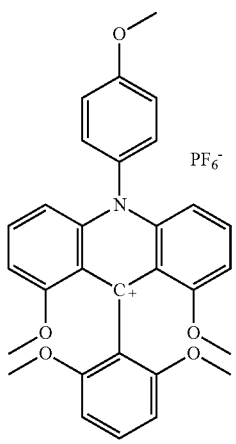

Prepared following procedure analogous to that described for MR-93_Acr. (DMP)$_3$C$^+$BF$_4^-$ (3 g) in CH$_3$CN (80 ml), p-anisidine (1.0 g), 2,6-lutidine (5 ml). The red solid was recrystallized from methanol yielding shinny red crystals. Yield: 2.74 g (74%). $^1$H NMR (500 MHz, DMSO-d$_6$) δ 8.08 (2H), 7.78-7.71 (2H), 7.47 (1H), 7.44-7.37 (2H), 7.20 (2H), 6.94 (2H), 6.85 (2H), 3.97 (3H), 3.58 (6H), 3.55 (6H). $^{13}$C NMR (126 MHz, DMSO-d$_6$) δ 160.83, 159.79, 157.53, 155.43, 142.80, 139.69, 131.05, 129.59, 129.32, 119.12, 118.82, 116.35, 111.01, 106.82, 103.80, 57.26, 55.97, 55.87. MS: 482.20.

4-(4-hydroxyphenyl)-4-aza-8,11-dioxatriangulenium hexafluorophosphate (MR-93_ADOTA

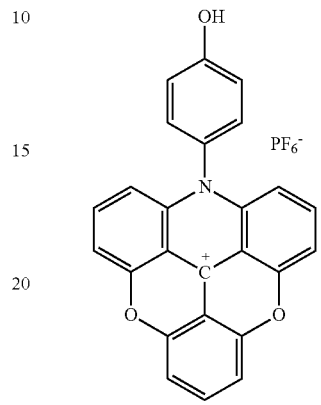

Prepared following procedure analogous to that described for MR-68_ADOTA. Pyridinium hydrochloride (22 g), MR-93_Acr (1.52 g) was allowed to react at 190-200° C. for 2 h. The material was recrystallized from absolute ethanol-methanol mixture yielding red crystals. Yield: 630 mg (50%). $^1$H NMR (500 MHz, DMSO-d$_6$) δ 10.39 (1H), 8.33-8.15 (3H), 7.71 (4H), 7.50-7.37 (2H), 7.26-7.14 (2H), 6.97 (2H). $^{13}$C NMR (126 MHz, DMSO-d$_6$) δ 159.39, 152.32, 152.06, 142.04, 141.19, 140.77, 140.20, 129.09, 127.42, 118.09, 111.85, 111.25, 109.22, 108.34, 105.65. MS: 376.10.

4-(4-hydroxyphenyl)-4,8-diaza-11-oxatriangulenium hexafluorophosphate (MR-93_DAOTA)

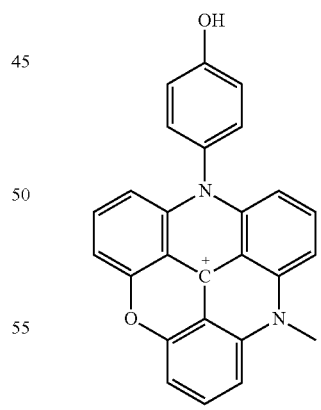

Prepared following procedure analogous to that described for MR-68_DAOTA. MR-93_ADOTA (500 mg) and benzoic acid (2.5 g) in NMP (2.5 ml) and methylamine in abs. ethanol (2.5 ml, 33 wt %). The purple solid was purified by column chromatography (CH$_2$Cl$_2$:CH$_3$OH, 96:4). Yield: 210 mg (41%). $^1$H NMR (500 MHz, DMSO-d$_6$) δ 10.31 (1H), 8.19-8.09 (2H), 7.96 ($^1$H), 7.79 (1H), 7.62 (1H), 7.45-7.39 (2H), 7.39-7.32 (2H), 7.23-7.16 (2H), 6.66 (1H), 6.61 (1H), 4.04 (3H). $^{13}$C NMR (126 MHz, DMSO-d$_6$) δ 159.03, 152.04, 151.77, 142.48, 141.29, 140.87, 140.26, 139.82, 139.30, 138.66, 138.23, 129.38, 128.03, 118.31, 110.84, 110.32, 109.94, 108.36, 108.30, 107.33, 107.05, 106.86, 106.29, 35.60. MS: 389.13.

9-(2,6-dimethoxyphenyl)-1,8-dimethoxy-10-(2-methoxy-5-(trifluoromethyl)phenyl)-9,10-dihydroacridinium hexafluorophosphate (MR-66_Acr)

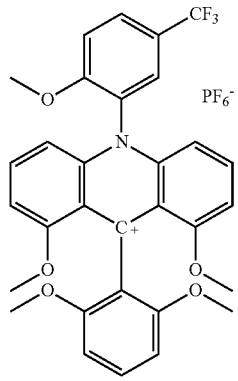

Prepared following procedure analogous to that described for MR-68_Acr. (DMP)$_3$C$^+$BF$_4^-$ (20.7 g), CH$_3$CN (250 ml), 2-methoxy-5-(trifluoromethyl)aniline (11 g), 2,6-lutidine (35 ml). The red solid was recrystallized from methanol. Yield: 13.70 g (49%). $^1$H NMR (500 MHz, DMSO-d$_6$) δ 8.46 (1H), 8.29 (1H), 8.10 (2H), 7.81 (1H), 7.48 (1H), 7.22 (2H), 6.92 (2H), 6.86 (2H), 3.79 (3H), 3.61 (3H), 3.58 (3H), 3.56 (6H). $^{13}$C NMR (126 MHz, DMSO-d$_6$) δ 160.05, 158.82, 156.69, 155.56, 155.05, 142.04, 140.70, 130.71 (d), 129.66, 127.12 (q), 126.31, 124.55 (q), 119.06, 118.67, 115.24, 109.83, 107.12, 103.83, 103.78, 57.29, 57.13, 55.98, 55.96. MS: 550.18.

4-(2-hydroxy-5-(trifluoromethyl)phenyl)-3-aza-8,11-dioxatriangulenium hexafluorophosphate (MR-66.1_ADOTA)

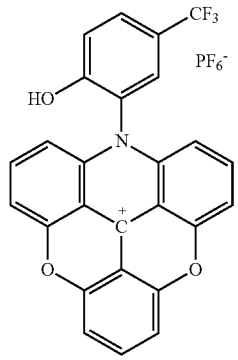

Prepared following procedure analogous to that described for MR-68_ADOTA. Pyridinium hydrochloride (20 g), MR-66_Acr (2.0) was reacted for 20 min at 180-200° C. The red product was recrystallized from absolute ethanol with a minor added volume of acetonitrile. Yield: 794 mg (47%).

$^1$H NMR (500 MHz, DMSO-d$_6$) □ 11.60 (1H), 8.28 (3H), 8.09-8.01 (2H), 7.75 (2H), 7.73 (2H), 7.51 (1H), 6.99 (2H). $^{13}$C NMR (125 MHz, DMSO) δ 156.93, 152.59, 152.22, 141.77, 141.32, 141.14, 140.44, 129.99 (q), 127.21 (q), 123.12, 124.02 (q), 121.52 (q), 119.23, 111.84, 110.64, 109.56, 108.21, 105.89. MS: 444.08.

4-(2-hydroxy-5-(trifluoromethyl)phenyl)-8-methyl-8-aza-11-oxatriangulenium hexafluorophosphate (MR-66_DAOTA)

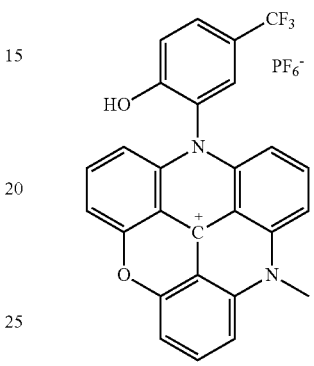

Prepared following procedure analogous to that described for MR-68_DAOTA. MR-66_ADOTA (570 mg) and benzoic acid (5 g) in NMP (5 ml) and cold methylamine in abs. ethanol (33% wt, 5 ml). The purple material was collected and purified by column chromatography (CH$_2$Cl$_2$:CH$_3$OH, 96:4) Yield: 190 mg (33%). $^1$H NMR (500 MHz, DMSO-d$_6$) δ 11.45 (1H), 8.20 (1H), 8.16 (1H), 8.04-7.95 (3H), 7.86 (1H), 7.69 (1H), 7.53-7.43 (3H), 6.67 (1H), 6.60 (1H), 4.10 (3H). $^{13}$C NMR (125 MHz, DMSO-d$_6$) δ 157.22, 152.16, 151.97, 141.49, 141.06, 140.44, 140.40, 140.04, 139.67, 138.82, 138.65, 127.59 (q), 129.53 (q), 124.00 (q), 123.69, 121.69 (q), 119.30, 110.83, 110.07, 109.68, 108.64, 108.43, 107.59, 107.04, 106.75, 106.22, 35.73. MS: 457.12.

9-(2,6-dimethoxyphenyl)-1,8-dimethoxy-10-(3-methoxy-5-(trifluoromethyl)phenyl)-9,10-dihydroacridinium hexafluorophosphate: (MR-67.1_Acr)

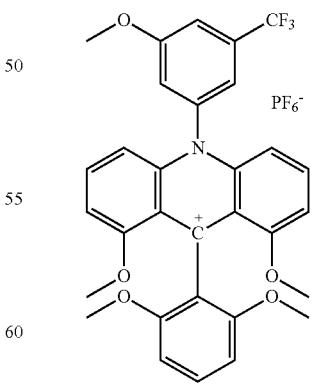

Prepared following procedure analogous to that described for MR-68_Acr. (DMP)$_3$C$^+$BF$_4^-$ (4.0 g), CH$_3$CN (80 ml), 3-methoxy-5-(trifluoromethyl)aniline (2.0 g), 2,6-lutidine (7 ml). The red solid was recrystallized from methanol yielding red crystals. Yield: 3.2 g (59%). $^1$H NMR (500 MHz, DMSO-d$_6$) δ 8.09 (2H), 8.01 (1H), 7.93 (1H), 7.78 (1H), 7.48 (1H), 7.22 (2H), 6.92 (2H), 6.86 (2H), 3.94 (3H), 3.59 (2H), 3.59 (3H), 3.56 (5H). $^{13}$C NMR (125 MHz, DMSO-d$_6$) δ 161.78, 159.90, 158.14, 155.41, 155.38, 142.18, 140.31, 139.99, 132.82 (q), 129.58, 123.32 (q), 119.06, 118.79, 118.23, 117.14 (q), 114.24 (q), 110.84, 106.79, 103.87, 103.79, 57.27, 56.59, 55.94, 55.93. MS: 550.18.

4-(3-hydroxy-5-(trifluoromethyl)phenyl)-4-aza-8,11-dioxatriangulenium hexafluorophosphate (MR-67.1_ADOTA)

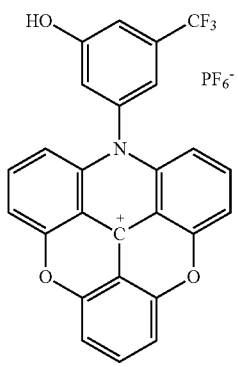

Prepared following procedure analogous to that described for MR-68_ADOTA. Pyridinium hydrochloride (30 g) and MR-67_Acr (1.51 g) was allowed to react at 180-200° C. for 2 h. Purified by column chromatography (CH$_2$Cl$_2$:CH$_3$OH, 92:8). Yield: 830 mg (65%). $^1$H NMR (500 MHz, DMSO-d$_6$) δ 11.18 (1H), 8.28 (3H), 7.75 (4H), 7.59-7.53 (1H), 7.54-7.47 (1H), 7.38-7.33 (1H), 7.00 (2H). $^{13}$C NMR (126 MHz, DMSO-d$_6$) δ 161.03, 152.34, 152.11, 141.52, 141.36, 141.15, 140.51, 138.39, 133.35 (q), 123.37 (q), 119.09, 114.89, 111.99, 111.12, 109.48, 108.18, 105.58. MS: 444.08.

4-(3-hydroxy-5-(trifluoromethyl)phenyl)-4-methyl-4,11-diaza-8-oxa triangulenium hexafluorophosphate (MR-67.1_DAOTA)

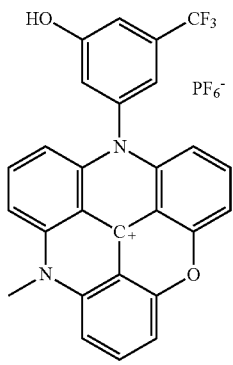

Prepared following procedure analogous to that described for MR-68_DAOTA. MR-67_ADOTA (600 mg), benzoic acid (5.0 g), NMP (5 ml), and methylamine in abs. ethanol (5 ml, 33 wt %). The purple material was collected and purified by column chromatography (CH$_2$Cl$_2$:CH$_3$OH, 96:4). The purple material yielded 300 mg (49%)$^1$H NMR (500 MHz, DMSO-d$_6$) δ 11.06 (1H), 8.22 (1H), 8.15 (1H), 7.99 (1H), 7.87 (1H), 7.69 (1H), 7.55-7.40 (4H), 7.31 (1H), 6.68 (1H), 6.61 (1H), 4.11 (3H). $^{13}$C NMR (126 MHz, DMSO) δ 161.11, 152.06, 151.81, 141.75, 140.90, 140.61, 140.34, 140.04, 139.53, 139.08, 138.87, 138.49, 133.56 q), 123.42 (q), 119.45, 115.43-115.24 (m), 114.43-114.28 (m), 110.79, 110.16, 110.13, 108.57, 108.52, 107.44, 107.00, 106.68, 106.64, 35.74. MS: 457.12.

9-(2,6-dimethoxyphenyl)-1,8-dimethoxy-10-(2-methoxy-5-nitrophenyl)-9,10-dihydroacridinium hexafluorophosphate: (MR-69.1)

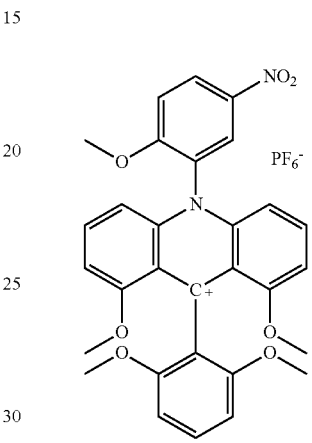

Prepared following procedure analogous to that described for MR-68_Acr. DMP$_3$C$^+$BF$_4^-$ (2 g, 4 mmol), acetonitrile (70 ml), 2-methoxy-5-nitroaniline (3.0 g) in 2,6-lutidine (5 ml). The purple material was recrystallized from methanol yielding dark crystals, 1.48 g (56%). $^1$H NMR (500 MHz, DMSO-d$_6$) δ 9.03 (1H), 8.77 (1H), 8.07 (2H), 7.82 (1H), 7.48 (1H), 7.22 (1H), 7.05 (2H), 6.87 (1H), 6.84 (1H), 3.84 (3H), 3.63 (3H), 3.57 (3H), 3.56 (6H). $^{13}$C NMR (125 MHz, DMSO-d$_6$) δ 160.06, 159.03, 158.90, 155.64, 155.00, 142.08, 141.96, 140.62, 129.67, 129.05, 126.20, 126.03, 119.11, 118.71, 114.82, 110.02, 107.14, 103.83, 103.81, 57.73, 57.29, 56.00, 55.97. MS: 527.18.

3-(2-hydroxy-5-nitrophenyl)-7,10-dioxa-3-azatriangulenium hexafluorophosphate (MR-69.1_ADOTA)

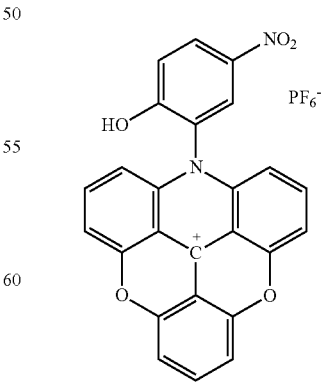

Prepared following procedure analogous to that described for MR-68_ADOTA. Pyridinium hydrochloride (12 g) and MR-69.1_Acr (430 mg) was reacted at 190° C. for 30 min. The material was purified by column chromatography (CH$_2$Cl$_2$:CH$_3$OH, 96:4). The orange-red solid yielded 90 mg (25%). $^1$H NMR (500 MHz, DMSO-d$_6$) δ 12.25 (1H), 8.63 (1H), 8.57 (1H), 8.33-8.22 (3H), 7.75 (4H), 7.48 (1H), 7.11 (2H). $^{13}$C NMR (125 MHz, DMSO) δ 159.98, 157.91, 152.60, 152.23, 141.90, 141.24, 141.11, 140.51, 128.63, 126.77, 122.92, 118.77, 111.86, 110.79, 109.63, 108.22, 105.90. MS: 421.08

4-(2-hydroxy-5-nitrophenyl)-8-methyl-8-aza-11-oxatriangulenium hexafluorophosphate (MR-69_DAOTA)

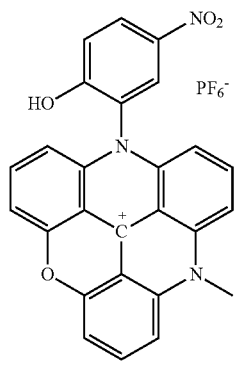

Prepared following procedure analogous to that described for MR-68_ADOTA. MR-69.1_ADOTA (80 mg) and benzoic acid (600 mg), NMP (0.6 ml), and methylamine in abs. ethanol (0.6 ml, 33 wt %). Purified by column chromatography (CH$_2$Cl$_2$:CH$_3$OH, 94:6). Yield: 10 mg (12%). $^1$H NMR (500 MHz, DMSO-d$_6$) □ 12.12 (1H), 8.56 (1H), 8.51 (1H), 8.22 (1H), 8.14 ($^1$H), 7.97 (1H), 7.88 (1H), 7.70 (1H), 7.52 (1H), 7.47 (1H), 7.43 (1H), 6.79 (1H), 6.72 (1H), 4.12 (3H). $^{13}$C NMR (125 MHz, DMSO-d$_6$) δ 152.17, 151.97, 141.44, 141.05, 140.41, 140.40, 140.11, 139.57, 138.85, 138.54, 128.23, 127.15, 123.55, 118.95, 110.83, 110.09, 109.84, 108.70, 108.45, 107.64, 107.06, 106.84, 106.39, 35.76.

TABLE 1

| Compound | $\varepsilon_{max}$(M$^{-1}$cm$^{-1}$) | $\lambda_{abs\square max}$ (nm) | $\lambda_{\square\square\square max}$ (nm) | $\eta_\square$ (%) | p$\square_\square$ |
|---|---|---|---|---|---|
| MR-93_DAOTA | 14400/*14100* | 555/*560* | 591/*591* | >99 | 8.6 |
| MR-73.1_DAOTA | 13600/*13500* | 554/*559* | 590/*590* | 99 | 8.5 |
| MR-68_DAOTA | 13000/*12900* | 554/*559* | 588/*590* | >99 | 7.6 |
| MR-67.1_DAOTA | 14700/*14300* | 553/*557* | 586/*588* | 99 | 7.3 |
| MR-66_DAOTA | 16600/*16600* | 553/*558* | 585/*588* | >99 | 6.2 |
| MR-69_DAOTA | 16500/*16300* | 553/*557* | 586/*589* | 74 | 4.4 |

Molar absorption coefficients given in M$^{-1}$cm$^{-1}$, wavelength at maximum absorption of the lowest energy transition ($\lambda_{abs\square max}$) given in nanometers (nm), wavelength at the maximum fluorescence intensity ($\lambda_{\square\square\square max}$) given in nm, quenching efficiency of the fluorescence intensity ($\eta_\square$) given in percentage (%).
Numbers given in italics are values related to of the deprotonated form of the compound.

Preparation of Sol-Gel Matrix

The procedure includes preparation of two separate gel components of the organic modified silanes: Ethyltriethoxysilane (ETEOS) and 3-(glycidoxy)propyltrimethoxysilane (GPTMS) and the admixture to one of these components of compound 6 or 7.

ETEOS

The ETEOS gel component is prepared from polymerization of the silicon network under acidic conditions. ETEOS is hydrolysed under acidic conditions, which initiates a polymeric condensation reaction upon formation of a polymer silicon oxide network. The presented procedure is an equivalent to the procedure reported by Wencel et al. (D. Wencel, B. D. MacCraith and C. McDonagh, *Sensors and Actuators B: Chemical*, 2009, 139, 208-213, and D. Wencel, M. Barczak, P. Borowski and C. McDonagh, *J. Mater. Chem.*, 2012, 22, 11720).

Procedure for preparation of ETEOS gel component: 5 ml ETEOS (0.02 mol) is dissolved in 8 ml absolute ethanol (0.14 mol) upon stirring. Hereafter, 1.6 ml of 0.1 M HCl solution (0.16 mmol) is added dropwise. This mixture is then left on a stirring table for a minimum of 7 days to allow the polymerization process to proceed.

GPTMS Gel Component.

The GPTMS gel component is prepared from polymerization of the organic linker using a Lewis acid as initiator. In this procedure we use boron trifluoride diethyletherate as the Lewis acid. The Lewis acid attacks the epoxy ring that allows for ring opening of the epoxy ring upon formation of a secondary carbocation. This intermediate carbocation can then react with another GPTMS molecule, initiating a polymerization reaction. Due to the acidic environment a polymerization of the silicon network equivalent to that described for the ETEOS component will proceed alongside.

Procedure for preparation of GPTMS gel component: 6 ml of GPTMS (0.027 mol) is mixed with 11 ml of absolute ethanol (0.19 mol) upon stirring. Then 0.75 ml of cold borontrifluoride diethyletherat (BF$_3$.O(CH$_2$CH$_3$)$_2$, 5.8 mmol) is added dropwise. The mixture is left with stirring for 30 min in a sealed container until the temperature of the mixture has dropped to room temperature. After 30 min 2 ml of MilliQ water (0.11 mol) is added to the solution. The resulting mixture was left with stirring for 4 h.

When the two gel components have been prepared they are mixed in 1:1 molar ratio and left for a minimum of 3 days to allow the networks to mix. This is referred to as the GPTMS-ETEOS mixture.

The compounds according to 6 or 7 are mixed into either the ETEOS or the GPTMS gel component 1 h after mixing of the materials described. Subsequently, the ETEOS or the GPTMS gel components are mixed. The two components are then mixed in 1:1 molar ratio and left at a stirring table for no less than 3 days. The dyes 6 or 7 are added in an amount so that a final concentration of 0.1 mM of dye is obtained in the final GPTMS-ETEOS mixture. The resulting GPTMS-ETEOS-dye mixture is then deposited and cured at 110° C. for 3-4 hours.

pH Properties of the DAOTA Dyes in Sol Gel Matrix

8-(3-(N-methylamino)propyl-4,8-diazatriangulenium-4-(4-(trifluoromethyl)phenolate) (MR-66_DAOTANH.1)

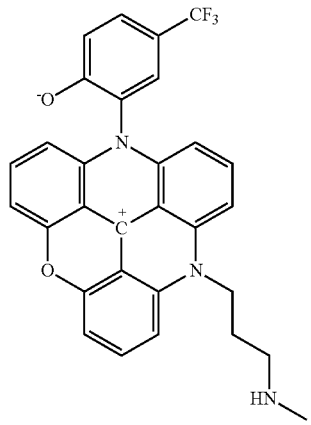

MR-66_ADOTA (2.05 g) was dissolved in NMP (10 ml) and heated to 100° C. Then N-methyl-1,3-diaminopropane (2 ml) was added. The reaction mixture heated to 120° C. for 45 min. The hot solution was poured into water (400 ml). The purple product was extracted with CH$_2$Cl$_2$ and the solvent of the organic phase was removed in vacuum. The residue was dissolved in a minor volume CH$_2$Cl$_2$ and then poured into stirring diethyl ether (500 ml). The precipitate filtered off. The solid was washed with diethyl and purified by dry vacuum column chromatography (CH$_2$Cl$_2$:triethylamine, 99:1 to CH$_3$OH:Triethylamine, 99:1, 10% gradient, CH$_3$OH:CH$_3$COOH, 10% gradient, then CH$_3$COOH:H$_2$O, 10% gradient). Yield: 500 mg (28%). $^1$H NMR (500 MHz, CD$_3$OD) □ 8.07 (2H), 7.89 (1H), 7.66 (1H), 7.59 (1H), 7.50 (1H), 7.42 (1H), 7.32 (2H), 7.27 (1H), 7.00 (1H), 6.88 (2H), 6.85 (1H), 4.61 (2H), 2.84 (2H), 2.46 (3H), 2.12 (3H)$^{13}$C NMR (125 MHz, MeOD) □ 168.78, 154.48, 153.78, 144.42, 143.02, 141.93, 141.70, 141.41, 140.35, 139.52, 139.02, 129.80, 129.69 (q), 127.31 (q), 126.59, 125.50 (q), 124.42, 115.68 (q), 113.32, 111.82, 110.10, 109.52, 109.34, 109.10, 109.10, 108.66, 106.39, 56.06, 46.87, 36.33, 26.57. MS: 514 [M+H$^+$].

8-(1-methyl-1-propyl-3-(3-(triethoxysilyl)propyl) urea)-4,8-diazatriangulenium-4-(4-(trifluoromethyl) phenolate) (I1C)

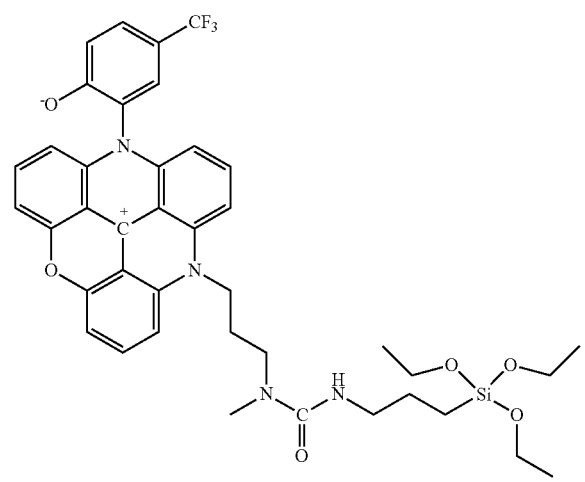

MR-66_DAOTANH.1 (222 mg) was dissolved in CH$_2$Cl$_2$ (6 ml) and 3-isocyanatopropyltriethoxysilane (110 μl) was added. The mixture was stirred for 15 min and then heptane (20 ml, HPLC grade) was added. The CH$_2$Cl$_2$ was removed in vacuum and the resulting precipitate in the heptane was filtered off. The residue was washed with 50 ml of heptane and dried in vacuum over night. Yield: 300 mg (91%). $^1$H NMR (500 MHz, CD$_3$OD) δ 8.04 (1H), 7.88 (2H), 7.60 (1H), 7.46 (1H), 7.40 (1H), 7.36 (1H), 7.18 (1H), 7.13 (1H), 7.01 (1H), 6.85 (2H), 4.43-4.25 (2H), 3.80 (6H), 3.54 (2H), 3.17 (2H), 2.06 (2H), 1.72-1.52 (2H), 1.18 (9H), 0.70-0.53 (2H). $^{13}$C NMR (125 MHz, CD$_3$OD) δ 168.90, 160.71, 154.08, 153.48, 144.28, 142.89, 141.56, 141.13, 141.02, 140.53, 139.63, 139.18, 129.88-129.67 (m), 127.38-127.14 (m), 126.91 (q), 126.46, 124.56, 115.76, 115.50, 115.37 (q), 115.24, 114.98, 113.03, 112.00, 109.98, 109.58, 109.22, 109.04, 108.86, 108.69, 106.29, 59.52, 46.92, 46.39, 44.69, 35.10, 25.36, 25.00, 18.75, 8.64. MS: 761.

4-(2-hydroxy-5-(methylsulfonyl)phenyl)-4-aza-8,12-dioxatriangulenium hexafluorophosphate (MR-49.6_ADOTA)

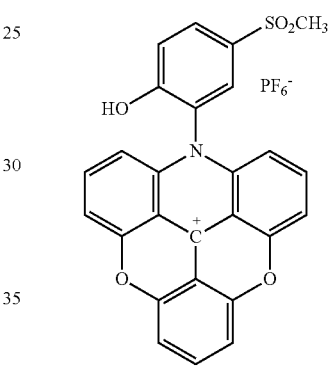

Prepared following procedure analogous to that described for MR-68_ADOTA. Pyridinium hydrochloride (60 g) and MR-49.6_Acr (6.0 g) was allowed to react at 190-200° C. for 1 h. Yield: 3 g (58%).

8-(3-(N-methylamino)propyl-4,8-diazatriangulenium-4-(4-(methylsulfonyl)phenolate) (MR-49.6_DAOTANH)

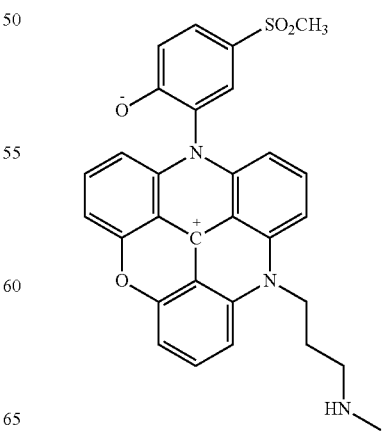

Prepared following procedure analogous to that described for MR-66_DAOTANH.1. MR-49.6_ADOTA (2.3 g), NMP (10 ml), N-methyl-1,3-diaminopropane (2 ml) was added. The purple product was purified using dry vacuum column chromatography ($CH_2Cl_2$:triethylamine, 99:1 to $CH_3$—OH: Triethylamine, 99:1, 10% gradient, $CH_3OH$:$CH_3COOH$, 10% gradient, then $CH_3COOH$:$H_2O$, 10% gradient). Yield: 490 mg (24%). $^1$H NMR (500 MHz, $CD_3OD$) δ 8.06 (2H), 7.91-7.82 (2H), 7.73 (1H), 7.65 (1H), 7.50 (1H), 7.30 (1H), 7.28-7.22 (1H), 6.99 (1H), 6.92-6.83 (2H), 4.58 (2H), 3.15 (3H), 2.83 (2H), 2.45 (3H), 2.17-2.04 (2H). $^{13}$C NMR (125 MHz, $CD_3OD$) δ 171.03, 154.38, 153.73, 144.24, 142.84, 141.89, 141.63, 141.33, 140.45, 139.62, 139.13, 132.20, 130.58, 126.70, 124.51, 123.59, 113.19, 111.76, 110.17, 109.59, 109.26, 109.19, 109.05, 108.63, 106.57, 46.93, 45.38, 36.38, 26.61. (1 signal is missing). MS: 524.

8-(1-methyl-1-propyl-3-(3-(triethoxysilyl)propyl) urea)-4,8-diazatriangulenium-4-(4-(methylsulfonyl) phenolate) (I2C)

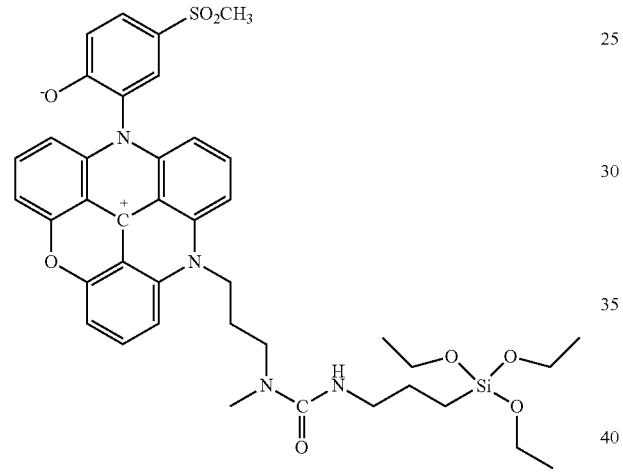

Prepared following procedure analogous to that described for I1C. MR-49.6_DAOTANH (54.8 mg) was dissolved in $CH_2Cl_2$ (4 ml) and 3-isocyanatopropyltriethoxysilane (27 μl) was added. The mixture was stirred for 15 min and then heptane (10 ml) was added. The $CH_2Cl_2$ was removed in vacuum and the resulting precipitate in the heptane was filtered off. The residue was washed with 20 ml of heptane and dried in vacuum over night. Yield: 60 mg (74%). $^1$H NMR (500 MHz, $CD_3OD$) δ 8.05 (1H), 7.96 (1H), 7.91-7.83 (2H), 7.75 (1H), 7.49 (1H), 7.38 (1H), 7.23 (1H), 7.19 (1H), 7.00 (1H), 6.89 (1H), 6.85 (1H), 4.35 (2H), 3.82 (6H), 3.57 (2H), 3.23-3.14 (5H), 2.98 (3H), 2.06 (2H), 1.72-1.56 (2H), 1.20 (9H), 0.70-0.56 (2H). $^{13}$C NMR (125 MHz, $CD_3OD$) δ 171.01, 160.68, 154.09, 153.49, 144.09, 142.72, 141.55, 141.18, 140.98, 140.57, 139.70, 139.24, 132.22, 130.51, 126.52, 124.58, 123.40, 112.92, 111.84, 109.93, 109.63, 109.35, 108.95, 108.74, 108.71, 106.37, 59.49, 46.86, 46.44, 45.44, 44.64, 35.05, 25.30, 24.95, 18.70, 8.59. MS: 771.

1,13-dimethoxy-5,9-bis(3-(methylamino)propyl)-5, 9-dihydro-13bH-quinolino[2,3,4-kl]acridin-13b-ylium hexafluorophosphate (MR-75.4_DMQA)

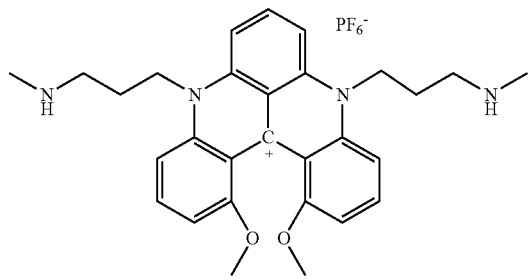

Prepared as described in XXXX. N-methyl-1,3-diaminopropane (150 ml) and $DMP_3C^+PF_6^-$ (10.2 g) in NMP (50 ml) and heated to 90° C. in a 500 ml round-bottomed flask on a water bath. The total reaction time was 1 h. Recrystallized from methanol. Yield: 4.35 g (40%). $^1$H NMR (500 MHz, DMSO-$d_6$) δ 8.25 (1H), 7.95 (2H), 7.76 (2H), 7.67 (2H), 7.01 (2H), 4.83 (2H), 4.59 (2H), 3.72 (6H), 2.74 (4H), 2.38 (6H), 2.09 (4H). MS: 471.

5,9-bis(4,4-diethoxy-10-methyl-9-oxo-3-oxa-8,10-diaza-4-silatridecan-13-yl)-1,13-dimethoxy-5,9-dihydro-13bH-quinolino[2,3,4-kl]acridin-13b-ylium hexafluorophosphate. (R1C)

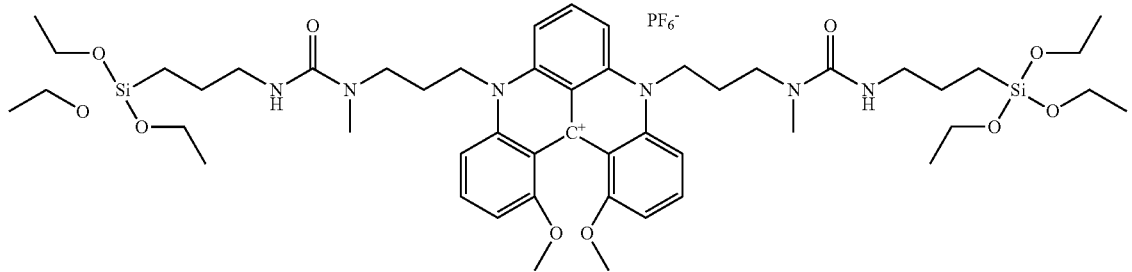

Prepared following procedure analogous to that described for I1C. MR-75.4_DMQA (1.0 g), $CH_2Cl_2$ (12 ml), 3-isocyanatopropyltriethoxysilane (0.85 ml) was added in one portion. Yield: 1 g (55%). $^1$H NMR (500 MHz, $CD_3CN$) δ 8.19 (1H), 7.91 (2H), 7.53 (2H), 7.47 (2H), 6.92 (2H), 5.31 (2H), 4.70 (2H), 4.48 (2H), 3.81-3.67 (18H), 3.60-3.54 (4H), 3.12 (4H), 2.95 (6H), 2.35-2.16 (2H), 1.59-1.47 (4H), 1.12 (18H), 0.62-0.55 (4H). $^{13}$C NMR (125 MHz, CD$_3$CN) δ 160.64, 159.31, 143.47, 142.92, 139.85, 138.03, 137.47, 120.29, 113.92, 108.24, 105.68, 103.98, 59.00, 56.49, 48.74, 46.64, 44.12, 35.12, 25.96, 24.62, 18.67, 8.24. MS: 965.

REFERENCES

1 Borisov, S. M. & Wolfbeis, O. S. Optical biosensors. *Chem. Rev.* 108, 423-461 (2008).
2 McDonagh, C., Burke, C. S. & MacCraith, B. D. Optical chemical sensors. *Chem. Rev.* 108, 400-422 (2008).
3 Wolfbeis, O. S. Fiber-Optic Chemical Sensors and Biosensors. *Anal. Chem.* 80, 4269-4283 (2008).
4 Wang, X. D. & Wolfbeis, O. S. Fiber-optic chemical sensors and biosensors (2008-2012). *Anal Chem* 85, 487-508, doi:10.1021/ac303159b (2013).
10A Laursen, B. W. & Krebs, F. C. Synthesis of a triazatriangulenium salt. *Angew. Chem. Int. Ed.* 39, 3432-3434 (2000).
11A Laursen, B. W. & Krebs, F. C. Synthesis, structure, and properties of azatriangulenium salts. *Chem. Eur. J.* 7, 1773-1783 (2001).
10. T. Ueno, Y. Urano, K. Setsukinai, H. Takakusa, H. Kojima, K. Kikuchi, K. Ohkubo, S. Fukuzumi and T. Nagano, *J. Am. Chem. Soc.*, 2004, 126, 14079-14085.
11. Y. Urano, M. Kamiya, K. Kanda, T. Ueno, K. Hirose and T. Nagano, *J. Am. Chem. Soc.*, 2005, 127, 4888-4894.
13. A. J. Bryan, A. P. Desilva, S. A. Desilva, R. Rupasinghe and K. Sandanayake, *Biosensors*, 1989, 4, 169-179.
14. A. Minta, J. P. Y. Kao and R. Y. Tsien, *J. Bio. Chem.*, 1989, 264, 8171-8178.
15. T. J. Rink, R. Y. Tsien and T. Pozzan, *J. Cell Biol.*, 1982, 95, 189-196.
17. A. Loudet and K. Burgess, *Chem. Rev.*, 2007, 107, 4891-4932.
22 Mikkelsen, M. B. et al. Controlled deposition of sol-gel sensor material using hemiwicking. *Journal of Micromechanics and Microengineering* 21, 115008 (2011).
23 Martin, J. C. & Smith, R. G. FACTORS INFLUENCING BASICITIES OF TRIARYLCARBINOLS SYNTHESIS OF SESQUIXANTHYDROL. *J. Am. Chem. Soc.* 86, 2252-2256 (1964)

The invention claimed is:
1. A fluorescent dye compound of Formula (I)

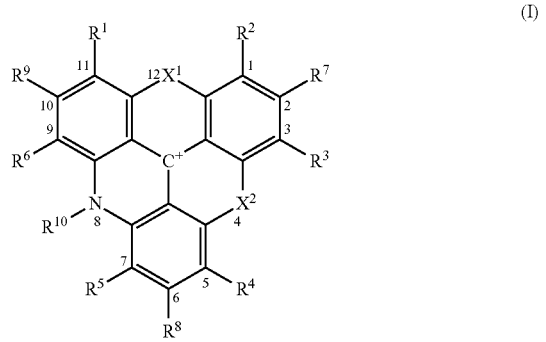

wherein
X$^1$ denotes NR$^{11}$, O, S, or C(R$^{11}$)$_2$, or denotes two individual substituted or unsubstituted C$_1$-C$_{24}$-alkoxy groups, which each are linked to the two adjacent carbon atoms, X$^2$ denotes NR$^{12}$, O, S, or C(R$^{12}$)$_2$, or denotes two individual substituted or unsubstituted C$_1$-C$_{24}$-alkoxy groups, which each are linked to the two adjacent carbon atoms, R$^1$, R$^2$, R$^3$, R$^4$, R$^5$, R$^6$, R$^7$, R$^8$, R$^9$, R$^{10}$, R$^{11}$ and R$^{12}$ are independently selected from hydrogen, cyano, halogen, hydroxy, nitro, acyl, acylamino, acyloxy, C$_1$-C$_{24}$-alkyl, C$_2$-C$_{24}$-alkenyl, C$_2$-C$_{24}$-alkynyl, aryl, C$_1$-C$_{24}$-alkoxy, C$_1$-C$_{24}$-alkylsulfonyl, methylsulfonyl, triflouromethyl, amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, sulfonyl, sulfonyloxy, thioacyl, thiol, thiocarbonyl, C$_1$-C$_{24}$-alkylthio, heteroaryl, cycloalkyl, phenyl, hydroxyphenyl, aminophenyl, amino-C$_1$-C$_{24}$-alkyl, or heterocyclyl selected from a 5- or 6-membered heterocyclyl containing at least one nitrogen or sulphur atom, or two of R$^1$, R$^2$, R$^3$, R$^4$, R$^5$, R$^6$, R$^7$, R$^8$, R$^9$, R$^{10}$, R$^{11}$ and R$^{12}$ may together form a ring system; R$^1$, R$^2$, R$^3$, R$^4$, R$^5$, R$^6$, R$^7$, R$^8$, R$^9$, R$^{10}$, R$^{11}$ and R$^{12}$ optionally being substituted once, twice, or three times with R$^{13}$ substituent(s), or a L-Si(OR$^{14}$)$_3$ substituent, R$^{13}$ is independently selected from hydrogen, cyano, halogen, hydroxy, nitro, acyl, acylamino, acyloxy, C$_1$-C$_{24}$-alkyl, C$_2$-C$_{24}$-alkenyl, C$_2$-C$_{24}$-alkynyl, aryl, C$_1$-C$_{24}$-alkoxy, C$_1$-C$_{24}$-alkylsulfonyl, methylsulfonyl, triflouromethyl, amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, sulfonyl, sulfonyloxy, thioacyl, thiol, thiocarbonyl, C$_1$-C$_{24}$-alkylthio, heteroaryl, or a cycloalkyl, or two R$^{13}$ substituents may together form a ring system, R$^{14}$ is independently selected from hydrogen, or straight or branched C$_1$-C$_6$ alkyl, alkenyl, or alkynyl, and one or more of the substituents R$^1$, R$^2$, R$^3$, R$^4$, R$^5$, R$^6$, R$^7$, R$^8$, R$^9$, R$^{10}$, R$^{11}$ or R$^{12}$ is/are a quenching group independently selected from phenyl substituted with one to five R$^{13}$ substituent(s) wherein at least one R$^{13}$ substituent is hydroxy, or a group selected from indole, benzoefuran, naphthalene, a 5- or 6-membered heterocyclyl or a C$_1$-C$_6$ alkylene heterocyclyl containing at least one of N, NH, O, or S, said group being substituted one, two, or three times with R$^{13}$ substituent(s), wherein at least one R$^{13}$ substituent, attached to indole, benzoefuran, naphthalene, the 5- or 6-membered heterocyclyl, or the heterocyclyl moiety of C$_1$-C$_6$ alkylene heterocyclyl is hydroxy, and optionally together with a counter ion.

2. The compound of Formula (I) according to claim 1, wherein at least one of the following substituents, R$^{10}$, R$^{11}$ and R$^{12}$, is a quenching group independently selected from the group comprising phenol, benzoefuran, indole, pyrrolidine, pyrrole, thiolane, thiophene, imidazolidine, pyrazolidine, imidazole, pyrazole, oxazolidine, isoxazolidine, oxazole, isoxazole, thiazolidine, isothiazolidine, thiazole, isothiazole, dithiolane, triazoles, furazan, oxadiazole, thiadiazole, dithiazole, tetrazole, piperidine, pyridine, thiane, thiopyran, piperazine, diazines, oxazine, thiazine, dithiane, dithiine, triazine, or tetrazine optionally substituted once, twice, three times with R$^{13}$ substituent(s).

3. The compound of Formula (I) according to claim 1, wherein R$^{10}$, R$^{11}$ and R$^{12}$ is a quenching group independently selected from the group comprising 2-phenol, 3-phenol, 4-phenol, hydroxy-indole, hydroxy-pyrrolidine, hydroxy-pyrrole, hydroxy-thiophene said group optionally being substituted once, two, or three times with $R^{13}$ substituent(s).

4. The compound of Formula (I) according to claim 1 selected from the group consisting of
9-(2,6-dimethoxyphenyl)-10-(3-hydroxyphenyl)-1,8-dimethoxy-acridinium (1c),
9-(2,6-dimethoxyphenyl)-10-(4-hydroxyphenyl)-1,8-dimethoxy-acridinium (1d),
9-(2,6-dimethoxyphenyl)-10-(2-hydroxy-5-(methylsulfonyl)phenyl)-1,8-dimethoxy-acridinium (1g),
5-(dodecyl)-9-(3-hydroxyphenyl)-1, 1 3-dimethoxy-quin[2,3,4-k]acridinium, (2c),
5-(4-aminophenyl)-9-(3-hydroxypropyl)-1, 1 3-dimethoxy-quin[2,3,4-k]acridinium (2e),
5-(dodecyl)-9-(5-fluor-2-hydroxyphenyl)-1, 1 3-dimethoxy-quin[2,3,4-k]acridinium (2f),
5-(dodecyl)-9-(5-methylsulfonyl-2-hydroxyphenyl)-1, 13-dimethoxy-quin[2,3,4-k]acridinium (2g),
5-(dodecyl)-9-(5-trifluormethyl-2-hydroxyphenyl)-1,13-dimethoxy-quin[2,3,4-k]acridinium (2h),
1 2-(2-hydroxyphenyl)-4-aza-8, 1 2-dioxa-4, 8,12,12c-tetrahydro-dibenzo[cd,mn]-pyrenylium (3b),
12-(3-hydroxyphenyl)-4-aza-8,12-dioxa-4,8,12, 12c-tetrahydro-dibenzo[cd,mn]-pyrenylium (3c),
4-(3-hydroxyphenyl)-azadioxatriangulenium tetrafluoroborat 3d,
4-dodecyl-8-(2-hydroxyphenyl)-4, 8-diaza-12-oxa-4,8, 12, 12c-tetrahydro-dibenzo[cd,mn]-pyrenylium (4b),
4-dodecyl-8-(5-fluoro-2-hydroxyphenyl)-4, 8-diaza-12-oxa-4,8,12, 12c-tetrahydro-dibenzo[cd,mn]-pyrenylium (4f),
4-dodecyl-8-(2-hydroxy-5-(methylsulfonyl)phenyl)-4,8-diaza-1 2-oxa-4,8,12, 12c-tetrahydro-dibenzo[cd,mn]-pyrenylium (4g),
4-dodecyl-8-(2-hydroxy-5-trifluoromethyl-phenyl)-4,8-diaza-1 2-oxa-4,8,12, 12c-tetrahydro-dibenzo[cd,mn]-pyrenylium (4h),
4-propyl-8-(2-hydroxyphenyl)-4,8-diaza-12-oxa-4,8,12, 12c-tetrahydro-dibenzo[cd,mn]-pyrenylium (4i),
4-propyl-8-(3-hydroxyphenyl)-4,8-diaza-12-oxa-4,8,12, 12c-tetrahydro-dibenzo[cd,mn]-pyrenylium (4j),
4-propyl-8-(4-hydroxyphenyl)-4,8-diaza-12-oxa-4,8,12, 12c-tetrahydro-dibenzo[cd,mn]-pyrenylium (4k),
4-propyl-8-(5-fluoro-2-hydroxyphenyl)-4,8-diaza-12-oxa-4,8,12, 12c-tetrahydro-dibenzo[cd,mn]-pyrenylium (4l),
4-propyl-8-(5-trifluoromethyl-2-hydroxyphenyl)-4,8-diaza-12-oxa-4,8,12, 12c-tetrahydro-dibenzo[cd,mn]-pyrenylium (4m),
4-propyl-8-(2-hydroxy-5-(methylsulfonyl)phenyl)-4,8-diaza-1 2-oxa-4,8,12, 12c-tetrahydro-dibenzo[cd,mn]-pyrenylium (4n),
8-(hydroxy-pyridin)-4,8-diaza-12-oxa-4,8,12,12c-tetrahydro-dibenzo[cd,mn]-pyrenylium (4o),
8-(hydroxy-1-methyl-1H-pyrrol)-4,8-diaza-12-oxa-4,8, 12, 12c-tetrahydro-dibenzo[cd,mn]-pyrenylium (4p),
8-(hydroxy-thiophen)-4,8-diaza-12-oxa-4,8, 12, 12c-tetrahydro-dibenzo[cd,mn]-pyrenylium (4q),
8-(hydroxy-1-methyl-1H-indol)-4,8-diaza-12-oxa-4,8,12, 12c-tetrahydro-dibenzo[cd,mn]-pyrenylium (4r),
8-(hydroxy-naphthalen)-4,8-diaza-12-oxa-4,8,12, 12c-tetrahydro-dibenzo[cd,mn]-pyrenylium (4s),
8-(hydroxybenzofuranyl)-4, 8-diaza-12-oxa-4,8,12, 12c-tetrahydro-dibenzo[cd,mn]-pyrenylium (4u),
4-(2-hydroxy-5-methylsulfonyl-phenyl)-8,12-diphenyl-4, 8,12-triaza-4,8,12, 12c-tetrahydro-dibenzo[cd,mn]-pyrenylium (5),
4-(2-hydroxyphenyl)-4-aza-8, 12-dioxatriangulenium hexafluorophophate (MR-68.1-ADOTA),
4-(2-hydroxyphenyl)-8-methyl-4, 8-diaza-1 2-oxatriangulenium hexafluorophosphate (MR-68-DAOTA),
4-(3-hydroxyphenyl)-4-aza-8, 12-dioxatriangulenium hexafluorophophate (MR-73-ADOTA),
4-(3-hydroxyphenyl)-8-methyl-8-aza-8, 12-dioxatriangulenium hexafluorophosphat, (MR-73.1-DAOTA),
4-(4-hydroxyphenyl)-4-aza-8, 11-dioxatriangulenium hexafluorophosphate (MR-93_ADOTA),
4-(4-hydroxyphenyl)-4, 8-diaza-11-oxatriangulenium hexafluorophosphate (MR-93_DAOTA),
4-(2-hydroxy-5-(trifluoromethyl)phenyl)-3-aza-8, 11-dioxatriangulenium hexafluorophosphate (MR-66.1_ADOTA),
4-(2-hydroxy-5-(trifluoromethyl)phenyl)-8-methyl-8-aza-11-oxatriangulenium hexafluorophosphate (MR-66_DAOTA),
4-(3-hydroxy-5-(trifluoromethyl)phenyl)-4-aza-8, 11-dioxatriangulenium hexafluorophosphate (MR-67.1_ADOTA),
4-(3-hydroxy-5-(trifluoromethyl)phenyl)-4-methyl-4, 11-diaza-8-oxatriangulenium hexafluorophosphate (MR-67.1_DAOTA),
3-(2-hydroxy-5-nitrophenyl)-7, 10-dioxa-3-azatriangulenium hexafluorophosphate (MR-69.1_ADOTA),
4-(2-hydroxy-5-nitrophenyl)-8-methyl-8-aza-11-oxatriangulenium hexafluorophosphate (MR-69_DAOTA),
8-(3-(N-methylamino)propyl-4, 8-diazatriangulenium-4-(4-(trifluoromethyl)phenolate) (MR-66_DAOTANH.1),
4-(2-hydroxy-5-(methylsulfonyl)phenyl)-4-aza-8, 12-dioxatriangulenium hexafluorophosphate (MR-49.6_ADOTA), and
8-(3-(N-methylamino)propyl-4, 8-diazatriangulenium-4-(4-(methylsulfonyl)phenolate) (MR-49.6_DAOTANH).

5. The compound of Formula (I) according to claim 1, further comprising a compound of Formula (II)

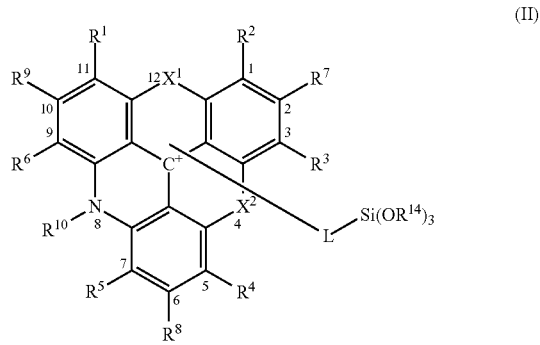

(II)

wherein
$X^1$ denotes $NR^{11}$, O, S, or $C(R^{11})_2$, or denotes two individual substituted or unsubstituted $C_1$-$C_{24}$-alkoxy groups, which each are linked to the two adjacent carbon atoms,
$X^2$ denotes $NR^{12}$, O, S, or $C(R^{12})_2$, or denotes two individual substituted or unsubstituted $C_1$-$C_{24}$-alkoxy groups, which each are linked to the two adjacent carbon atoms, at least one of the substituents $R^1$, $R^2$, $R^3$, $R^4$, $R^5$, $R^6$, $R^7$, $R^8$, $R^9$, $R^{10}$, $R^{11}$ or $R^{12}$ is attached to a linker L, or $R^{10}$, $R^{11}$ or $R^{12}$ is a linker L, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, cyano, halogen, hydroxy, nitro, acyl, acylamino, acyloxy, $C_1$-$C_{24}$-alkyl, $C_1$-$C_{24}$-alkenyl, $C_1$-$C_{24}$-alkynyl, aryl, $C_1$-$C_{24}$-alkoxy, $C_1$-$C_{24}$-alkylsulfonyl, methylsulfonyl, triflouromethyl, amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, sulfonyl, sulfonyloxy, thioacyl, thiol, thiocarbonyl, $C_1$-$C_{24}$-alkylthio, heteroaryl, cycloalkyl, phenyl, hydroxyphenyl, aminophenyl, amino-$C_1$-$C_{24}$-alkyl, or heterocyclyl selected from a 5- or 6-membered heterocyclyl containing at least one nitrogen or sulphur atom; $R^1$, $R^2$, $R^3$, $R^4$, $R^5$, $R^6$, $R^7$, $R^8$, $R^9$, $R^{10}$, $R^{11}$ and $R^{12}$ optionally being substituted once, twice, or three times with $R^{13}$ substituent(s), $R^{13}$ is independently selected form hydrogen, cyano, halogen, hydroxy, nitro, acyl, acylamino, acyloxy, $C_1$-$C_{24}$-alkyl, $C_2$-$C_{24}$-alkenyl, $C_2$-$C_{24}$-alkynyl, aryl, $C_1$-$C_{24}$-alkoxy, $C_1$-$C_{24}$-alkylsulfonyl, methylsulfonyl, triflouromethyl, amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, sulfonyl, sulfonyloxy, thioacyl, thiol, thiocarbonyl, $C_1$-$C_{24}$-alkylthio, heteroaryl, or a cycloalkyl, $R^{14}$ is independently selected from hydrogen, or straight or branched $C_1$-$C_6$-alkyl, alkenyl, or alkynyl, and optionally together with a counter ion, L is substituted or unsubstituted $C_1$-$C_{24}$ alkylene, alkenylene, alkynylene group optionally interrupted in the carbon chain with one or more heteroatoms selected from O, S, and NH, optionally L may be substituted with $R^{13}$, and one or more of the substituents $R^1$, $R^2$, $R^3$, $R^4$, $R^5$, $R^6$, $R^7$, $R^8$, $R^9$, $R^{10}$, $R^{11}$ or $R^{12}$ is/are a quenching group independently selected from phenyl substituted with one to three $R^{13}$ substituent(s) wherein at least one $R^{13}$ substituent is hydroxy, or a group selected from indole, benzoefuran, naphthalene, era 5- or 6-membered heterocyclyl or $C_1$-$C_6$ alkylene heterocyclyl containing at least one of N, NH, O, or S, said group being substituted one, two, or three times with $R^{13}$ substituent(s), wherein at least one $R^{13}$ substituent, attached to indole, benzoefuran, naphthalene, the 5- or 6-membered heterocyclyl, or the heterocyclyl moiety of $C_1$-$C_6$ alkylene heterocyclyl, is hydroxy, and optionally together with a counter ion.

6. The compound of Formula (II) according to claim 5 selected from the group consisting of N-(2-hydroxy-5-(trifluoromethyl)phenyl)-N'-(6-aza-4-oxa-5-oxo-9-trimethoxysilyl-nonan)-diazaoxatriangulenium hexafluorophosphat (6), 8-(1-methyl-1-propyl-3-(3-(triethoxysilyl)propyl) urea)-4, 8-diazatriangulenium-4-(4-(trifluoromethyl)phenolate) (I1C), and 8-(1-methyl-1-propyl-3-(3-(triethoxysilyl)propyl)urea)-4, 8-diazatriangulenium-4-(4-(methylsulfonyl)phenolate) (12C).

7. The compound of Formula (I) according to claim 1 conjugated to a carrier molecule selected from the group comprising an amino acid, a peptide, a protein, a polysaccharide, a nucleoside, a nucleotide, an oligonucleotide, a nucleic acid polymer, a drug, a hormone, a lipid, a lipid assembly, a synthetic polymer, a polymeric microparticle, a biological cell, or a virus.

8. The compound of Formula (I) according to claim 1, attached to a solid support selected from the group comprising a microfluidic chip, a silicon chip, a microscope slide, a microplate well, cuvette, silica gels, polymeric membranes, particles, derivatized plastic films, glass beads, cotton, plastic beads, alumina gels, polysaccharides, polyvinylchloride, polypropylene, polyethylene, nylon, latex bead, magnetic bead, paramagnetic bead, or superparamagnetic bead, sepharose, poly(acrylate), polystyrene, poly(acrylamide), polyol, agarose, agar, cellulose, dextran, starch, FICOLL, heparin, glycogen, amylopectin, mannan, inulin, nitrocellulose, starch, or a sol-gel based matrix.

9. The method for monitoring or determining the concentration of an analyte, the method comprising:
(a) contacting a sample with a compound of Formula (I) according to claim 1 to form a contacted sample;
(b) illuminating the contacted sample to form an illuminated sample; and
(c) detecting a fluorescent emission from the illuminated sample,
wherein the fluorescent emission is used to monitor or determine the concentration of the analyte.

10. The method according to claim 9, wherein the analyte is selected from the group comprising $H^+$, $N^+$, $K^+$, $Ca^{2+}$, $O_2$, $CO_2$, $H_2O_2$, and metabolites.

11. The compound of compound of Formula (II) according to claim 5 conjugated to a carrier molecule selected from the group comprising an amino acid, a peptide, a protein, a polysaccharide, a nucleoside, a nucleotide, an oligonucleotide, a nucleic acid polymer, a drug, a hormone, a lipid, a lipid assembly, a synthetic polymer, a polymeric microparticle, a biological cell, or a virus.

12. The compound of compound of Formula (II) according to claim 5, attached to a solid support selected from the group comprising a microfluidic chip, a silicon chip, a microscope slide, a microplate well, cuvette, silica gels, polymeric membranes, particles, derivatized plastic films, glass beads, cotton, plastic beads, alumina gels, polysaccharides, polyvinylchloride, polypropylene, polyethylene, nylon, latex bead, magnetic bead, paramagnetic bead, or superparamagnetic bead, sepharose, poly(acrylate), polystyrene, poly(acrylamide), polyol, agarose, agar, cellulose, dextran, starch, FICOLL, heparin, glycogen, amylopectin, mannan, inulin, nitrocellulose, starch, or a sol-gel based matrix.

13. The method for monitoring or determining the concentration of an analyte, the method comprising:
(a) contacting a sample with a compound of compound of Formula (II) according to claim 5 to form a contacted sample;
(b) illuminating the contacted sample to form an illuminated sample; and
(c) detecting a fluorescent emission from the illuminated sample,
wherein the fluorescent emission is used to monitor or determine the concentration of the analyte.

14. The method according to claim 13, wherein the analyte is selected from the group comprising $H^+$, $Na^+$, $K^+$, $Ca^{2+}$, $O_2$, $CO_2$, $H_2O_2$, and metabolites.

* * * * *